United States Patent
Pearce et al.

(10) Patent No.: US 10,702,715 B2
(45) Date of Patent: Jul. 7, 2020

(54) RADIATION THERAPY PATIENT PLATFORM

(71) Applicant: RefleXion Medical, Inc., Hayward, CA (US)

(72) Inventors: William Pearce, Orinda, CA (US); Brent Harper, Pescadero, CA (US)

(73) Assignee: RefleXion Medical, Inc., Hayward, CA (US)

( * ) Notice: Subject to any disclaimer, the term of this patent is extended or adjusted under 35 U.S.C. 154(b) by 241 days.

(21) Appl. No.: 15/814,276

(22) Filed: Nov. 15, 2017

(65) Prior Publication Data
US 2018/0133508 A1     May 17, 2018

Related U.S. Application Data

(60) Provisional application No. 62/422,494, filed on Nov. 15, 2016.

(51) Int. Cl.
*A61N 5/10*     (2006.01)

(52) U.S. Cl.
CPC ........... *A61N 5/107* (2013.01); *A61N 5/1049* (2013.01); *A61N 5/1075* (2013.01); *A61N 2005/1051* (2013.01); *A61N 2005/1061* (2013.01); *A61N 2005/1076* (2013.01)

(58) Field of Classification Search
CPC ................ A61N 5/1075; A61N 5/1049; A61N 2005/1051; A61N 5/107; A61N 2005/1076; A61N 2005/1061
See application file for complete search history.

(56) References Cited

U.S. PATENT DOCUMENTS

| | | |
|---|---|---|
| 3,794,840 A | 2/1974 | Scott |
| 3,906,233 A | 9/1975 | Vogel |
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,642,464 A | 2/1987 | Mullani |

(Continued)

FOREIGN PATENT DOCUMENTS

| | | |
|---|---|---|
| CN | 1681436 A | 10/2005 |
| CN | 1960780 A | 5/2007 |

(Continued)

OTHER PUBLICATIONS

Chang, J.Y. et al. (2008). "Image-guided radiation therapy for non-small cell lung cancer," *J. Thorac. Oncol.* 3(2):177-186.

(Continued)

*Primary Examiner* — Christine H Matthews
*Assistant Examiner* — Joshua Daryl D Lannu
(74) *Attorney, Agent, or Firm* — Cooley LLP

(57) ABSTRACT

Described here are systems, devices, and methods for imaging and radiotherapy procedures. Generally, a radiotherapy system may include a radiotransparent patient platform, a radiation source coupled to a multi-leaf collimator, and a detector facing the collimator. The radiation source may be configured to emit a first beam through the collimator to provide treatment to a patient on the patient platform. A controller may be configured to control the radiotherapy system.

27 Claims, 38 Drawing Sheets

(56) References Cited

U.S. PATENT DOCUMENTS

| | | |
|---|---|---|
| 4,647,779 A | 3/1987 | Wong |
| 4,677,299 A | 6/1987 | Wong |
| 4,771,785 A * | 9/1988 | Duer .................. A61B 5/0555 324/318 |
| 4,868,844 A | 9/1989 | Nunan |
| 5,075,554 A | 12/1991 | Yunker et al. |
| 5,206,512 A | 4/1993 | Iwao |
| 5,207,223 A | 5/1993 | Adler |
| 5,272,344 A | 12/1993 | Williams |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,418,827 A | 5/1995 | Deasy et al. |
| 5,442,675 A | 8/1995 | Swerdloff et al. |
| 5,511,549 A | 4/1996 | Legg et al. |
| 5,668,371 A | 9/1997 | Deasy et al. |
| 5,724,400 A | 3/1998 | Swerdloff et al. |
| 5,751,781 A | 5/1998 | Brown et al. |
| 5,813,985 A | 9/1998 | Carroll |
| 5,818,902 A | 10/1998 | Yu |
| 5,851,182 A | 12/1998 | Sahadevan |
| 5,889,834 A | 3/1999 | Vilsmeier et al. |
| 5,937,028 A | 8/1999 | Tybinkowski et al. |
| 6,180,943 B1 | 1/2001 | Lange |
| 6,184,530 B1 | 2/2001 | Hines et al. |
| 6,188,748 B1 | 2/2001 | Pastyr et al. |
| 6,207,952 B1 | 3/2001 | Kan et al. |
| 6,260,005 B1 | 7/2001 | Yang et al. |
| 6,271,517 B1 | 8/2001 | Kroening, Jr. et al. |
| 6,281,505 B1 | 8/2001 | Hines et al. |
| 6,364,529 B1 | 4/2002 | Dawson |
| 6,385,288 B1 | 5/2002 | Kanematsu |
| 6,396,902 B2 | 5/2002 | Tybinkowski et al. |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,459,769 B1 | 10/2002 | Cosman |
| 6,560,311 B1 | 5/2003 | Shepard et al. |
| 6,618,467 B1 | 9/2003 | Ruchala et al. |
| 6,628,744 B1 | 9/2003 | Luhta et al. |
| 6,661,866 B1 | 12/2003 | Limkeman et al. |
| 6,696,694 B2 | 2/2004 | Pastyr et al. |
| 6,700,949 B2 | 3/2004 | Susami et al. |
| 6,730,924 B1 | 5/2004 | Pastyr et al. |
| 6,735,277 B2 | 5/2004 | McNutt et al. |
| 6,778,636 B1 | 8/2004 | Andrews |
| 6,792,078 B2 | 9/2004 | Kato et al. |
| 6,794,653 B2 | 9/2004 | Wainer et al. |
| 6,799,068 B1 | 9/2004 | Hartmann et al. |
| 6,810,103 B1 | 10/2004 | Tybinkowski et al. |
| 6,831,961 B1 | 12/2004 | Tybinkowski et al. |
| 6,865,254 B2 | 3/2005 | Nafstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,110,808 B2 | 9/2006 | Adair |
| 7,129,495 B2 | 10/2006 | Williams et al. |
| 7,154,096 B2 | 12/2006 | Amano |
| 7,167,542 B2 | 1/2007 | Juschka et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,301,144 B2 | 11/2007 | Williams et al. |
| 7,302,038 B2 | 11/2007 | Mackie et al. |
| 7,310,410 B2 | 12/2007 | Sohal et al. |
| 7,313,222 B2 | 12/2007 | Carlsson et al. |
| 7,331,713 B2 | 2/2008 | Moyers |
| 7,338,207 B2 | 3/2008 | Gregerson et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,433,503 B2 | 10/2008 | Cherek et al. |
| 7,446,328 B2 | 11/2008 | Rigney et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,545,911 B2 | 6/2009 | Rietzel et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,627,082 B2 | 12/2009 | Kojima et al. |
| 7,639,853 B2 | 12/2009 | Olivera et al. |
| 7,640,607 B2 | 1/2010 | Guertin et al. |
| 7,656,999 B2 | 2/2010 | Hui et al. |
| 7,679,049 B2 | 3/2010 | Rietzel |
| 7,715,606 B2 | 5/2010 | Jeung et al. |
| 7,742,575 B2 | 6/2010 | Bourne |
| 7,755,055 B2 | 7/2010 | Schilling |
| 7,755,057 B2 | 7/2010 | Kim |
| 7,778,691 B2 | 8/2010 | Zhang et al. |
| 7,784,127 B2 | 8/2010 | Kuro et al. |
| 7,792,252 B2 | 9/2010 | Bohn |
| 7,795,590 B2 | 9/2010 | Takahashi et al. |
| 7,820,975 B2 | 10/2010 | Laurence et al. |
| 7,839,972 B2 | 11/2010 | Ruchala et al. |
| 7,847,274 B2 | 12/2010 | Kornblau et al. |
| 7,869,562 B2 | 1/2011 | Khamene et al. |
| 7,942,843 B2 | 5/2011 | Tune et al. |
| 7,949,095 B2 | 5/2011 | Ning et al. |
| 7,952,079 B2 | 5/2011 | Neustadter et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,019,042 B2 | 9/2011 | Shukla et al. |
| 8,059,782 B2 | 11/2011 | Brown |
| 8,063,376 B2 | 11/2011 | Maniawski et al. |
| 8,116,427 B2 | 2/2012 | Kojima et al. |
| 8,122,542 B2 | 2/2012 | Reitz et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,193,508 B2 | 6/2012 | Shchory et al. |
| 8,198,600 B2 | 6/2012 | Neustadter et al. |
| 8,232,535 B2 | 7/2012 | Olivera et al. |
| 8,239,002 B2 | 8/2012 | Neustadter et al. |
| 8,280,002 B2 | 10/2012 | Bani-Hashemi et al. |
| 8,295,906 B2 | 10/2012 | Saunders et al. |
| 8,304,738 B2 | 11/2012 | Gagnon et al. |
| 8,306,185 B2 | 11/2012 | Bal et al. |
| 8,335,296 B2 | 12/2012 | Dehler et al. |
| 8,357,903 B2 | 1/2013 | Wang et al. |
| 8,376,613 B2 | 2/2013 | Moyers |
| 8,384,049 B1 | 2/2013 | Broad |
| 8,406,844 B2 | 3/2013 | Ruchala et al. |
| 8,406,851 B2 | 3/2013 | West et al. |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,536,547 B2 | 9/2013 | Maurer, Jr. et al. |
| 8,537,373 B2 | 9/2013 | Humphrey |
| 8,581,196 B2 | 11/2013 | Yamaya et al. |
| 8,588,367 B2 | 11/2013 | Busch et al. |
| 8,617,422 B2 | 12/2013 | Koschan et al. |

(56) References Cited

U.S. PATENT DOCUMENTS

| | | | |
|---|---|---|---|
| 8,664,610 B2 | 3/2014 | Chuang | |
| 8,664,618 B2 | 3/2014 | Yao | |
| 8,712,012 B2 | 4/2014 | O'Connor | |
| 8,716,669 B2 | 5/2014 | Myaoka et al. | |
| 8,748,825 B2 | 6/2014 | Mazin | |
| 8,767,917 B2 | 7/2014 | Ruchala et al. | |
| 8,841,628 B2 | 9/2014 | Kitano et al. | |
| 8,850,640 B2 | 10/2014 | Buettner | |
| 8,966,687 B2 | 3/2015 | Wilson et al. | |
| 8,992,404 B2 | 3/2015 | Graf et al. | |
| 9,061,141 B2 * | 6/2015 | Brunker | A61B 6/0442 |
| 9,179,982 B2 | 11/2015 | Kunz et al. | |
| 9,205,281 B2 | 12/2015 | Mazin | |
| 9,360,570 B2 | 6/2016 | Rothfuss et al. | |
| 9,370,672 B2 | 6/2016 | Parsai et al. | |
| 9,433,387 B2 | 9/2016 | Ahn | |
| 9,437,339 B2 | 9/2016 | Echner | |
| 9,437,340 B2 | 9/2016 | Echner et al. | |
| 9,440,094 B2 | 9/2016 | Filiberti | |
| 9,456,764 B2 | 10/2016 | Burke et al. | |
| 9,560,970 B2 | 2/2017 | Rose et al. | |
| 9,693,749 B2 | 7/2017 | Ni et al. | |
| 9,697,980 B2 | 7/2017 | Ogura et al. | |
| 9,700,475 B2 | 7/2017 | Morris | |
| 9,731,148 B2 | 8/2017 | Olivera et al. | |
| 9,878,180 B2 | 1/2018 | Schulte et al. | |
| 9,886,534 B2 | 2/2018 | Wan et al. | |
| 9,952,878 B2 | 4/2018 | Grimme et al. | |
| 9,974,496 B2 | 5/2018 | Liu et al. | |
| 10,159,853 B2 | 12/2018 | Kuusela et al. | |
| 10,478,133 B2 | 11/2019 | Levy et al. | |
| 2002/0085668 A1 | 7/2002 | Blumhofer et al. | |
| 2002/0191734 A1 | 12/2002 | Kojima et al. | |
| 2002/0193685 A1 | 12/2002 | Mate et al. | |
| 2003/0036700 A1 | 2/2003 | Weinberg | |
| 2003/0128801 A1 | 7/2003 | Eisenberg et al. | |
| 2003/0219098 A1 | 11/2003 | McNutt et al. | |
| 2004/0024300 A1 | 2/2004 | Graf | |
| 2004/0030246 A1 | 2/2004 | Townsend et al. | |
| 2004/0037390 A1 | 2/2004 | Mihara et al. | |
| 2004/0057557 A1 | 3/2004 | Nafstadius | |
| 2004/0158416 A1 | 8/2004 | Slates | |
| 2004/0184579 A1 | 9/2004 | Mihara et al. | |
| 2005/0028279 A1 * | 2/2005 | de Mooy | A61B 6/0442 5/601 |
| 2006/0002511 A1 | 1/2006 | Miller et al. | |
| 2006/0113482 A1 | 6/2006 | Pelizzari et al. | |
| 2006/0173294 A1 | 8/2006 | Ein-Gal | |
| 2006/0182326 A1 | 8/2006 | Schildkraut et al. | |
| 2006/0193435 A1 | 8/2006 | Hara et al. | |
| 2007/0003010 A1 | 1/2007 | Guertin et al. | |
| 2007/0003123 A1 | 1/2007 | Fu et al. | |
| 2007/0014391 A1 | 1/2007 | Mostafavi et al. | |
| 2007/0043289 A1 | 2/2007 | Adair | |
| 2007/0055144 A1 | 3/2007 | Neustadter et al. | |
| 2007/0075273 A1 | 4/2007 | Birgy et al. | |
| 2007/0164239 A1 | 7/2007 | Terwilliger et al. | |
| 2007/0211857 A1 | 9/2007 | Urano et al. | |
| 2007/0221869 A1 | 9/2007 | Song | |
| 2007/0242801 A1 | 10/2007 | Mackie et al. | |
| 2007/0265528 A1 | 11/2007 | Xu et al. | |
| 2007/0270693 A1 | 11/2007 | Fiedler et al. | |
| 2008/0031404 A1 | 2/2008 | Khamene et al. | |
| 2008/0043910 A1 | 2/2008 | Thomas | |
| 2008/0130825 A1 | 6/2008 | Fu et al. | |
| 2008/0152085 A1 | 6/2008 | Saracen et al. | |
| 2008/0205588 A1 | 8/2008 | Kim | |
| 2008/0217541 A1 | 9/2008 | Kim | |
| 2008/0253516 A1 | 10/2008 | Hui et al. | |
| 2008/0262473 A1 | 10/2008 | Kornblau et al. | |
| 2008/0273659 A1 | 11/2008 | Guertin et al. | |
| 2008/0298536 A1 | 12/2008 | Ein-Gal | |
| 2009/0003655 A1 | 1/2009 | Wollenweber | |
| 2009/0086909 A1 | 4/2009 | Hui et al. | |
| 2009/0116616 A1 | 5/2009 | Lu et al. | |
| 2009/0131734 A1 | 5/2009 | Neustadter et al. | |
| 2009/0256078 A1 | 10/2009 | Mazin | |
| 2010/0040197 A1 | 2/2010 | Maniawski et al. | |
| 2010/0054412 A1 | 3/2010 | Brinks et al. | |
| 2010/0063384 A1 | 3/2010 | Kornblau et al. | |
| 2010/0067660 A1 | 3/2010 | Maurer, Jr. et al. | |
| 2010/0069742 A1 | 3/2010 | Partain et al. | |
| 2011/0044429 A1 | 2/2011 | Takahashi et al. | |
| 2011/0092814 A1 | 4/2011 | Yamaya et al. | |
| 2011/0105895 A1 | 5/2011 | Kornblau et al. | |
| 2011/0105897 A1 | 5/2011 | Kornblau et al. | |
| 2011/0118588 A1 | 5/2011 | Kornblau et al. | |
| 2011/0215259 A1 | 9/2011 | Iwata | |
| 2011/0215529 A1 * | 9/2011 | Garrison | F01D 25/183 277/300 |
| 2011/0272600 A1 | 11/2011 | Bert et al. | |
| 2011/0301449 A1 | 12/2011 | Maurer, Jr. | |
| 2011/0309255 A1 | 12/2011 | Bert et al. | |
| 2011/0313231 A1 | 12/2011 | Guertin et al. | |
| 2012/0035470 A1 | 2/2012 | Kuduvalli et al. | |
| 2012/0043481 A1 | 2/2012 | Mansfield et al. | |
| 2012/0230464 A1 | 9/2012 | Ling et al. | |
| 2012/0323117 A1 | 12/2012 | Neustadter et al. | |
| 2013/0111668 A1 * | 5/2013 | Wiggers | A61B 6/0457 5/608 |
| 2013/0158382 A1 | 6/2013 | Chao | |
| 2013/0266116 A1 | 10/2013 | Abenaim et al. | |
| 2013/0343509 A1 | 12/2013 | Gregerson et al. | |
| 2014/0107390 A1 | 4/2014 | Brown et al. | |
| 2014/0228613 A1 | 8/2014 | Mazin et al. | |
| 2014/0239204 A1 | 8/2014 | Orton et al. | |
| 2014/0249348 A1 | 9/2014 | Mazin | |
| 2015/0018673 A1 | 1/2015 | Rose et al. | |
| 2015/0190658 A1 | 7/2015 | Yu | |
| 2016/0023019 A1 | 1/2016 | Filiberti et al. | |
| 2016/0331997 A1 | 11/2016 | Vilsmeier | |
| 2016/0361566 A1 | 12/2016 | Larkin et al. | |
| 2016/0374632 A1 | 12/2016 | David | |
| 2017/0014648 A1 | 1/2017 | Mostafavi | |
| 2017/0082759 A1 | 3/2017 | Lyu et al. | |
| 2017/0084025 A1 | 3/2017 | Lyu | |
| 2017/0209715 A1 | 7/2017 | Ruebel et al. | |
| 2017/0220709 A1 | 8/2017 | Wan et al. | |
| 2017/0281975 A1 | 10/2017 | Filiberti et al. | |
| 2018/0133518 A1 | 5/2018 | Harper et al. | |
| 2019/0070437 A1 | 3/2019 | Olcott et al. | |
| 2019/0091487 A1 | 3/2019 | Pal et al. | |
| 2019/0143145 A1 | 5/2019 | Laurence, Jr. et al. | |
| 2019/0255362 A1 | 8/2019 | Voronenko et al. | |

FOREIGN PATENT DOCUMENTS

| | | |
|---|---|---|
| CN | 101970043 A | 2/2011 |
| DE | 19728788 A1 | 1/1999 |
| DE | 10-2008-053321 A1 | 5/2010 |
| EP | 1 454 653 B1 | 9/2007 |
| EP | 2 188 815 B1 | 11/2011 |
| EP | 2 687 259 A1 | 1/2014 |
| EP | 1 664 752 B1 | 6/2017 |
| EP | 3 175 886 B1 | 6/2018 |
| IL | 208396 | 12/2010 |
| JP | 2003-534823 A | 11/2003 |
| JP | 2007-502166 A | 2/2007 |
| JP | 2007-507246 A | 3/2007 |
| JP | 2008-173299 A | 7/2008 |
| NL | 9520013 A | 2/1997 |
| WO | WO-89/10090 A1 | 11/1989 |
| WO | WO-95/22241 A1 | 8/1995 |
| WO | WO-00/15299 A1 | 3/2000 |
| WO | WO-2004/017832 A2 | 3/2004 |
| WO | WO-2004/017832 A3 | 3/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/094002 A2 | 8/2007 |
| WO | WO-2007/094002 A3 | 8/2007 |

(56) References Cited

FOREIGN PATENT DOCUMENTS

| WO | WO-2007/124760 A1 | 11/2007 |
|----|----|----|
| WO | WO-2008/019118 A2 | 2/2008 |
| WO | WO-2008/019118 A3 | 2/2008 |
| WO | WO-2008/024463 A2 | 2/2008 |
| WO | WO-2008/024463 A3 | 2/2008 |
| WO | WO-2009/114117 A2 | 9/2009 |
| WO | WO-2009/114117 A3 | 9/2009 |
| WO | WO-2010/015358 A1 | 2/2010 |
| WO | WO-2012/135771 A1 | 10/2012 |
| WO | WO-2015/042510 A1 | 3/2015 |
| WO | WO-2016/097977 A1 | 6/2016 |

OTHER PUBLICATIONS

Chen, Y. et al. (2011). Dynamic tomotherapy deliver, *Am. Assoc. Phys. Med.* 38:3013-3024.
Erdi, Y.E. (2007). "The use of PET for radiotherapy," *Curr. Medical Imaging Reviews* 3(1):3-16.
Extended European Search Report dated Mar. 31, 2017, for European Application No. 09 719 473.2, filed on Mar. 9, 2009, 8 pages.
Fan, Q. et al. (2013). "Toward a planning scheme for emission guided radiation therapy (EGRT): FDG based tumor tracking in a metastatic breast cancer patient," *Med. Phys.* 40:081708, 12 total pages.
Fan, Q. et al. (2012). "Emission guided radiation therapy for lung and prostate cancers: a feasibility study on a digital patient," *Med. Phys.* 39:7140-7152.
Dieterich, S. et al. (2003). "Skin respiratory motion tracking for stereotactic radiosurgery using the CyberKnife," *Elsevier Int'l Congress Series* 1256:130-136.
Galvin, J.M. (2018). "The multileaf collimator—A complete guide," 17 total pages.
Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report dated Mar. 7, 2018, for PCT Application No. PCT/US2017/061848, filed on Nov. 15, 2017, 4 pages.
International Search Report dated Mar. 13, 2018, for PCT Application No. PCT/US2017/061855, filed on Nov. 15, 2017, 4 pages.
Langen, K.M. et al. (2010). "QA for helical tomotherapy: Report of the AAPM task group 148," *Med. Phys.* 37:4817-4853.
Kapatoes, J. M. (2001). "On the accuracy and effectiveness of dose reconstruction for tomotherapy," *Physics in Med. Biol.* 46:943-966.
Kapatoes, J.M. et al. (2001). "A feasible method for clinical delivery verification and dose reconstruction in tomotherapy," *Med. Phys.* 28:528-542.
Keall, P.J. et al. (2001). "Motion adaptive x-ray therapy: a feasibility study," *Phys. Med. Biol.* 46:1-10.
Krouglicof, N. et al. (2013). "Development of a Novel PCB-Based Voice Coil Actuator for Opto-Mechatronic Applications," presented at *IEEE/RSJ International Conference on Intelligent Robots and Systems (IROS)*, Tokyo, Japan, Nov. 3-7, 2013, pp. 5834-5840.
Mackie, T.R. et al. (1993). "Tomotherapy: a new concept for the delivery of dynamic conformal radiotherapy," *Med. Phys.* 20:1709-1719.
Mazin, S.R. et al. (2010). "Emission-guided radiation therapy: biologic targeting and adaptive treatment," *J. Am. Coll. Radiol.* 7:989-990.
North Shore LIJ (2008). "IMRT treatment plans: Dosimetry measurements & monitor units validation," Fontenla, D.P. et al.,Prague 2008, 133 total pages.
Papanikolaou, N. et al. (2010). "MU-Tomo: Independent dose validation software for helical tomo therapy," *J. Cancer Sci. Ther.* 2:145-152.

Parodi, K. (2015). "Vision 20/20: Positron emission tomography in radiation therapy planning, delivery, and monitoring," *Med. Phys.* 42:7153-7168.
Prabhakar, R. et al. (2007). "An Insight into PET-CT Based Radiotherapy Treatment Planning," *Cancer Therapy* (5):519-524.
Schleifring (2013). Slip Ring Solutions—Technology, 8 total pages.
Tashima, H. et al. (2012). "A single-ring OpenPET enabling PET imaging during radiotherapy," *Phys. Med. Biol.* 57:4705-4718.
TomoTherapy® (2011). TOMOHD Treatment System, Product Specifications, 12 total pages.
Varian Medical Systems (2004). "Dynamic Targeting™ Image-Guided Radiation Therapy—A Revolution in Cancer Care," *Business Briefing: US Oncology Review*, Abstract only, 2 pages.
Varian Medical Systems (2013). "PerfectPitch 6 degrees of freedom couch—Advanced robotics for accurate patient setup," 2 total pages.
Wikipedia (2016). "Scotch yoke," Retrieved from https://en.wikipedia.org/wiki/Scotch_yoke, 3 pages.
Written Opinion of the International Searching Authority dated Mar. 7, 2018, for PCT Application No. PCT/US2017/061848, filed on Nov. 15, 2017, 5 pages.
Written Opinion of the International Searching Authority dated Mar. 13, 2018, for PCT Application No. PCT/US2017/061855, filed on Nov. 15, 2017, 6 pages.
Yamaya, T. et al. (2008). "A proposal of an open PET geometry," *Physics in Med. And Biology* 53:757-773.
International Search Report dated Jun. 14, 2019, for PCT Application No. PCT/US2019/017855, filed on Feb. 13, 2019, 4 pages.
Manikandan et al. (2013). "Role of step size and max dwell time in anatomy based inverse optimization for prostate implants," *J. Med. Phys.* 38:148-154.
Non-Final Office Action dated Jan. 7, 2020, for U.S. Appl. No. 15/814,222, filed Nov. 15, 2017, 13 pages.
Notice of Allowance dated Dec. 4, 2019, for U.S. App. No. 16/100,054, filed Aug. 9, 2018, 13 pages.
Written Opinion of the International Searching Authority dated Jun. 14, 2019, for PCT Application No. PCT/US2019/017855, filed on Feb. 13, 2019, 10 pages.
Elekta Oncology (2008). "HexaPOD™ evo RT System," Product Brochure, 8 total pages.
Glendinning, A.G. et al. (2001). "Measurement of the response of $Gd_2O_2S$:Tb phosphor to 6 MV x-rays," *Phys. Mol. Biol,* 46:517-530.
International Search Report dated Oct. 24, 2018, for PCT Application No. PCT/US2018/046132, filed on Aug. 9, 2018, 2 pages.
International Search Report dated Jan. 30, 2019, for PCT Application No. PCT/US2018/061099, filed on Nov. 14, 2018, 4 pages.
International Search Report dated Jan. 18, 2019, for PCT Application No. PCT/US2018/052272, filed on Sep. 21, 2018, 4 pages.
Kim, H. et al. (2009). "A multi-threshold method for the TOF-PET Signal Processing," *Nucl. Instrum. Meth. Phys. Res. A.* 602:618-621.
Lu, W. (2008). "Real-time motion-adaptive delivery (MAD) using binary MLC: I. Static beam (topotherapy) delivery," *Phys. Med. Biol.* 53:6491-6511.
Lu, W. (2009). "Real-time motion-adaptive-optimization (MAO) in tomotherapy," *Phys. Med. Biol.* 54:4373-4398.
McMahon, R. et al. (2008). "A real-time dynamic-MLC control algorithm for delivering IMRT to targets undergoing 2D rigid motion in the beam's eye view," *Med. Phys.* 35:3875-3888.
Olivera, G.H. et al. (2000), "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Written Opinion of the International Searching Authority dated Oct. 24, 2018, for PCT Application No. PCT/US2018/046132, filed on Aug. 9, 2018, 7 pages.
Written Opinion of the International Searching Authority dated Jan. 30, 2019, for PCT Application No. PCT/US2018/061099, filed on Nov. 14. 2018. 11 pages.
Written Opinion of the International Searching Authority dated Jan. 18, 2019, for PCT Application No. PCT/US2018/052272, filed on Sep. 21, 2018, 14 pages.

(56) References Cited

OTHER PUBLICATIONS

Corrected Notice of Allowability dated Jan. 29, 2020, for U.S. Appl. No. 16/100,054, filed Aug. 9, 2018, 4 pages.
Corrected Notice of Allowability dated Mar. 10, 2020, for U.S. Appl. No. 16/138,631, filed Sep. 21, 2018, 4 pages.
Notice of Allowance dated Jan. 21, 2020, for U.S. Appl. No. 16/138,631, filed Sep. 21, 2018, 11 pages.

\* cited by examiner

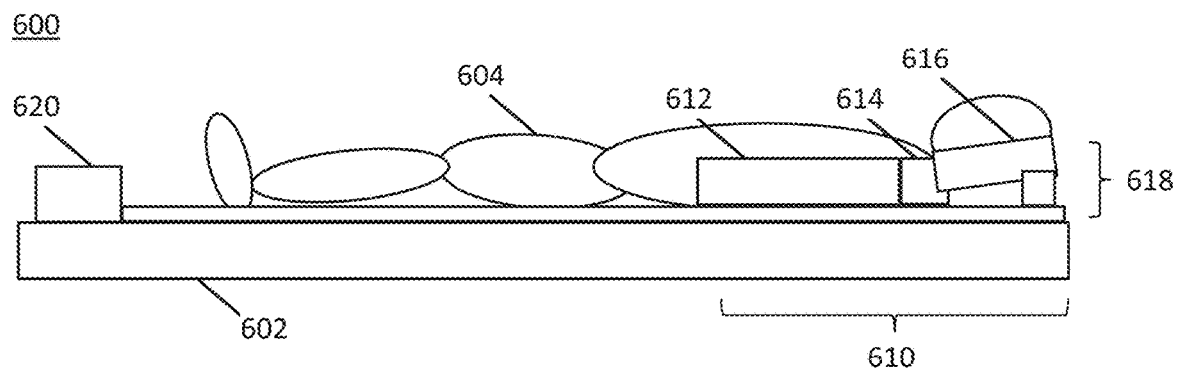
FIG. 6A
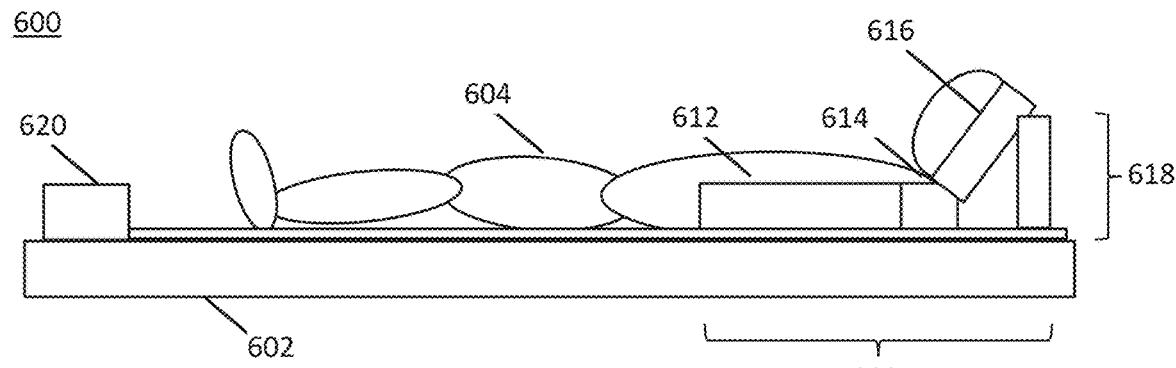
FIG. 6B
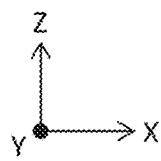

RADIATION THERAPY PATIENT PLATFORM

CROSS-REFERENCE TO RELATED APPLICATIONS

This application claims priority to U.S. Provisional Application Ser. No. 62/422,494, filed on Nov. 15, 2016, and titled "RADIATION THERAPY PATIENT PLATFORM," the content of which is hereby incorporated by reference in its entirety.

FIELD

The current invention relates to systems, devices, and methods for control of radiation therapy. The systems, devices, and methods may be used for emission-guided high-energy photon delivery.

BACKGROUND

Radiation therapy, or radiotherapy, uses high-energy photons to treat a variety of diseases. For instance, radiotherapy is commonly applied to cancerous tumors. Some radiotherapy systems deliver a beam of photons to a tumor using a radiation source or linear accelerator (linac) system. A linac may be mounted on a gantry that rotates around a patient. The gantry may be a C-arm gantry or a circular gantry. The linac may be rotated about the patient to concentrate a dose of photons at the tumor and reduce the radiation exposure of healthy tissue surrounding the tumor. A patient may be placed on a patient couch that moves in and out of a bore of a circular gantry for a patient to receive treatment.

For a rotating radiotherapy system to deliver effective treatment, the patient couch, herein referred to as a patient platform, must be nearly radiotransparent in a treatment beam plane and provide rigid support to a patient as the patient platform is cantilevered into and out of the bore of the gantry. However, due to a patient's weight and the length of platform, the platform will typically sag and introduce errors into a beam treatment plan. Moreover, typical carbon fiber patient platforms provide a generally uncomfortable, flat or slightly curved surface for a patient to lie on. This is of little consequence for imaging procedures that may be completed fairly quickly (e.g., in under an hour). By contrast, some radiotherapy treatments may require a patient to remain still for much longer periods of time (e.g., over an hour). Therefore, additional systems, devices, and methods for patient platform control and radiotherapy procedures may be desirable.

BRIEF SUMMARY

Described here are systems, devices, and methods for controlling the position of a patient in a radiotherapy system. Also described herein are systems, devices and methods for measuring patient platform sag during a treatment session, which may be used to aid delivery of radiotherapy treatment. In some variations, a system may comprise a patient platform having a patient region and a longitudinal axis, and a radiopaque elongate element coupled to the patient platform. The elongate element may comprise a longitudinal axis parallel to the longitudinal axis of the platform. Methods of quantifying a change in location of a radiotherapy patient platform due to a patient's weight may comprise emitting a first beam from a radiation source through a multi-leaf collimator to irradiate the radiopaque element. The multi-leaf collimator leaf pattern may be configured such that the first beam irradiates the radiopaque elongate element with little (if any) irradiation of the patient region of the patient platform. The first beam may be received by a detector facing the radiation source. A first location of the elongate element (e.g., when the platform is unweighted in the absence of a patient) may be determined using the detector. After a patient lies on the patient platform, a second beam may be emitted from the radiation source through the multi-leaf collimator, the multi-leaf collimator having the same leaf pattern as when the first beam was emitted. A second location of the elongate element (e.g., when the platform is weighted in the presence of a patient) may be determined using the detector. A change in location of the elongate element may be calculated between the first location and a second location of the elongate element, where the second location may correspond to a weighted platform. The change in location of the platform may be determined using the change in location of the elongate element.

The radiotransparent patient platform may comprise a first material substantially transparent to high energy photons and the radiopaque element may comprise a second material substantially opaque to the high energy photons. In some variations, the first location of the elongate element may be determined from a plurality of images of the elongate element using a radiation beam detector. In other variations, the first beam may be emitted from the radiation source relative to a horizontal plane between a first positive rotation angle and a second negative rotation angle. In some of these variations, the first beam may be emitted from the radiation source with the radiation source parallel to the horizontal plane.

In some variations, a radiotransparent patient platform system may comprise a radiotransparent patient platform having a radiopaque elongate element located along a longitudinal axis parallel to a longitudinal axis of the platform. The radiotransparent patient platform may comprise a first material substantially transparent to high energy photons and the radiopaque elongate element may comprise a second material substantially opaque to the high energy photons. The patient platform may comprise a first side having a patient support and a second side opposite the first side. The elongate element may be coupled to the second side of the patient platform. A radiotransparent support element may couple the elongate element to the patient platform. In some variations, the elongate element may comprise a metal rod. A radiation source may be coupled to a multi-leaf collimator. The radiation source may be configured to emit a first beam through the collimator to irradiate the elongate element. A detector may face the collimator and be configured to receive the first beam. A controller may be configured to determine a first location of the elongate element using the detector (e.g., when the platform is unweighted), calculate a change in location of the elongate element between the first location and a second location of the elongate element, where the second location corresponds to a weighted platform, and determine the change in location of the platform using the change in location of the elongate element.

Also described herein are methods for quantifying a change in location of a radiotherapy patient platform due to a patient. A patient platform may optionally comprise one or more optical markers, and a method of quantifying changes in the location of the platform may comprise imaging the one or more optical markers using an optical sensor. The one or more optical markers may comprise a longitudinal axis parallel to a longitudinal axis of the platform. The optical sensor may be coupled to a rotatable gantry. A first location of the optical marker may be determined using the optical sensor. A change in location of the optical marker may be calculated between the first location and a second location of the optical marker. The second location may correspond to a weighted platform. The change in location of the platform may be determined using the change in location of the one or more optical marker. In one variation, the second location of the optical marker may be determined using a plurality of images of the one or more optical markers (e.g., acquired by the optical sensor as the gantry rotates around the patient platform). A controller may be configured to determine a first location of the one or more optical markers using the one or more optical sensors (when the platform is unweighted). The second location may correspond to a weighted platform.

In some variations, the optical sensor may comprise an infrared sensor and/or an infrared illumination source. In another variation, the optical marker may comprise a retroreflector or reflector. In yet another variation, the optical sensor may comprise a laser. In one variation, the patient platform may comprise a first side including a patient support and a second side opposite the first side. The optical marker may be coupled to the second side of the patient platform.

Also described here are systems, devices, and methods for quality assurance of radiotherapy systems. For example, in order to determine whether a desired dose of radiation is being delivered by a radiotherapy system, radiation may be applied to a phantom comprising radiation sensors (e.g., dosimeter) at various locations in the phantom. The phantoms described herein may aid in calibration of the various components of a radiation system (e.g., radiation source, radiation detector, etc.). Generally, a system may comprise a patient platform having a patient support surface and an underside surface opposite the patient support surface. A phantom may be mounted to the underside surface. The phantom may comprise a plurality of steps having a corresponding predetermined depth, and a plurality of radiation detectors. Each of the radiation detectors may be disposed at the predetermined depth of its corresponding step. Alternatively or additionally, a phantom may comprise a plurality of radiation detectors, and a first region having a first density and a second region having a second density different from the first density. The radiation detectors and regions may each be arranged along the longitudinal axis.

In some variations, the radiation detectors may comprise ionization chambers and dosimeter slots. Ionization chambers may be arranged along a longitudinal axis of the phantom and along a vertical axis perpendicular to the longitudinal axis. The dosimeter slots may be parallel to the longitudinal axis and disposed at the predetermined depth of its corresponding step. In some variations, at least one of the dosimeter slots may be nearly parallel to a vertical axis perpendicular to a longitudinal axis of the phantom. In some other variations, the phantom may comprise a housing that defines an internal fluid-tight volume. A mount may couple the phantom to the patient platform. In some of these variations, the mount may be configured to slidably position the phantom relative to the patient platform.

In some variations, the radiation detectors may comprise ionization chambers and dosimeter slots. In some of these variations, each of the dosimeter slots may intersect its corresponding ionization chamber. The ionization chambers and dosimeter slots may be spaced apart from each other along the longitudinal axis. In some variations, a mount may couple the phantom to the patient platform. The mount may be configured to slidably position the phantom relative to the patient platform.

Also described are phantoms that may be useful for determining contrast resolution of a detector. In some variations, a system may comprise a patient platform having a patient support surface and an underside surface opposite the patient support surface, and a longitudinal axis. A phantom may be mounted to the underside surface. The phantom may comprise a first repeated pattern having a spatial frequency range and a second repeated pattern having a contrast range. The first pattern may comprise a series of high-contrast edges or stripes where the space between the edges or stripes varies in accordance with the spatial frequency range. The second pattern may comprise a series of repeating shapes that have different levels of contrast with respect to a background intensity. The first and second repeated patterns may be spaced along a longitudinal axis of the phantom. The spatial frequency range may be within a spatial frequency limit of a radiation detector and the contrast range may be within a contrast limit of the radiation detector.

In some variations, the first and second repeated patterns may comprise a set of contrasting shapes spaced apart at different intervals. The set of shapes may comprise a first shape having a first thickness and a second shape having a second thickness different from the first thickness. The set of shapes may comprise a first shape having a first density and a second shape having a second density different from the first density. In some variations, a width of the phantom may be aligned parallel to a length of the patient platform. In some variations, the phantom may be disposed within an imaging region of the patient platform. A mount may couple the phantom to the patient platform.

Also described herein are methods for adjusting a radiotransparent patient platform to a patient's body contour, which may improve patient comfort and radiotherapy procedure compliance. One variation of a radiotherapy patient platform systems may comprise a radiotransparent patient platform having a conformable substrate having a plurality of enclosures and a pressure sensor coupled to the conformable substrate. A controller may be configured to independently control a height of each of the plurality of enclosures using the pressure sensor. A method for adjusting the contours of a conformable substrate may comprise measuring a pressure of the patient platform using the pressure sensor(s). The pressure may comprise a plurality of enclosure pressures. The height of each of the plurality of enclosures may be independently controlled using the pressure such that the conformable substrate contours to a shape of a patient. For example, the plurality of enclosures may be coupled to a pressure source.

In some variations, the method may further comprise determining a patient configuration corresponding to the height of each of the plurality of enclosures. The patient configuration may comprise at least one of a pressure and the height of each of the plurality of enclosures. In some of these variations, the method may further comprise storing the patient configuration in memory, and readjusting the height of each of the plurality of enclosures using the stored patient configuration. In yet another variation, a thermoelectric layer of the patient platform may be heated to form a compliant configuration, and cooling the thermoelectric layer may form a rigid configuration.

In some variations, a pressure channel may couple a pressure source to each of the plurality of enclosures. In some of these variations, the pressure channel may comprise a radiotransparent material substantially transparent to high energy photons. In other variations, the plurality of enclosures may comprise a fluid. In some of these other variations, the fluid may comprise a gas. In one variation, a thermoelectric layer and a heating element may each be coupled to the patient platform. In some of these variations, the thermoelectric layer may transition between a compliant configuration and a rigid configuration based on temperature. In another variation, a thermal insulating layer may be coupled to the thermoelectric layer. In yet another variation, the plurality of enclosures may comprise a flexible membrane. In yet further variations, the plurality of enclosures may each comprise a honeycomb configuration.

Also described here are methods for calculating sag of a radiotransparent patient platform. A weighted patient platform having a reduced amount of sag may allow more accurate treatment planning and improved delivery of radiotherapy treatment. The patient platform may comprise an upper portion and a lower portion coupled to the upper portion. The upper portion and the lower portion may move relative to relative to each other or may move relative to a base. One variation of a method may comprise emitting an imaging beam using an imaging radiation source in an imaging plane perpendicular to a longitudinal axis of the patient platform. The lower portion may be non-intersecting with the imaging plane and the upper portion may intersect the imaging plane.

In some variations, a treatment beam may be emitted from a treatment radiation source coupled to a multi-leaf collimator in a treatment plane perpendicular to a longitudinal axis of the patient platform. The upper portion and the lower portion may be moved such that the lower portion is non-intersecting with the treatment plane and the upper portion intersects the treatment plane.

In other variations, moving the upper portion into the imaging plane may comprise positioning the lower portion such that a leading edge of the lower portion is located at a first distance away from the imaging plane. In some of these other variations, moving the upper portion into the treatment plane may comprise positioning the lower portion such that the leading edge of the lower portion is located at a second distance away from the treatment plane. The upper portion may comprise a first material substantially transparent to high energy photons and the lower portion may comprise a second material substantially opaque to the high energy photons.

One variation of a patient platform system may be configured to coordinate movement of a patient platform with the timing of imaging and/or treatment beam emission. In general, these systems may comprise a radiotransparent patient platform having an upper portion coupled to a lower portion. A base may be coupled to the lower portion of the patient platform. A radiation source may be coupled to a multi-leaf collimator. A controller may be configured to move the upper portion relative to the lower portion such that the upper portion is within a beam plane of the imaging and/or treatment beam while the lower portion is not within the beam plane (e.g., the lower portion may be non-intersecting with the beam plane and the upper portion may intersect the beam plane). The radiation source may be configured to emit a first beam in a beam plane perpendicular to a longitudinal axis of the patient platform.

Also described here are methods for controlling a radiotransparent patient platform. The patient platform may comprise an upper portion and a lower portion fixed to the upper portion. The upper portion and the lower portion may comprise different radiotransparency. The patient platform may move relative to a base. An imaging beam may be emitted by an imaging radiation source in an imaging plane perpendicular to a longitudinal axis of the patient platform. The lower portion may be non-intersecting with the imaging plane and the upper portion may intersect the imaging plane.

In some variations, the methods may further comprise emitting a treatment beam from a treatment radiation source coupled to a multi-leaf collimator in a treatment plane perpendicular to a longitudinal axis of the patient platform. The patient platform may move such that the lower portion is non-intersecting with the treatment plane and the upper portion intersects the treatment plane.

In other variations, moving the upper portion into the imaging plane may comprise positioning the lower portion such that a leading edge of the lower portion is located at a first distance away from the imaging plane.

In some of these variations, the upper portion may move into the treatment plane and may comprise positioning the lower portion such that the leading edge of the lower portion is located at a second distance away from the treatment plane. In another variation, the upper portion may comprise a first material substantially transparent to high energy photons and the lower portion may comprise a second material substantially opaque to the high energy photons.

Also described herein are radiotherapy patient platform systems. In general, the systems described herein may comprise a radiotransparent patient platform having an upper portion fixed to a lower portion. A base may be coupled to the lower portion of the patient platform. A radiation source may be coupled to a multi-leaf collimator. The radiation source may be configured to emit a first beam in a beam plane perpendicular to a longitudinal axis of the patient platform. A controller may be configured to move the patient platform relative to the base. The lower portion may be non-intersecting with the beam plane and the upper portion may intersect the beam plane.

Also described here are methods of irradiating a first region of interest of a patient. For example, a radiotherapy patient platform may be moved with respect to one or more regions of interest to aid delivery of radiotherapy treatment. In general, the methods may comprise moving a radiotherapy patient platform into a patient region of a gantry. The gantry may define an isocenter point about which the gantry rotates. An isocenter axis intersects the isocenter point and is in parallel with a first longitudinal axis of the patient region. The patient platform may move to position the first region of interest on the isocenter axis. A radiation beam may be emitted to the first region of interest on the isocenter axis from a radiation source.

In some variations, moving the patient platform to position the first region of interest on the isocenter axis may comprise moving the patient platform in a lateral direction. In other variations, at least one of pitch and yaw of the patient platform may rotate. In some of these variations, a second longitudinal axis of the first region of interest may align on the isocenter axis. In another variation, the patient may comprise a second region of interest. The patient platform may move to alternately position the first and second regions of interest on the isocenter axis. In some of these variations, a third longitudinal axis of the second region of interest may be aligned with the isocenter axis.

Also described herein are radiotherapy patient platform systems. For example, a radiotherapy patient platform may comprise one or more drive systems that may be configured to adjust the platform position or location with a plurality of degrees of freedom. In general, the systems may comprise a radiotransparent patient platform coupled to a base. The patient platform may comprise an upper portion coupled to a lower portion. An axial drive system may be coupled to the patient platform. The axial drive system may be configured to move the patient platform in an axial direction relative to the base. A lateral drive system may be coupled to the patient platform. The lateral drive system may be configured to move the patient platform in a lateral direction relative to the base. A vertical drive system may be coupled to the patient platform. The vertical drive system may be configured to move the patient platform in a vertical direction relative to the base. The vertical drive system may comprise a first and second scissor element coupled to the patient platform. A pitch drive system may be coupled to the platform. The pitch drive system may be configured to pitch the upper portion relative to the lower portion about a pitch pivot. A yaw pivot may couple the upper portion to the lower portion at respective first ends of the upper and lower portions. A yaw drive may be coupled to the first end of the upper portion. The yaw drive may be configured to yaw the upper portion relative to the lower portion about the yaw pivot.

In some variations, the pitch drive system may comprise a first wedge coupled to the yaw drive system and a second wedge coupled to the upper portion. In some variations, the axial drive system may be coupled between the lower portion and the lateral drive system. The lateral drive system may be coupled between the axial drive system and the yaw drive system. The yaw drive system may be coupled between the lateral drive system and the pitch drive system. The pitch drive system may be coupled between the yaw drive system and the upper portion.

In some variations, the axial drive system may comprise an axial drive element coupled to the first end of the lower portion and an axial rail coupled to the axial drive element. In other variations, the lateral drive system may comprise a lateral drive element coupled to the patient platform and a lateral rail coupled to the lateral drive element.

In another variation, the first scissor element may be coupled to the first end of the lower portion and the second scissor element may be coupled to a second end of the lower portion. In some variations, the vertical drive system may comprise a vertical drive element comprising a first linear screw coupled to the first scissor element. In some instances, the vertical drive element may comprise a second linear screw coupled to the second scissor element.

In some variations, the radiotherapy patient platform systems described herein may further comprise a handheld controller. The handheld controller may comprise a first switch and a docking port. The first switch may be configured to generate a movement signal. In some variations, the first switch may comprise at least one of a button, an analog stick, a trackball, a touch screen, a directional pad, a jog dial, a motion detector, an image sensor, and a microphone. In other variations, the system may comprise a proximity sensor configured to detect a proximity of the controller to the patient platform. The patient platform may be configured to move using the movement signal and the detected proximity. In another variation, the controller may comprise a wireless transmitter outputting the movement signal. In yet another variation, a tether may be coupled to the patient platform and the controller. In further variations, the movement signal may control at least four degrees of freedom of motion.

In some variations, the system may comprise a second switch. In some of these variations, the second switch may be a step switch. The controller may be configured to output the movement signal upon activation of the first and second switches. The controller may comprise the second switch and a housing. The first switch may be provided on a first side of the housing and the second switch may be provided on a second side of the housing opposite the first side.

Some of the radiotherapy patient platform systems described here may further comprise a head fixation device configured to hold a patient head in a predetermined position relative to a patient platform. Generally, the head fixation device may comprise having a hinge coupled to a base, a head rest coupled to the hinge, and a drive system coupled to the head rest. The drive system may be configured to extend substantially perpendicularly to the base. The head rest and the drive system may each comprise a radiotransparent material substantially transparent to high energy photons.

In some variations, the drive system may comprise a pneumatic element. In other variations, the drive system may comprise an electromechanical element. In another variation, an actuator may be coupled to the drive system. The actuator may be coupled to a first end of the patient platform. In further variations, the hinge may comprise a lock having a plurality of detents and a pin.

Also described here are methods of positioning a patient's head relative to a radiotherapy patient platform. For example, a head fixation device may be used to position a patient's head with respect to a patient platform to aid delivery of radiotherapy treatment. In general, the methods comprise coupling a patient's head to a head fixation device comprising a base coupled to a head rest by a hinge and a head rest drive system coupled to the head rest. The drive system may be extended substantially perpendicularly to the base.

In some variations, the head rest may be locked relative to the base. In other variations, at least one of a patient torso and a patient shoulder may be coupled to the base. In some other variations, the head rest may be pitched and yawed relative to the base. In yet other variations, the head rest may be pivoted about the hinge in response to neck flexion.

BRIEF DESCRIPTION OF THE DRAWINGS

FIG. 1A is a cross-sectional side view of a variation of a patient platform and gantry. FIGS. 1B-1F are cross-sectional front views of variations of the patient platform and gantry of FIG. 1A.

FIG. 2A is a perspective view of a variation of a patient supported by a conformable patient platform. FIG. 2B is a perspective view of the conformable patient platform of FIG. 2A. FIG. 2C is a cross-sectional side view of another variation of a patient supported by a conformable patient platform.

FIGS. 3A-3B are cross-sectional side views of a variation of a telescoping patient platform and gantry. FIGS. 3C-3D are cross-sectional side views of another variation of a telescoping patient platform and gantry.

FIGS. 4A-4B are side views of a variation of a patient platform system. FIG. 4C is a perspective view of the patient platform system of FIG. 4B. FIG. 4D is a side view of another variation of a patient platform system. FIG. 4E is a perspective view of the patient platform system of FIG. 4D. FIG. 4F is a perspective view of the patient platform system of FIG. 4C.

FIGS. 6A-6B are illustrative side views of a variation of a head fixation device.

DETAILED DESCRIPTION

Described herein are systems, devices, and methods useful for radiotherapy procedures. As used herein, radiotransparent refers to the property of being substantially transparent to high energy photons in that there is little or no attenuation of high energy photons. Conversely, radiopaque refers to the property of being substantially opaque to high energy photons. For instance, a radiopaque material may attenuate or block transmission of high energy photons.

Generally, to perform an imaging and/or radiotherapy procedure, a patient is loaded onto a patient platform. The patient platform may comprise carbon fiber due to its radiotransparency and ability to provide rigid support to a patient. Once loaded, the platform is moved into a patient region (e.g., bore, central opening, cavity) of a ring gantry. Typically, the large size and geometry of the gantry sets physical constraints on the configuration of the patient platform and other system components. In some radiotherapy systems, a gantry may comprise a C-arm shape that defines a patient region through which the patient platform may be extended into and out of. The gantry may comprise one or more beam delivery systems that may rotate about the patient platform and provide one or more imaging and/or treatment beams from a plurality of angles. In order to precisely and/or accurately deliver a treatment beam to a region of interest (e.g., lesion, tumor) of the patient, the location of the patient with respect to the gantry must be accurately determined and account for any sag, deviation, or deflection of the patient platform in the treatment beam plane. It should be appreciated that effective radiotherapy treatment is not only the ability to deliver high energy photons to a region of interest to treat a disease, but to do so while reducing delivery of high energy photons to healthy tissue. Otherwise, for example, a cancerous tumor may be treated at the cost of damage to healthy organs and tissue.

Figure 15:
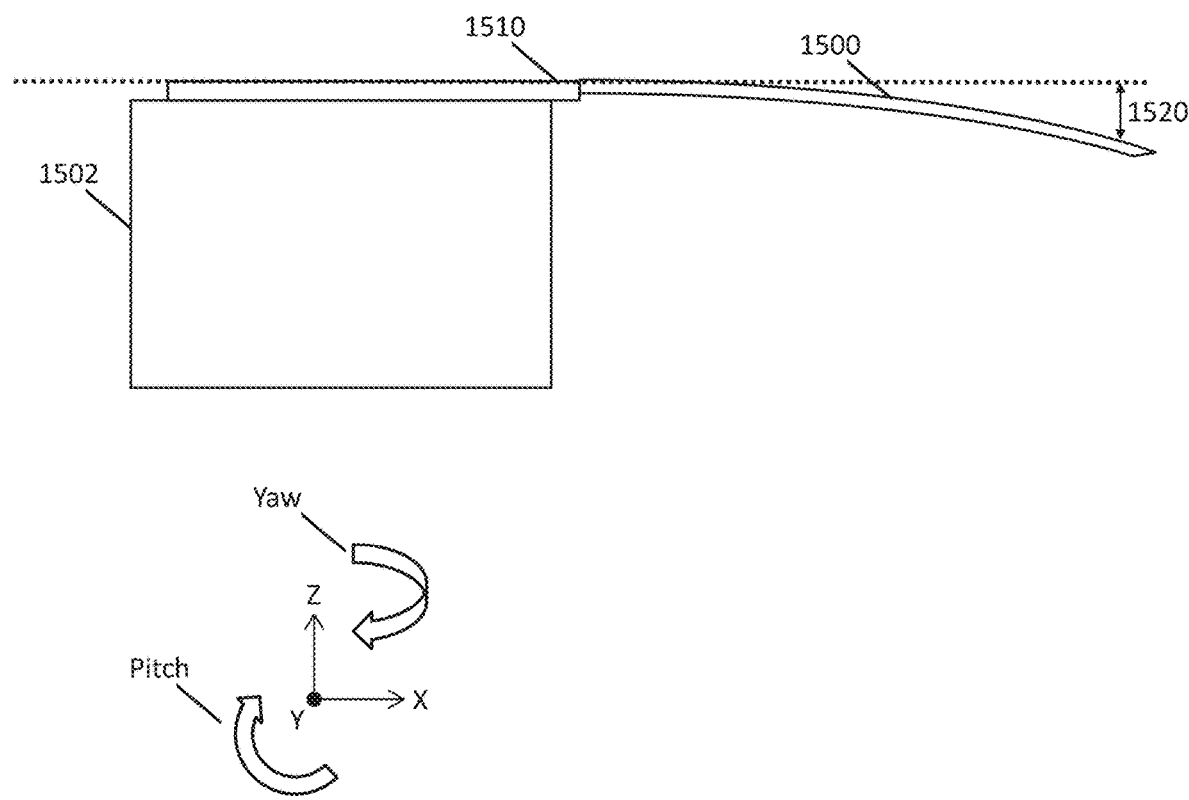
FIG. 15 is an illustrative depiction of sag of a patient platform.

Described further herein are systems, devices, and methods of controlling movement of a patient platform. For ease of explanation, a set of reference axes are defined in FIG. 15 to define a set of axes of translation and rotation with respect to a patient platform (1500), and are used throughout (e.g., FIGS. 1A-1F, 3A-3D, 4A-4F, 6A-6B, 13A-13E, 16A-16B, 17, 18, etc.) In particular, FIG. 15 is an illustrative depiction of sag (1520) of a patient platform (1500) in an X-Y plane. The patient platform (1500) may be coupled to and extend from a base (1502). A sag (1520) of the patient platform (1500) corresponds to the vertical distance (along the Z-axis) between a horizontal plane (1510) (e.g., X-Y plane) and the sagging patient platform (1500). The horizontal plane (1510) corresponds to the plane of an idealized patient platform mounted on the base (1502) that extends from the base (1502) without any deflection. As shown in FIG. 15, the sag (1520) of the patient platform (1500) may increase along the length of the patient platform (1500) extending from the base (1502). As used herein, axial movement corresponds to movement along the X-axis, vertical movement corresponds to movement along the Z-axis, and lateral movement corresponds to movement along the Y-axis (which extends into and out of the X-Z plane). As illustrated in FIG. 15, yaw rotation corresponds to rotation about the Z-axis and pitch rotation corresponds to rotation about the Y-axis.

In some variations of the system, a sag of an ideal patient platform may be measured and used to aid delivery of radiotherapy treatment. For instance, measuring the degree to which a patient platform sags may be used to adjust a treatment plan in order to accurately and/or more precisely apply radiation to a region of interest of a patient. In some of these variations, a patient platform may comprise a radiopaque elongate element. One or more leaves of a multi-leaf collimator of the gantry may be opened to selectively direct an imaging beam to intersect the elongate element and a detector located across from a radiation source as the gantry rotates about the patient platform. Various methods may be used to determine an amount of sag of the elongate element using the detector data, for example, a Winston-Lutz based method. In accordance with systems, devices, and methods herein, the patient platform sag and the location of the region of interest may be determined. Furthermore, by selecting image beam angles where radiation beams intersect the elongate element and not the patient, a location of a region of interest may be determined without exposing the patient to additional radiation. Accordingly, a treatment dose may be more accurately and/or more precisely delivered to a patient, thus sparing healthy tissue and improving dose delivery.

In some variations of the system, a conformable patient platform may be provided to improve patient platform ergonomics, reduce patient registration and setup time, and increase patient compliance. In some cases, a patient may be sedated to limit their movement on a patient platform. However, sedation poses risks and may be undesirable for some patient groups such as the elderly, patients with advanced disease, and/or patients taking medication. A conformable patient platform may facilitate patient comfort and encourage the patient to remain motionless for longer periods of time to receive radiotherapy treatment and may help to reduce the use of sedatives. In some of these variations, a configuration of the patient platform that may be unique or customized for a particular patient may be saved in a memory of the controller and may be reapplied for future procedures. The patient platforms described in further detail below may uniquely conform to each patient and serve as an ergonomic restraint to limit patient movement on the patient platform. Importantly, the conformable patient platform may be radiotransparent and it should be appreciated that the patient platforms described herein may be used for diagnostic imaging and/or radiotherapy procedures. In some variations, the patient platform may comprise a conformable substrate having a plurality of independently height adjustable enclosures that may deform and rigidize to contour to a shape of a patient. In other variations, the patient platform may comprise a thermoelectric layer that forms a compliant configuration when heated and a rigid configuration when cooled.

Figure 1A:
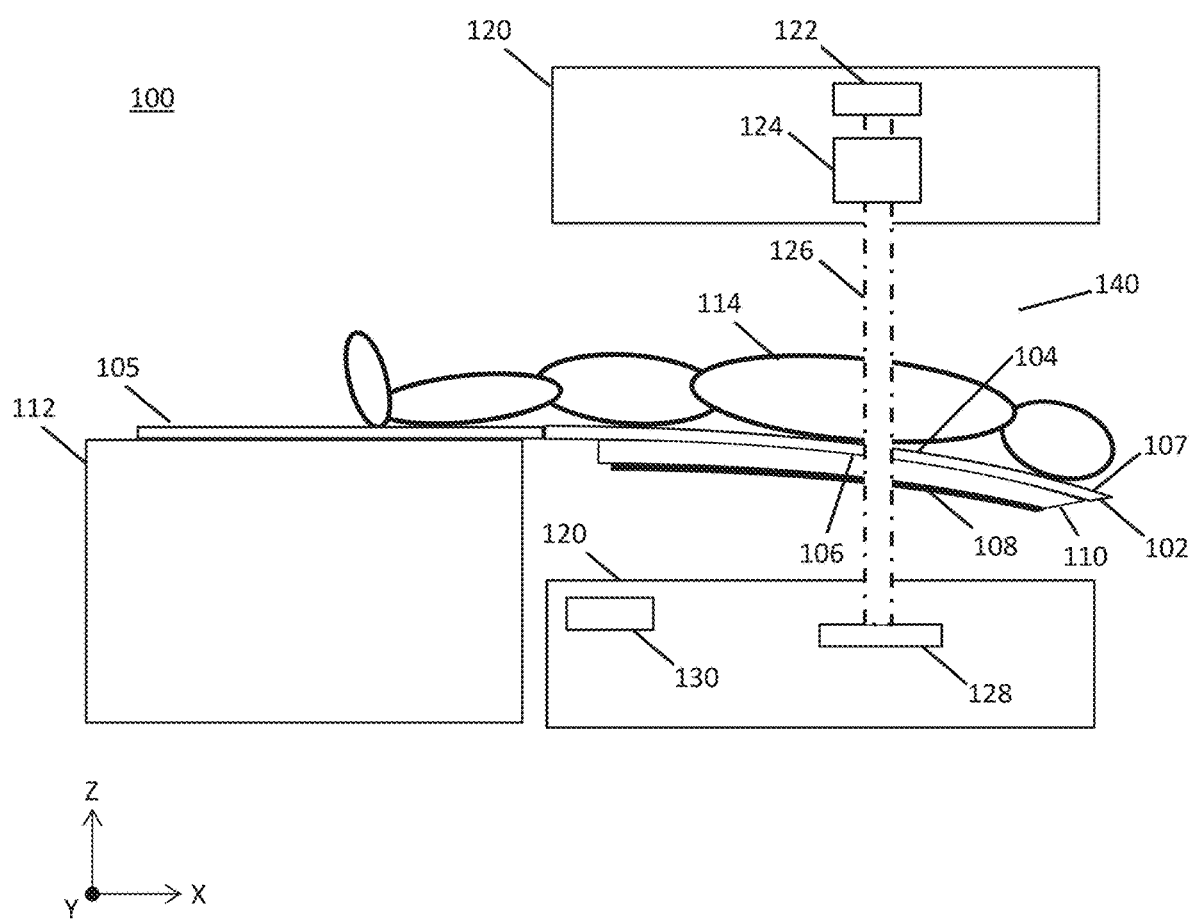
FIGS. 1A-1F are illustrative depictions of variations of a radiotherapy patient platform system.

Some variations of the patient platform, as described in further detail below, may telescope (e.g., portions of the platform may move relative to each other, where one portion of the platform may extend from another portion to make the entire platform longer) to reduce a sag of a patient platform. For example, some patient platforms may be formed of a single piece of carbon fiber cantilevered so as to extend from a base. While these platforms are radiotransparent, they may progressively sag as they extend out from a mounting base and into a patient region of a gantry. As shown in FIG. 1A, for example, a first end (105) of the patient platform (102) will exhibit less sag than a second end (107). In accordance with some of the variations of the invention, a patient platform may comprise a plurality of portions that may move or telescope relative to each other and/or a base of the patient platform. A first portion of the patient platform may be formed of a radiotransparent material while a second portion may be formed of a stiffer material (of any radiotransparency) that exhibits less sag than the first portion. The patient platform may be controlled such that the stiffer second portion is cantilevered from a base and moves right up to, but does not cross the plane of an imaging beam and/or treatment beam that would otherwise interfere with an imaging and/or treatment procedure. Accordingly, the patient platform as a whole may exhibit greater rigidity to reduce sag of the patient platform.

In some variations of the system, as described in further detail below, a patient platform may move with a plurality of degrees of freedom to position a patient and aid delivery of radiotherapy treatment. Some conventional patient platforms provide a motor at each axial end of a patient platform to provide yaw control. These conventional motors may utilize radiopaque wires that extend along a length of the patient platform through a treatment beam plane and undesirably interfere with imaging and/or treatment. By contrast, in some variations of the present invention, a patient platform may comprise a yaw drive and axial drive system coupled to a first end of a patient platform and be configured to yaw about a pivot point without decreasing radiotransparency of the patient platform. In other variations, the patient platform may comprise a vertical drive system configured to control a height and/or pitch of the patient platform that may, for example, be useful for treatment of cranial lesions. In some variations of the methods for delivering radiotherapy treatment, a patient platform may position a region of interest on an isocenter of a gantry such as an isocenter of a beam source to focus radiation dose to the region of interest and reduce radiation dose to healthy tissue.

Described further herein are systems, devices, and method for characterization, qualification, verification, and/or calibration of radiotherapy systems. In order to assess or confirm that the components of the radiotherapy system are configured to deliver a desired radiation dose precisely and accurately to target regions in a patient, the system may undergo quality assurance testing, registration, calibration, and/or verification procedures prior to a treatment session and/or at predetermined intervals (e.g., daily, monthly, quarterly, etc.). Such procedures may comprise measuring the emission or radiation using one or more radiation detectors positioned at predetermined locations. For example, a phantom having a plurality of radiation detectors may be disposed on or below a patient platform. A phantom may comprise a plurality of dosimetry sensors and types configured to receive a dose of radiation. Dose data generated from the phantom may be compared to a set of reference dose data to determine calibration of one or more components (e.g., detector) of the radiotherapy system.

Some variations of the patient platform systems may comprise a handheld controller for controlling a patient platform. Radiotherapy system operators may adjust the position of a patient with respect to a gantry by controlling movement of the patient platform using the handheld controller. For example, one or more switches may be integrated into a housing of the controller for a user to operate. The controller may be docked to a gantry or patient platform to enable a first set of control functionality and undocked from the system to enable a second set of control functionality. The handheld controller, as described in further detail below, may generate a movement signal. Furthermore, control of the patient platform may be limited to a predetermined proximity of the system. Thus, the operator may gain increased mobility while ensuring patient safety and compliance with regulations.

It is generally desirable for a radiotherapy procedure to deliver a treatment beam from a plurality of angles, which may help to reduce radiation dose to healthy tissue. This may be especially desirable for the head and neck as the salivary glands, eyes, ears, and nerve cells may be particularly sensitive to radiation dose. In some variations, a head fixation device may be useful to precisely position a patient's head on a patient platform. However, some patients experience difficulty and/or discomfort with devices that attach to the head and/or control head movement. The head fixation devices, as described in further detail below, may allow a patient to manually move their head through neck flexion to a desired position and lock or secure their head in place for treatment. Additionally or alternatively, a patient and/or operator may control a drive system such as a pneumatic drive system to reposition and lock or secure the head in a desired position. Any of the systems, devices, and methods described below may be used in combination. The variations as described here below may improve patient comfort associated with radiotherapy procedures.

I. Systems

Radiotherapy Patient Platform

Generally, the systems described here may be useful in determining a sag of a patient platform and a location of a region of interest of a patient on the patient platform. FIG. 1A is a cross-sectional side view of a radiotherapy patient platform system (100). The system (100) may comprise a patient platform (102), a gantry (120), and base (112). The patient platform (102) may comprise a radiotransparent first material, such as carbon fiber. The patient platform (102) may further comprise a first side (104) (top surface) comprising a patient support on which a patient (114) may lay on. A second side (106) (underside) of the patient platform (102) may be provided opposite the first side (104). In some variations, the patient platform (102) may have a length of about 1.5-3.0 meters, a width of about 0.50-2.0 meters, and a thickness of about 0.05-0.50 meters, and may preferably have a length of 2 meters, a width of 0.50 meter, and thickness of 0.10 meters. As shown in FIG. 1A, at least a portion of the patient platform (102) may be extended from an edge of a base (112) (e.g., cantilevered) such that a second end (107) of the patient platform (102) may progressively sag due to the weight of the patient (114). In some variations, a radiopaque elongate element (108) may be coupled to the second side (106) of the patient platform (102). The elongate element (108) may be fixed to the patient platform (102) such that an amount of space between the elongate element (108) and patient platform (102) is a constant or a known quantity (e.g., the patient platform (102) and elongate element (108) may be separated by the thickness of a support element (110)). In some instances, a radiotransparent support element (110) may couple the radiopaque elongate element (108) to the patient platform (102). In some variations, the elongate element (108) may have a thickness of about 0.001-0.01 meters and the support element (110) may have a thickness of about 0.001-0.50 meters.

In some variations, the elongate element (108) may be formed of a radiopaque second material. By imaging the elongate element (108) from one or more gantry angles using a first radiation beam (126), a location of the elongate element (108) may be precisely determined. In some instances, the elongate element (108) may comprise a metal such as aluminum, although other radiopaque materials and combinations of radiopaque materials may be used. As shown in FIGS. 1A-1D and 1F, the elongate element (108) may comprise a wire or rod shape. In some variations, a length of the elongate element (108) may correspond to a length of the region of interest (116) of the patient (114). In other variations, the elongate element (108) may correspond to a length of the patient platform (102) through which a first beamlet (127a) may intersect and pass through. It should be noted that any length of the elongate element (108) may be selected so long as the elongate element (108) is located at a position where sag determination is desired. Additionally or alternatively, the radiotransparent support element (110) may couple to one or more radiopaque spheres (e.g., bead, ball, pellet, orb, etc.) in any of the variations described herein.

A first end (105) of the patient platform (102) may be coupled to a base (112). The base (112) may be provided external to a patient region (140) of the gantry (120) and may not be radiotransparent. In the variations depicted in FIGS. 1B-1E, the gantry (120) may comprise a radiation source (122) and a multi-leaf collimator (124) to generate and direct a first beam (126) at the radiopaque elongate element (108) and detector (128) facing the multi-leaf collimator (124). A controller (130) may comprise a processor and memory to determine the sag of the patient platform (102) using the detector data, as described in further detail below. It should be appreciated that the first beam (126) directed at the elongate element (108) may be generated by a radiation source (122) without the multi-leaf collimator (124).

Figure 1B:
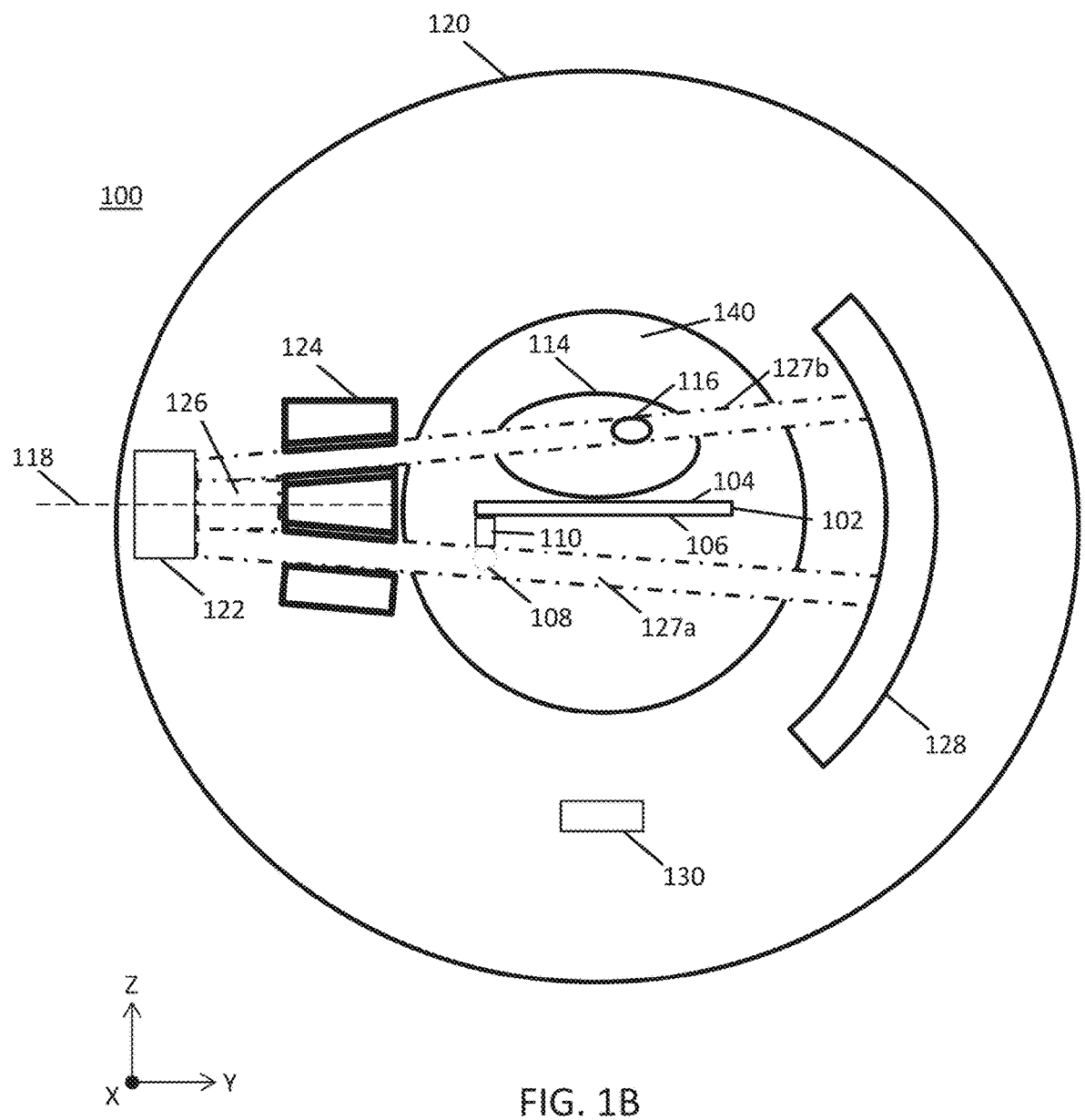
Figure 1C:
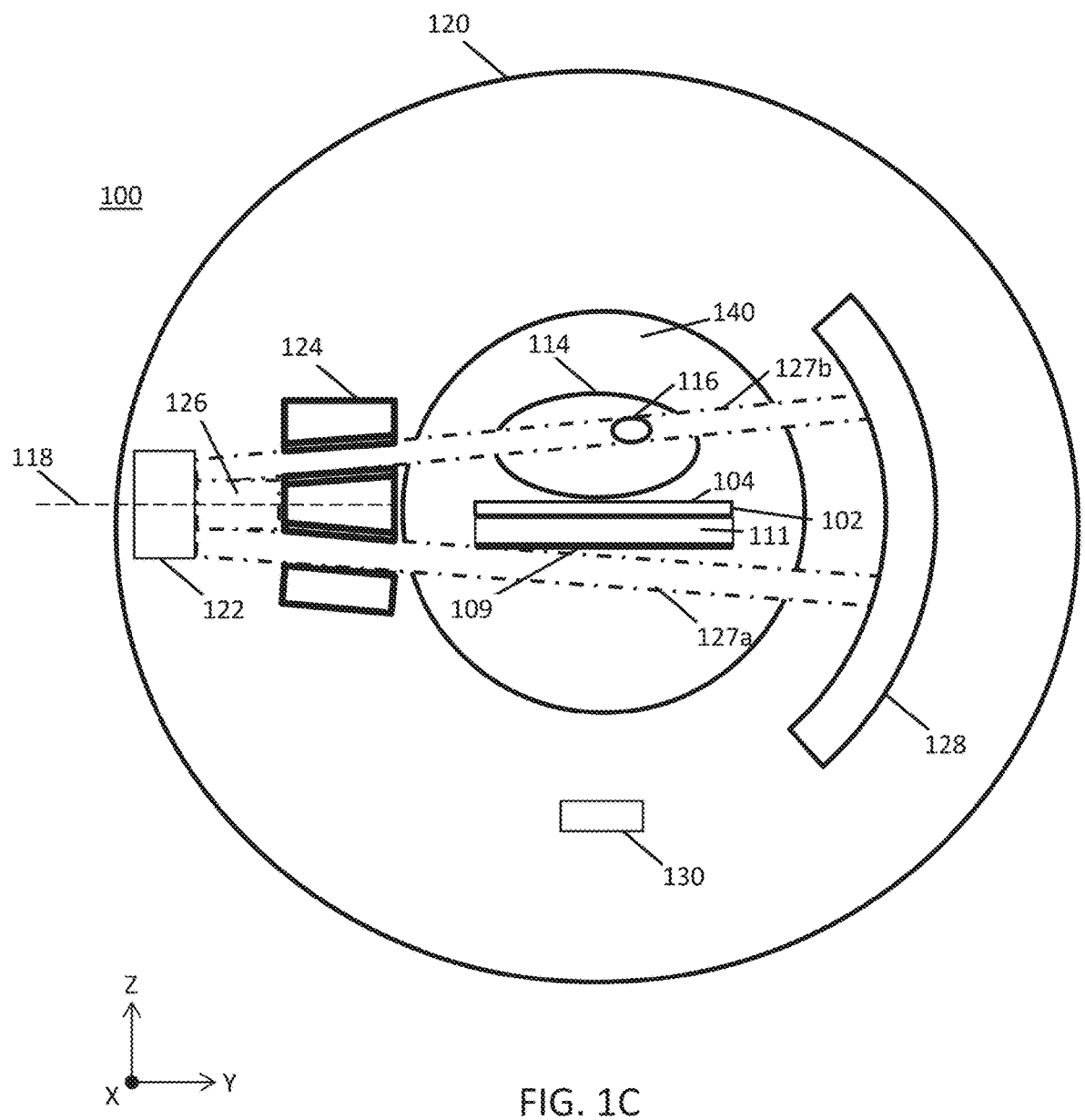

FIG. 1B is a cross-sectional front view of a patient platform (102) and gantry (120) illustrating the intersection of a first beamlet (127a) with the radiopaque elongate element (108) and detector (128). As shown in FIG. 1B, the elongate element (108) may be provided on a second side (106) of the patient platform (102) and coupled to the patient platform (102) by a radiotransparent support element (110). Radiation source (122) may be rotated around the patient region by the gantry (120) such that a first beamlet (127a) and a second beamlet (127b) may be emitted from above, below, and the sides of the patient (114). Although the radiation source (122) may rotate circularly around the patient gantry (120), FIGS. 1B-1C and 1E illustrate the radiation source (122) within the gantry (120) as it is aligned to a horizontal plane (118) (e.g., X-Y plane).

A predetermined estimate of patient platform sag may be used to determine which leaves of the multi-leaf collimator (124) to open to direct the first beamlet (127a) at the radiopaque elongate element (108) and detector (128). For example, estimates of patient platform sag for a given patient weight may be stored in a database in memory and used to determine a set of leaves of the multi-leaf collimator (124) to open for a given gantry angle. The controller (130) controlling the radiation source (118) and multi-leaf collimator (124) may ensure that the first beamlet (127a) does not intersect the patient (114). Optionally, the multi-leaf collimator (124) may open one or more leaves such that a second beamlet (127b) irradiates region of interest (116). Emission of a radiation beam (126) from the radiation source (122) at the gantry angle depicted in FIGS. 1B-1C and 1E may permit the radiation therapy system to provide therapeutic radiation to the region of interest (116) using the second beamlet (127b) while concurrently (e.g., simultaneously or sequentially) collecting image data for patient platform (104) position information (e.g., sag data) using the first beamlet (127a). In FIGS. 1B-1C, the beam (126) emitted from the radiation source (122) through the multi-leaf collimator (124) may select the first beamlet (127a) to intersect the elongate element (108) without intersecting the patient (114). More generally, the first beamlet (127a) may be emitted at the elongate element (108) from any gantry angle so long as the first beamlet (127a) does not intersect the patient (114). Consequently, determination of patient platform sag may not increase radiation dose to the patient (114). In some variations, the first beamlet (127a) may be emitted toward the radiation source (122) relative to the horizontal plane (118) between a first positive rotation angle ($\alpha_1$) and a second negative rotation angle ($\alpha_1$) of about ±45°. The duration and power of the first beamlet (127a) is not particularly limited as the first beamlet (127a) does not intersect the patient (114). Irradiation of the elongate element (108) by the beamlet (127a) may be detected by the detector (128), and this detector data may be used to locate the elongate element (108) of the patient platform (102) weighted by the patient (114) relative to a known location of the elongate element (108) of an unweighted patient platform (102). The difference in these locations corresponds to an amount of sag of the patient platform (102). Detector data generated from a plurality of gantry angles may thus improve real-time sag determination.

It should be appreciated that one or more radiopaque elongate elements (108) may be coupled to the patient platform (102), so long as a first beamlet (127a) that intersects the elongate element (108) does not intersect the patient (114). In some variations, two or more elongate elements (108) may be coupled to the patient platform (102) by respective radiotransparent support elements (110) at a predetermined distance (D) from each other. In some examples, the elongate elements (108) may comprise a pair of cylindrical rods of the same or different dimensions (e.g., length, diameter) provided along different portions of the patient platform (102). In FIG. 1C, one of the elongate elements (108) is disposed on a first side (e.g., left side) of the patient platform (102) while another elongate element (108) is disposed on a second side (e.g., right side) of the patient platform (102). The elongate elements (108) may be disposed in parallel to a longitudinal axis of the patient platform (102). The elongate elements (108) depicted in FIGS. 1C-1D may have the same or different shape and/or dimension. In other variations, three or more radiopaque elements (e.g., elongate elements (108) and/or radiopaque spheres) may be coupled non-collinearly to the patient platform (102). That is, the radiopaque elements may intersect the same line except for at least one of the radiopaque elements. For example, a first and second radiopaque element may be disposed along a line parallel to the Y-axis (e.g., width of the patient platform (102)) while a third radiopaque element may be disposed between the first and second radiopaque element along the Y-axis and spaced apart along the X-axis (e.g., length of the patient platform (102)) from the first and second radiopaque element). In one variation, the three radiopaque elements may comprise any combination of shapes and dimensions as discussed above. For example, the radiopaque elements may comprise three spheres (e.g., beads) or three elongate elements (e.g., rods), two spheres and one rod, and one sphere. The shape, size, dimensions, and locations of the one or more radiopaque elements may be stored in a memory of a controller.

Figure 1D:
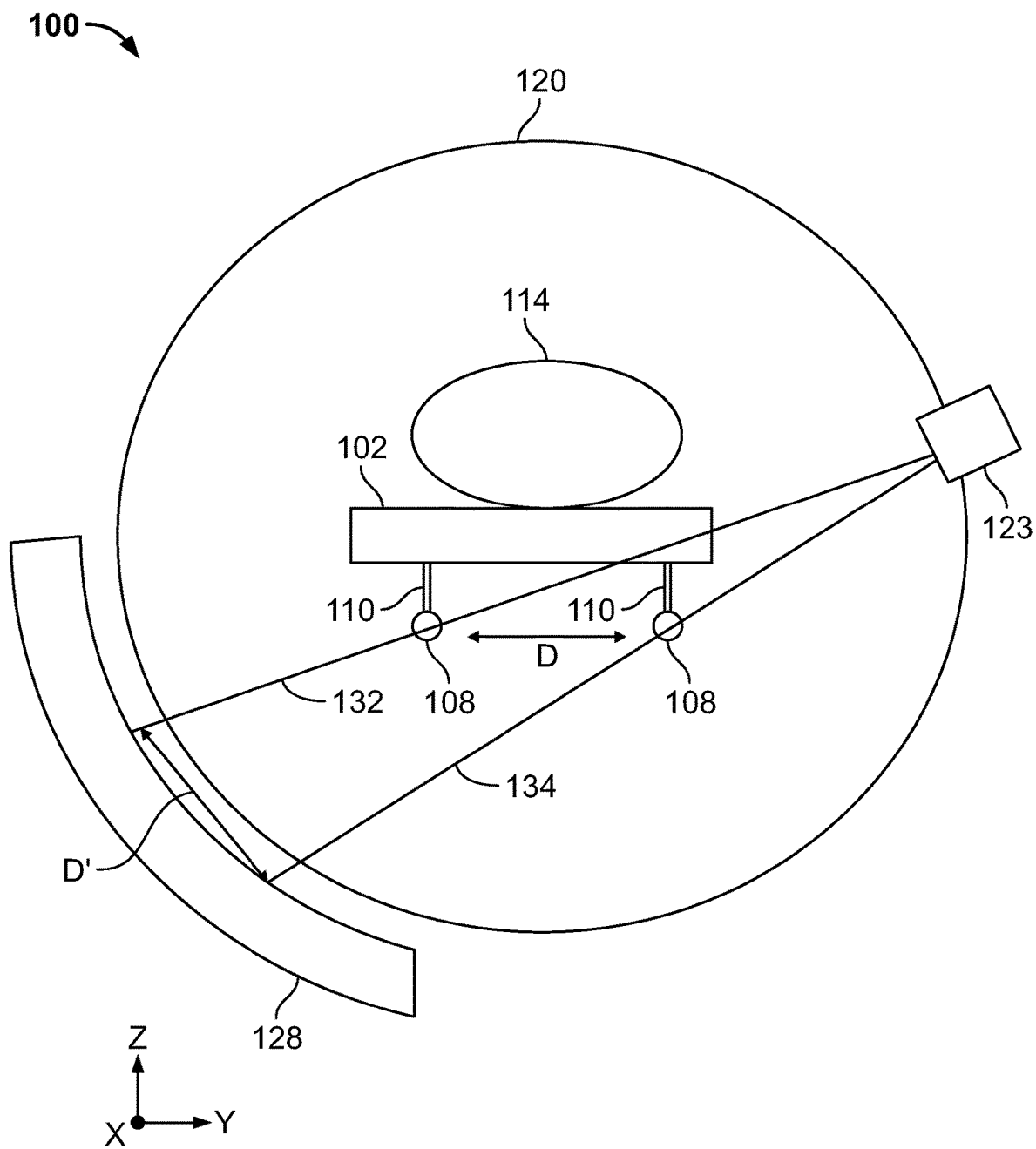
Figure 1E:
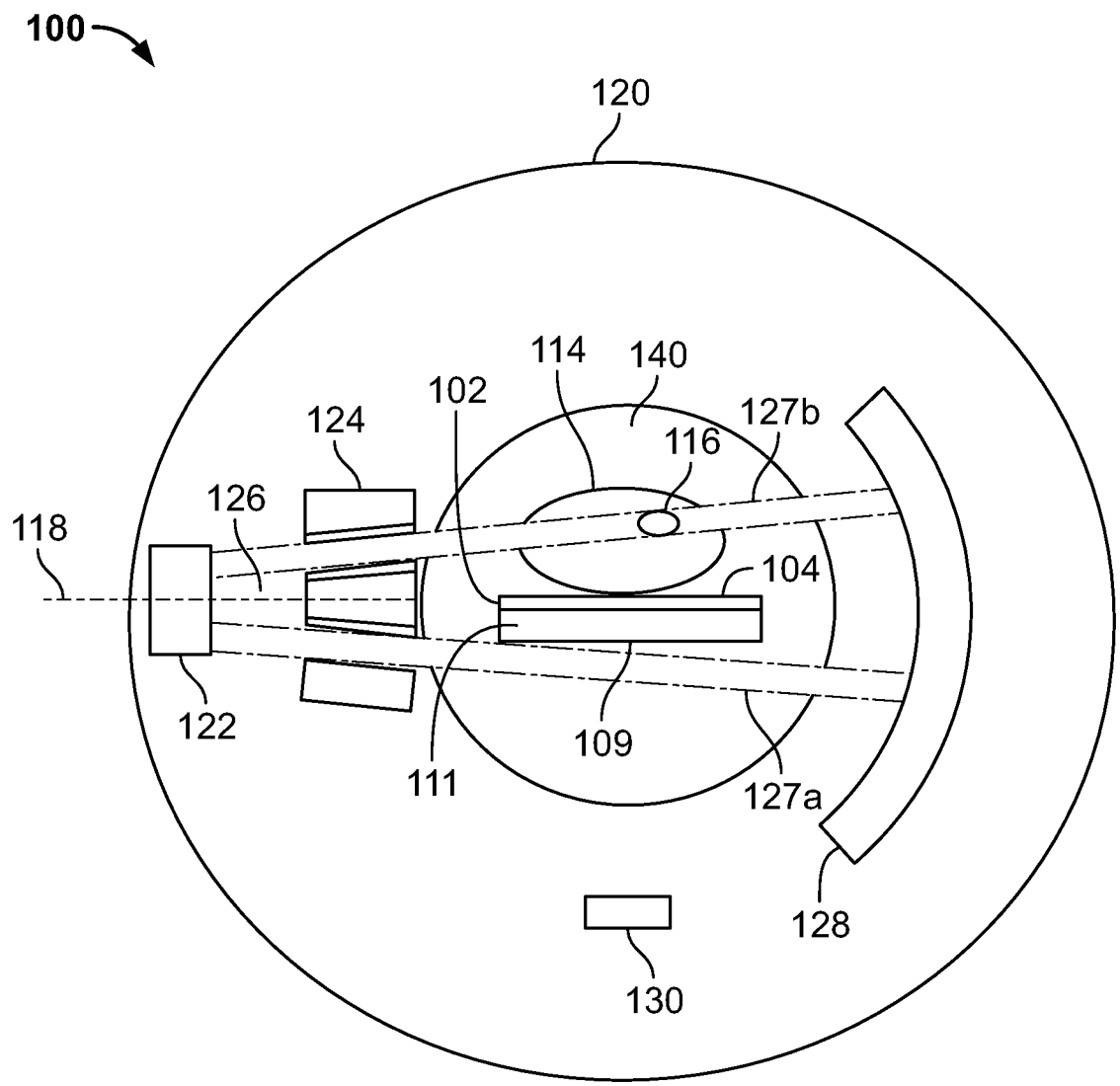

In another variation, as illustrated in FIG. 1D, each elongate element (108) may be imaged using corresponding beamlets (132, 134). Similar to FIG. 1C, the elongate elements (108) may be disposed on opposite sides of the patient platform (102). The beamlets (132, 134) may be emitted from a beam assembly (123) including multi-leaf collimator and radiation source. Imaging of the elongate elements (108) using different beamlets (132, 134) may increase the number of gantry angles from which the elongate elements (108) may be imaged since each beamlet need not intersect both elongate elements (108). In the variation depicted in FIG. 1D, patient platform sag measurements may be acquired without irradiating the patient. This may help to reduce the radiation exposure of the patient.

Both of the elongate elements (108) may be imaged using one or more beamlets at a predetermined gantry angle. The detector data generated by one or more beamlets may be used to determine an amount of patient platform (102) sag. As best illustrated in FIG. 1D, for one or more beamlets (132, 134) emitted at a given gantry angle, the detector (128) will generate detector data having projections of the elongate elements (108) separated by a projection distance (D'). Sag of a patient platform (102) corresponds with the projection distance (D') such that a change in the projection distance (D') indicates a change in the sag of the patient platform (102). For example, an increase in distance (D') may correspond to an increase in sag of the patient platform (102). Thus, patient sag may be determined using one or more beamlets emitted from a single gantry angle. Of course, the elongate elements (108) may be imaged from a plurality of gantry angles to generate detector data.

Additionally or alternatively, the elongate elements (108) may be imaged by beamlets from a plurality of gantry angles to determine an absolute location of the elongate elements (108). For example, a first elongate element disposed on a first side (e.g., left side) of the patient platform (102) may intersect a first beamlet emitted from a first side of the gantry (120) (e.g., left side of FIG. 1C) from a set of angles relative to the horizontal plane (118). Similarly, a second elongate element disposed on a second side (e.g., right side) of the patient platform (102) may intersect a second beamlet emitted from a second side of the gantry (120) (e.g., right side of FIG. 1C) from a set of angles relative to the horizontal plane (118). Thus, the pair of elongate elements may be imaged from left and right sides of the patient platform (102) to increase the number of angles from which the elongate elements may be imaged and thereby improve patient platform sag determination.

In addition to determination of sag, differences in the absolute locations of the elongate elements (108) relative to each other may be used to calculate a roll of the patient platform (102), that is a rotation of the patient platform (102) about a longitudinal axis of the patient platform (102) (e.g., X-axis in FIG. 1C). For example, each of the elongate elements (108) in FIG. 1C may be coupled to the patient platform (102) at equal heights from the second side (106) of the patient platform (102). If the height of one of the elongate elements (108) changes relative to the other elongate element (108), then the patient platform (102) has rolled (e.g., twisted) a corresponding amount. Thus, a change in location of the patient platform (102) due to a patient (114) disposed on the patient platform (102) may be determined along multiple axes.

In another variation, the patient platform (102) may comprise three non-collinear elongate elements (108) used to calculate roll and yaw using the absolute locations of the three elongate elements (108) relative to each other. For example, the three elongate elements (108) may be coupled to the patient platform (102) spaced apart along the X-axis and Y-axis of the patient platform (102). If the detector data projections of the elongate elements (108) along the X-axis change in distance, then the patient platform (102) has yawed (e.g., turned) a corresponding amount. Thus, a sag, roll, and yaw of the patient platform (102) due to a patient (114) may be determined using a set of elongate elements (108) and at least two beamlets.

FIG. 1E is another cross-sectional front view of a patient platform (102) and gantry (120) illustrating the intersection of a first beamlet (127a) with a radiopaque elongate element (109) that extends in a widthwise direction. This configuration may allow imaging from opposite sides of the gantry (120) (e.g., left and right sides of a patient (114)). As shown in FIG. 1E, the radiopaque elongate element (109) may comprise a thin metallic foil (e.g., a metal sheet). A thin, wide foil having a width greater than thickness may provide significant attenuation only in the direction along the width of the foil (e.g., along the plane of the metal sheet) such that the foil does not significantly attenuate imaging beams at other angles. In some instances, the elongate element (109) may comprise aluminum and have a thickness of about 0.0001-0.001 meters and a width of about 0.10-0.5 meters.

In some variations, the elongate element (108, 109) may comprise a plurality of materials and configurations. For instance, the elongate element (108, 109) may form a radiotransparent portion and one or more radiopaque portions where the radiopaque portions may form identifiable shapes after image processing. In some instances, the imaged radiopaque elongate element (108, 109) may display one or more symbols (e.g., numbers, letters), geometric shapes, and other fiducials corresponding to predetermined locations along a length of the patient platform (102) that may aid patient platform sag determination.

In some variations, the patient platform (102) may comprise one or more radiopaque portions without coupling to an elongate element (108, 109) and/or radiotransparent support element (110). For instance, a radiopaque portion may be coupled to an edge of the patient platform (102) by a fastener, adhesive, and the like.

Additionally or alternatively, the elongate element may not be radiopaque so long as an image contrast may be formed with the patient platform. It should be appreciated that any material able to generate an image contrast with respect to the radiotransparent patient platform (102) may be used. In some variations, the patient platform (102) may comprise a plurality of bores (e.g., elongate holes) for detecting sag of a patient platform (102). For example, a radiotransparent support element (110) may couple to a second side (106) of the patient platform (102) and comprise one or more bores that allow portions of a radiation beam (126) to pass through unimpeded and be received by a detector (128). A bore may, for example, extend in a longitudinal direction (e.g., along the X-axis) as an elongate bore or have a spherical shape. In another example, the support element (110) may comprise aluminum to enhance an image contrast between the empty space within the bore and the support element (110). It should be appreciated that the shape of the bore is not limited so long as the detector data of the bore may be used to determine a location of the patient platform (102). For example, a bore may comprise a rod shape or a spherical shape as discussed above. In some variations, a length of the bore may correspond to a length of the region of interest (116) of the patient (114). In other variations, the bore may correspond to a length of the patient platform (102) through which a first beamlet (127a) may intersect and pass through.

The bore may comprise a plurality of shapes and sizes, as discussed above. In some instances, the bore may have a diameter of about 0.001-0.01 meters. Although the support element (110) and patient platform (102) may be radiotransparent, a faint outline of the support element (110) and patient platform (102) may still be visible when imaging the platform (102) such that an image contrast between a solid portion of the patient platform (102) and one or more bores within the support element (110) and/or patient platform (102) may serve as a fiducial for location tracking. Detector data may be used to locate one or more bores of the support element (110) and/or patient platform (102) relative to a known location. The difference in these locations corresponds to an amount of sag of the patient platform (102). In this manner, sag of the patient platform (102) may be determined without the artifacts associated with high density, radiopaque materials.

Figure 1F:
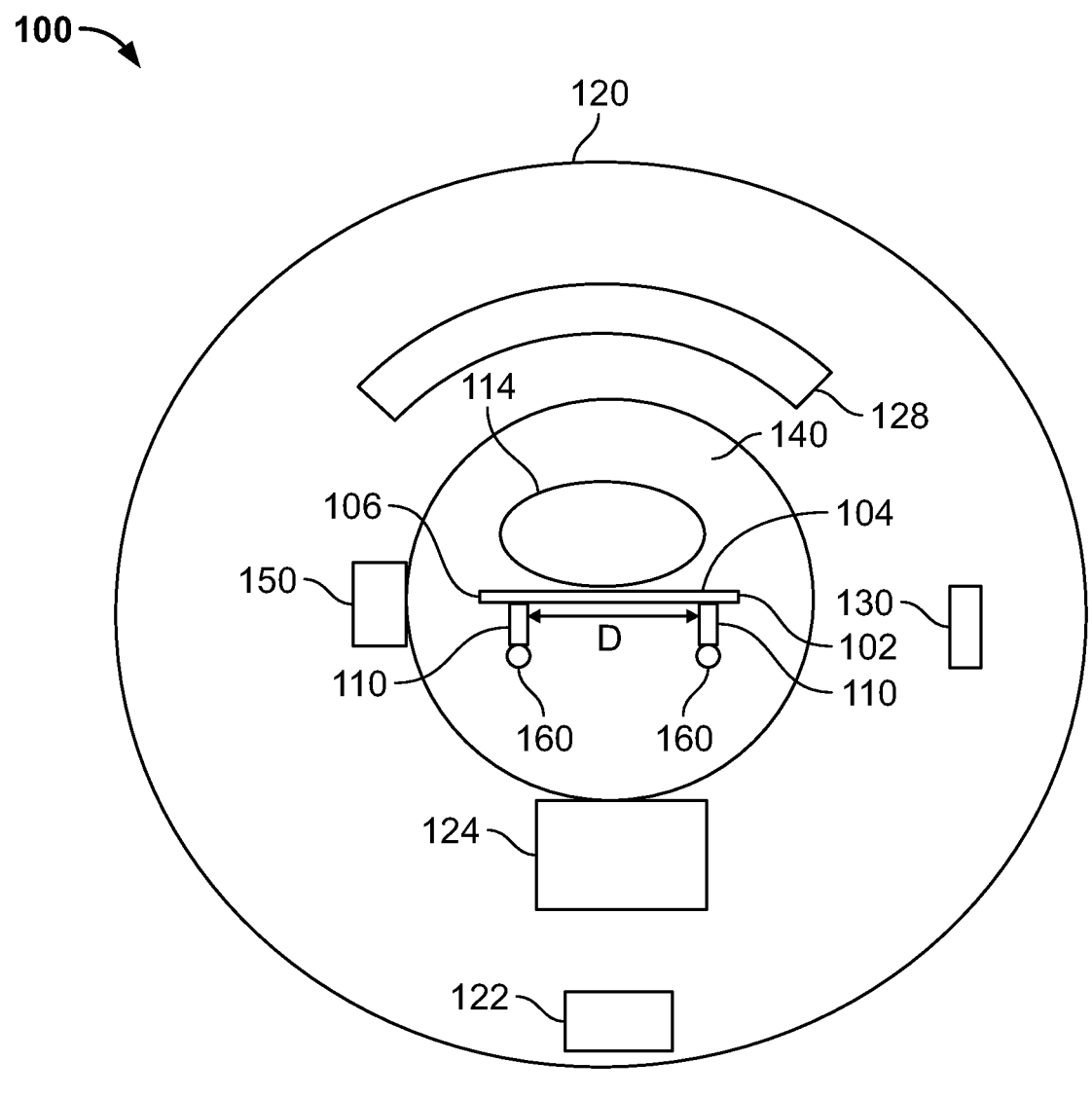

FIG. 1F is cross-sectional front view of a patient platform (102) and gantry (120) comprising an optical sensor (150) configured to image one or more optical markers (160) coupled to a patient platform (102). The optical sensor (150) may be coupled to the gantry (120) such that the optical sensor (150) rotates with the gantry (120) about the patient (114) in the patient region (140). As the gantry (120) rotates, the optical sensor (150) may image one or more optical markers (160) from one or more gantry angles (e.g., from the sides and from below the patient (114)). The imaging data generated by the optical sensor (150) may be used to locate the optical marker (160) of the patient platform (102) weighted by the patient (114) relative to a reference location of the optical marker (160) of an unweighted patient platform (102). The difference in these locations corresponds to an amount of sag of the patient platform (102). Imaging of two or more optical markers (160) may allow the controller to determine one or more of sag, roll, and yaw of the patient platform (102) in a similar manner as discussed above with respect to the elongate elements (108).

The optical marker (160) may be imaged by the optical sensor (150) to generate optical marker (160) data having high contrast relative to other imaged elements within a bore (140) of the gantry (120) including the patient platform (102), patient (114), patient support element (110), and gantry housing. The image contrast allows the optical marker (160) to be spatially separated from other imaged elements such as the patient platform (102) and the patient (114). The optical marker (160) may provide high contrast sensor data within one or more wavelength ranges of the light spectrum (e.g., visible wavelengths, infrared wavelengths, ultra-violet wavelengths). In some variations, the optical marker (160) may comprise a reflector configured to generate a high contrast image using the optical sensor (150). For example, one or more optical markers (160) may comprise a material and/or structure to reflect light back to the optical sensor (160) with a minimum of scattering (e.g., retroreflector). The optical marker (160) may comprise, for example, a mirror (e.g., for reflecting light from an illumination source such as a laser) or a high contrast color surface. The optical markers (160) may have the same size, shape, number, and location of the radiopaque elements (e.g., elongate elements, sphere) discussed above. For example, one or more optical markers (160) may be coupled to the patient platform (102) and each optical marker (160) may comprise a rod or spherical shape. The optical marker (160) may be located along a longitudinal axis parallel to a longitudinal axis of the patient platform (160).

Imaging of the optical markers (160) using an optical sensor (150) may provide sag determination without emission of additional beamlets (127a) from the radiation source (122) as illustrated in FIGS. 1B-1E. Sag determination using the optical sensor (150) and optical markers (160) may be performed concurrently with radiation therapy treatment using the radiation source (122) and multi-leaf collimator (124). In some variations, the optical sensor (150) may comprise an infrared light sensor and may further comprise an illumination source to enhance an amount of reflected light received from the optical marker (160). In some of these variations, the optical sensor (150) may comprise a filter to reduce infrared data from the patient (114) and/or other non-retroreflective sources (160). In other variations, the optical sensor (150) may comprise a visible light sensor (e.g., charge-coupled device (CCD), active-pixel sensor (APS)) and may further comprise a visible light illumination source. In yet other variations, the optical sensor (150) may comprise an ultra-violet light sensor and may further comprise an ultra-violet light illumination source. In some other variations, the optical sensor (150) may comprise a time of flight rangefinder including a laser for locating one or more optical marker (160). In other variations, the optical sensor (150) may image the patient (114) as the gantry (120) rotates to monitor a condition of the patient (114).

In some non-limiting, exemplary variations, the patient platform (102) may have a weight capacity of about 210 kilograms and have an extension length from an end of the base (112) of about 2 meters. The sag of patient platform (102) in some instances may be several centimeters, and will vary based on patient characteristics such as patient weight and positioning, as well as patient platform material and design.

Conformable Patient Platform

Generally, the patient platform devices described here may provide a conformable support for a patient in imaging and/or radiotherapy procedures. In particular, the shape of the patient platform may be personalized for each patient to reduce patient movement and motion artifacts during treatment and to improve patient comfort. For instance, the patient may be loaded and located outside of a gantry on the patient platform in a patient registration process, thereby reducing setup time of the patient platform within the gantry. This may allow more efficient scheduling of a radiotherapy system and allow more patients to receive treatment from a radiotherapy system.

Figure 2A:
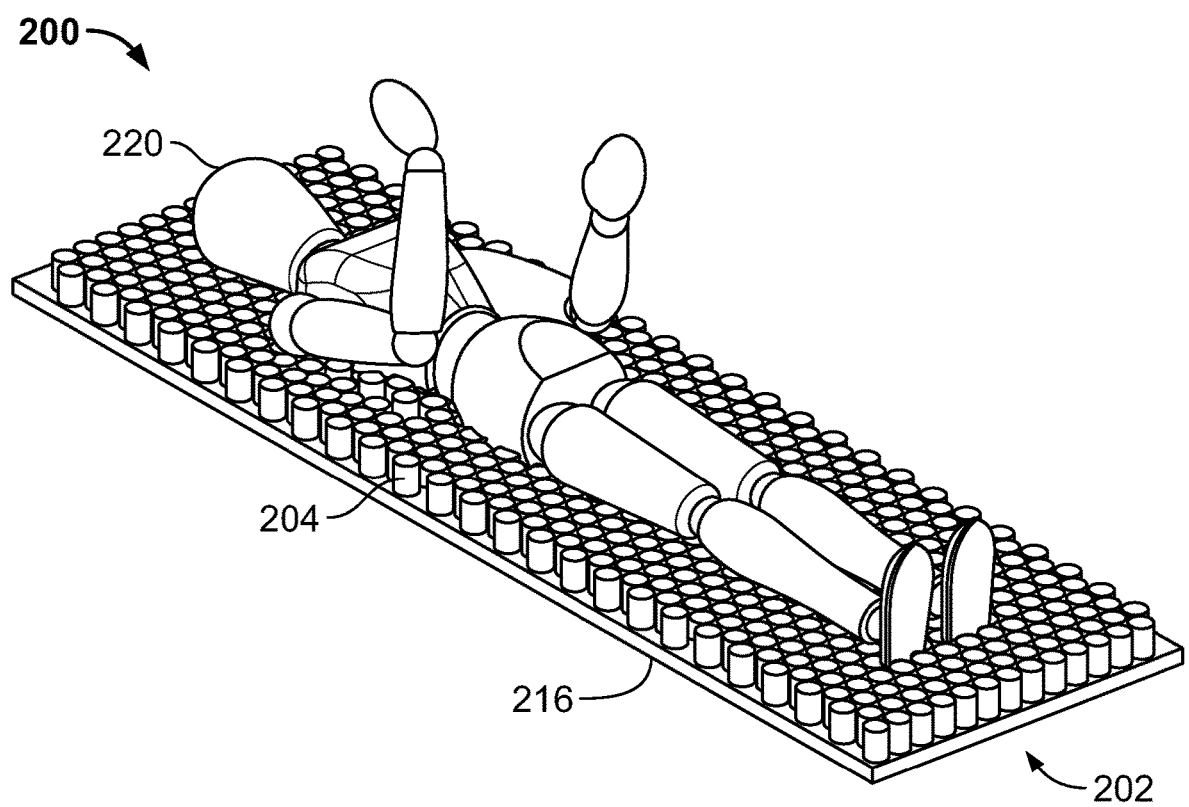
FIGS. 2A-2C are illustrative depictions of variations of a radiotherapy patient platform.
Figure 2B:
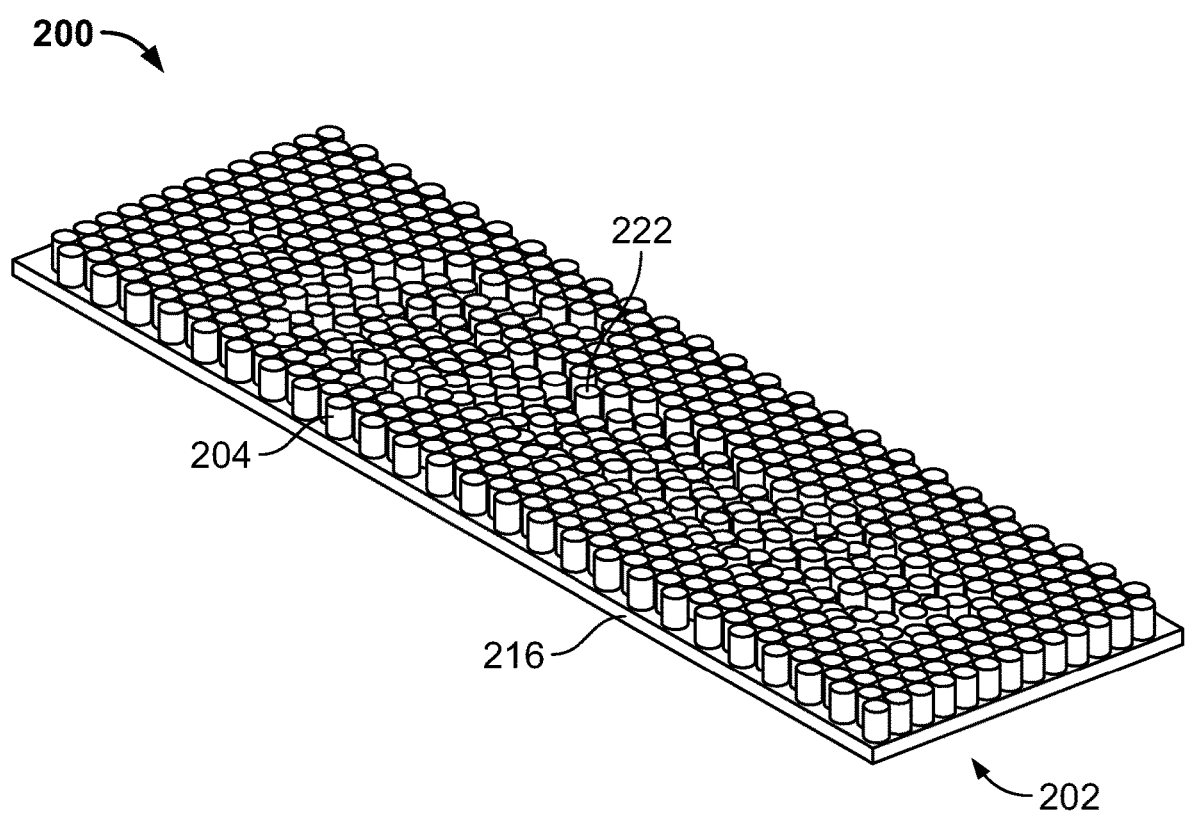

FIG. 2A is a perspective view of a variation of a conformable radiotransparent patient platform (200) comprising a conformable substrate (202) having a rigid base (216) coupled to a plurality of enclosures (204). A patient (220) is depicted on the patient platform (200). It should be appreciated that the patient (220) may typically have their arms at their sides during an imaging and/or treatment procedure. The height of each of the plurality of enclosures (204) may be independently pressure controlled by a controller coupled to a pressure source (e.g., gas, liquid) (not shown in FIGS. 2A-2B). The base (216) and enclosures (204) may be radiotransparent such that they do not interfere with imaging and/or radiotherapy procedures. As shown in FIG. 2A, the enclosures (204) may be airtight and expandable such that a pressure and rigidity of the enclosures (204) may be adjustable to comfortably and securely constrain the patient (220). FIG. 2B is a perspective view of the conformable patient platform (200) with the patient removed to illustrate a patient contour (222).

In some variations, the enclosures (204) may comprise polyurethane and/or other low-Z material bags or balloons that may be filled with fluid including gas and/or liquid. In other variations, the enclosures (204) may comprise a flexible membrane. In some variations, the enclosure (204) may have a diameter from about 0.001-0.050 meters, and a fully-pressurized height from about 0.01-0.30 meters. For example, the enclosure (204) may have a diameter of about 0.05 meters, and a fully-pressurized height of about 0.15 meters. As shown in FIGS. 2A-2B, the plurality of enclosures (204) may be cylindrical and provided in a staggered array configuration. In some variations, the plurality of enclosures (204) may comprise a honeycomb configuration.

For an unweighted conformable substrate (202) (e.g., a conformable substrate (202) without a patient (220) or load applied to the enclosures (204)), the enclosures (204) may be set to a predetermined pressure such that the enclosures (204) may comprise the same or different heights. For instance, the height of the enclosures (204) along the edges of the platform (200) may be higher than other portions to form a curve on a surface of the patient platform (200). This may encourage a patient (220) to position themselves at a center of the patient platform (200) or to place their heads at a predetermined region. In other variations, the heights of the enclosures (204) of a patient platform (200) may progressively change in order to compensate for anticipated sag of the weighted patient platform (200). For example, an average height of the enclosures extending from a base of the platform may increase along a longitudinal axis of the patient platform.

The number of enclosures (204) is not particularly limited, so long as the patient (220) loaded on the platform (200) is stable and able to maintain a constrained position. In some variations, the size and density of the enclosures (204) may vary over different portions of the conformable substrate (202). For instance, a lower density of larger diameter enclosures (204) may be provided along the outer edges of the substrate (202) while a higher density of smaller diameter enclosures (204) may be provided for a patient head and torso area. In some of these instances, a third size of the enclosure (204) may be provided for a patient limb area. In this manner, the number of enclosures may be selected to optimize patient ergonomics. In some variations, other radiotransparent support elements (e.g., cushions, pads, pillows) may be coupled to the substrate (202) to aid patient comfort and to further secure the patient (220) in place on the patient platform (200).

Figure 2C:
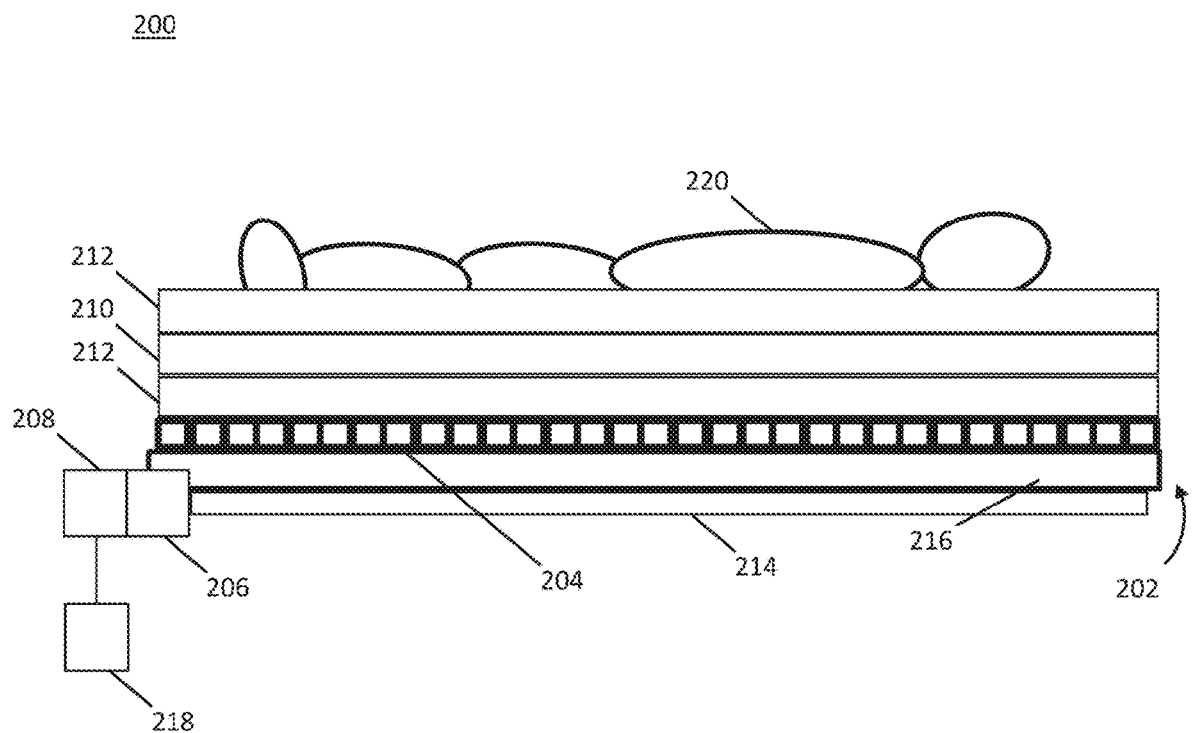

Additionally or alternatively, FIG. 2C illustrates a cross-sectional side view of a conformable patient platform (200) comprising a conformable substrate (202) and a thermoelectric layer (210) having a heating element. In some variations, the heating element may comprise a set of very thin wires, such as having a human hair thickness. The conformable substrate (202) may further comprise a pressure sensor (206) coupled to the conformable substrate (202) and configured to measure a pressure of the conformable substrate (202). For instance, the pressure sensor (206) may be configured to measure a plurality of enclosure (204) pressures. A pressure source (208) may be coupled to each of the plurality of enclosures (204) of the conformable substrate (202) via a pressure channel (214). The pressure channel (214) may comprise a radiotransparent material and may, for example, comprise a plurality of tubes coupled to corresponding enclosures (204) through the base (216). In some variations, the pressure source (208) may comprise one or more of a pneumatic source (e.g., compressed gas). As discussed in further detail below, the controller (218) may independently control a height of each of the plurality of enclosures (204) using the pressure sensor (206) and pressure source (208).

The thermoelectric layer (210) may be provided between the patient (220) and plurality of enclosures (204). In some variations, the thermoelectric layer (210) may be about 1.0-5.0 mm thick, and for example, about 2.0-3.0 mm thick. One or more thermoinsulating layers (212) may be provided above and/or below the thermoelectric layer (210) to insulate either the patient (220) and/or conformable substrate (202) from heat generated by the thermoelectric layer (210). In some variations, the thermoinsulating layer (212) may be about 1.0-15.0 mm thick. In some instances, the thermoinsulating layer (212) may be about 5.0-10.0 mm thick. Heating of the thermoelectric layer (210) may transition the thermoelectric layer (210) into a compliant configuration based on temperature. In some variations, the thermoelectric layer (210) may transition into the compliant configuration at about 80° C. In some variations, the thermoelectric layer (210) may be heated through electric current provided by an electrical conductor (e.g., metal wires) coupled to the thermoelectric layer (210). In some instances, the thermoelectric layer (210) may reach the compliant configuration in about a minute. The compliant configuration may be pliable to conform to a patient's body shape and the rigid configuration may fix the shape and contour of the thermoelectric layer (210). In some variations, one or more of the thermoelectric layer (210) and thermoinsulating layer (212) may comprise a cooling element to cool and rigidize the thermoelectric layer (210) after a patient (220) has adjusted the patient platform (200) to a desired level of comfort. For example, a cooling element may comprise a lumen (e.g., a channel) through which a fluid (e.g., air, water) may travel through to cool the thermoelectric layer (210). In some variations, the thermoelectric layer (210) may not span across the entire surface area of the patient platform (202) and may comprise a patient body outline.

One variation of a patient platform adjustment process using the patient platform (200) of FIG. 2C may include the step of filling the plurality of enclosures (204) to a set of predetermined pressures based on a previously determined patient configuration. In some variations, the set of pressures may be between about 1-2 atm. The thermoelectric layer (210) may be heated to form a compliant configuration that may conform to a patient's body (e.g., a load applied to the enclosures). A patient (220) may then lay onto the patient platform (200) where the heights of the enclosures (204) may equalize and the conformable substrate (202) may conform to the patient (220).

Thereafter, the height of each of the plurality of enclosures (204) may be adjusted for patient comfort by increasing or decreasing pressure from the pressure source (208) using the controller (218). The heating element may be deactivated so that the thermoelectric layer (210) cools down to form a rigid configuration that may comfortably and securely constrain the patient (220) generally in less than 60 seconds. In some of these variations, a cooling element of one or more of the thermoelectric layer (210) and thermo-insulating layer (212) may be activated to more quickly transition the thermoelectric layer from the complaint configuration to the rigid configuration.

Once a desired shape of the patient platform (200) has been achieved, the controller (218) may store a patient configuration in memory, when the patient configuration comprises at least one of the pressure and/or height of each of the plurality of enclosures (204). Accordingly, individualized patient configurations may be provided for each patient (220) to reduce the setup time of patient registration and increase imaging and/or treatment consistency. Furthermore, the patient configuration may be transferable between patient platforms of different radiotherapy systems to increase the consistency of patient positioning in imaging and/or treatment procedures across various systems. It should be appreciated that the patient platforms (200) discussed herein may be particularly useful for improving ergonomics and compliance for radiation therapy procedures requiring more time and/or higher dose accuracy.

In some non-limiting, exemplary variations, the enclosures (204) may comprise one or more shapes including a cylinder, cuboid, triangular prism, hexagonal prism, polygonal prism, and the like. In some variations, different fluids (e.g., gas, liquids) and combinations of fluids may be used to fill different sets of enclosures (204).

Although FIG. 2C illustrates the thermoelectric layer (210) and enclosures (204), the conformable substrate (202) may comprise the thermoelectric layer (210) without the enclosures (204) or the enclosures (204) without the thermoelectric layer (210).

Telescoping Patient Platform

Generally, the patient platform devices described here may be configured to coordinate movement of a patient platform with emission of imaging and/or treatment beams. For example, the movement and positioning of a rigid lower portion of the patient platform may be controlled to avoid intersection with an imaging and/or treatment beam. Meanwhile, a radiotransparent upper portion of the patient platform may be controlled to intersect the imaging and/or treatment beam. This spatial and temporal control of the patient platform and beam(s) may allow movement of the rigid portion into a patient region of the gantry without negatively impacting or otherwise interfering with an imaging and/or treatment beam. Accordingly, a length of a radiotransparent portion may be reduced such that patient platform sag may be reduced. As discussed in further detail below, the rigid lower portion and radiotransparent upper portions of the patient platform may either move relative to each other (FIGS. 3A-3B) or maintain their positions relative to each other (FIGS. 3C-3D).

Figure 3A:
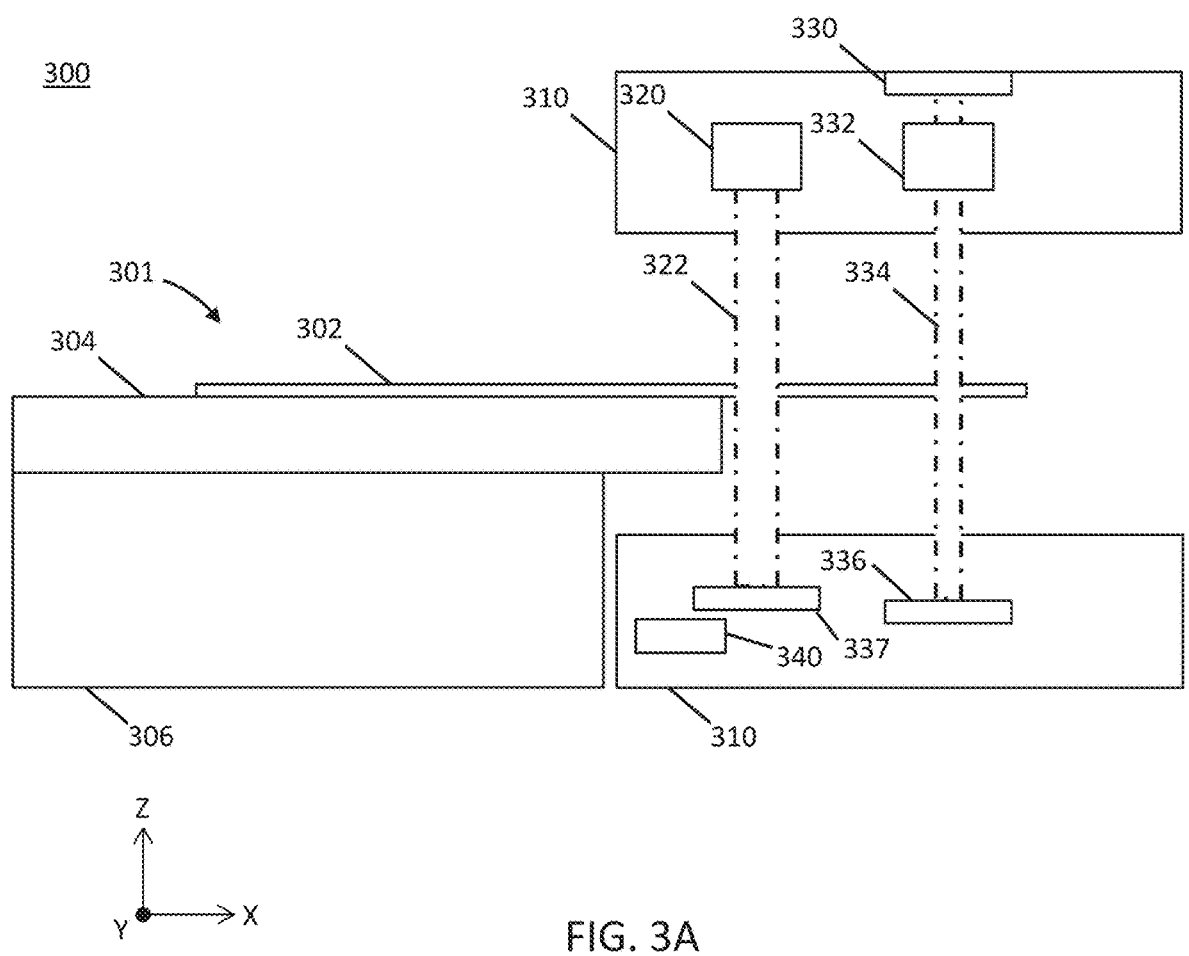
FIGS. 3A-3D are illustrative depictions of variations of a radiotherapy patient platform system.
Figure 3B:
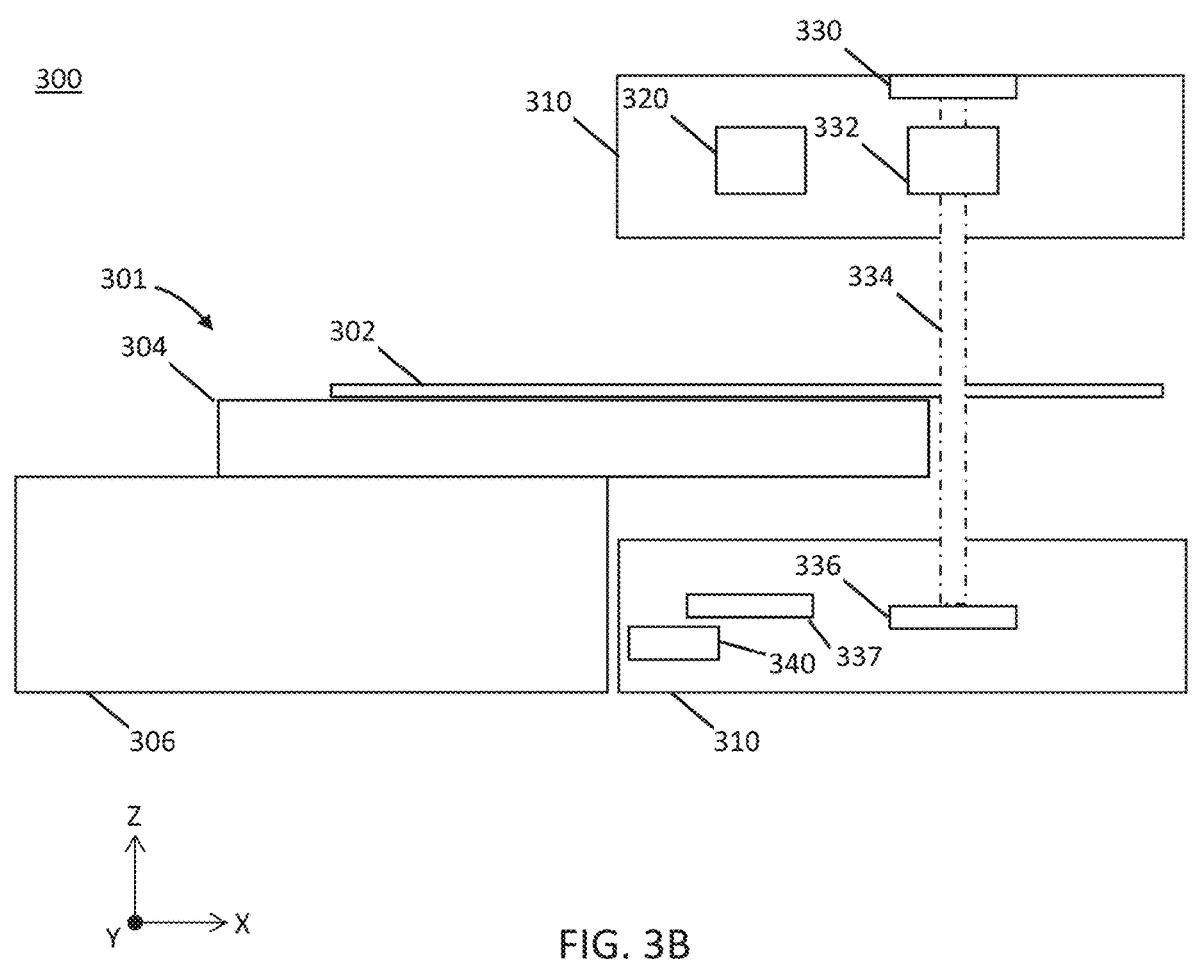
Figure 3C:
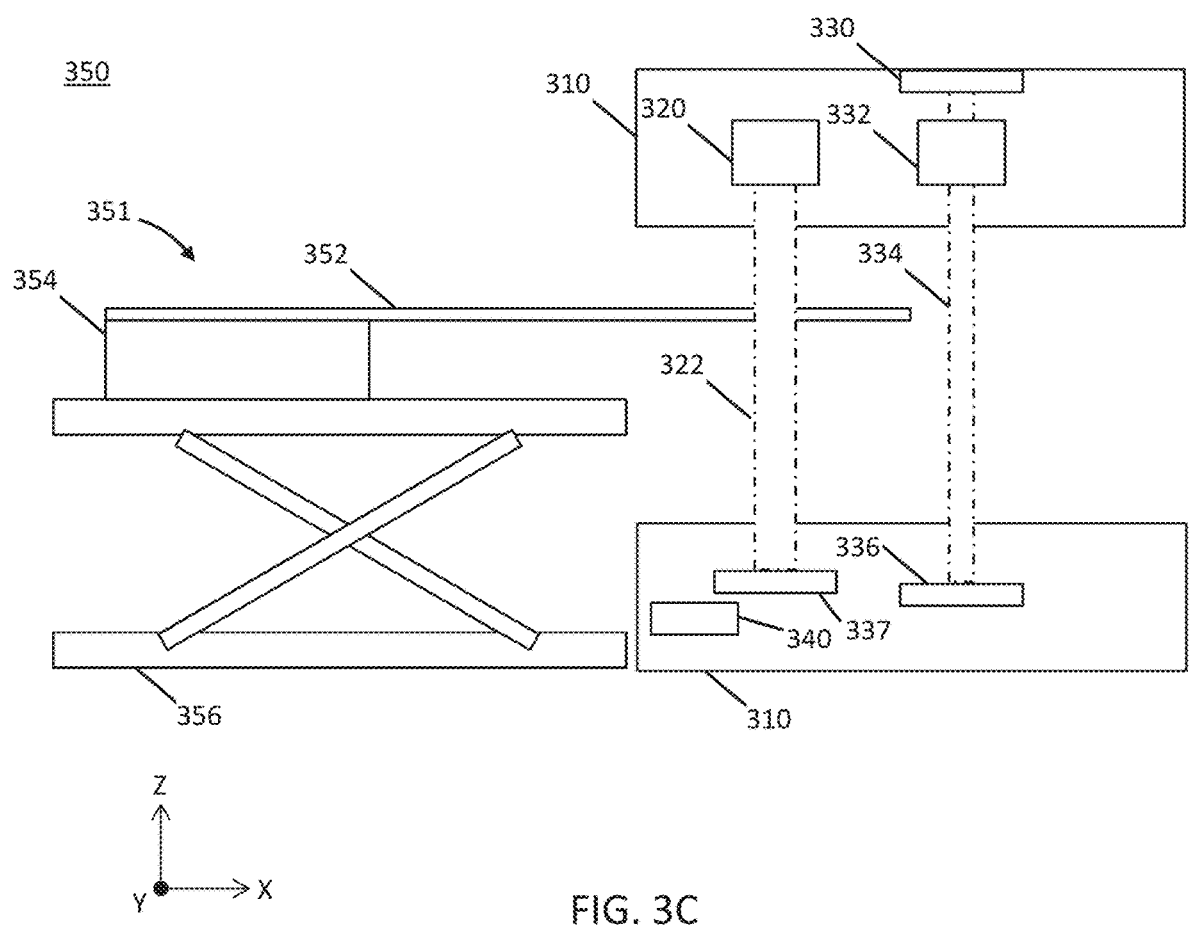
Figure 3D:
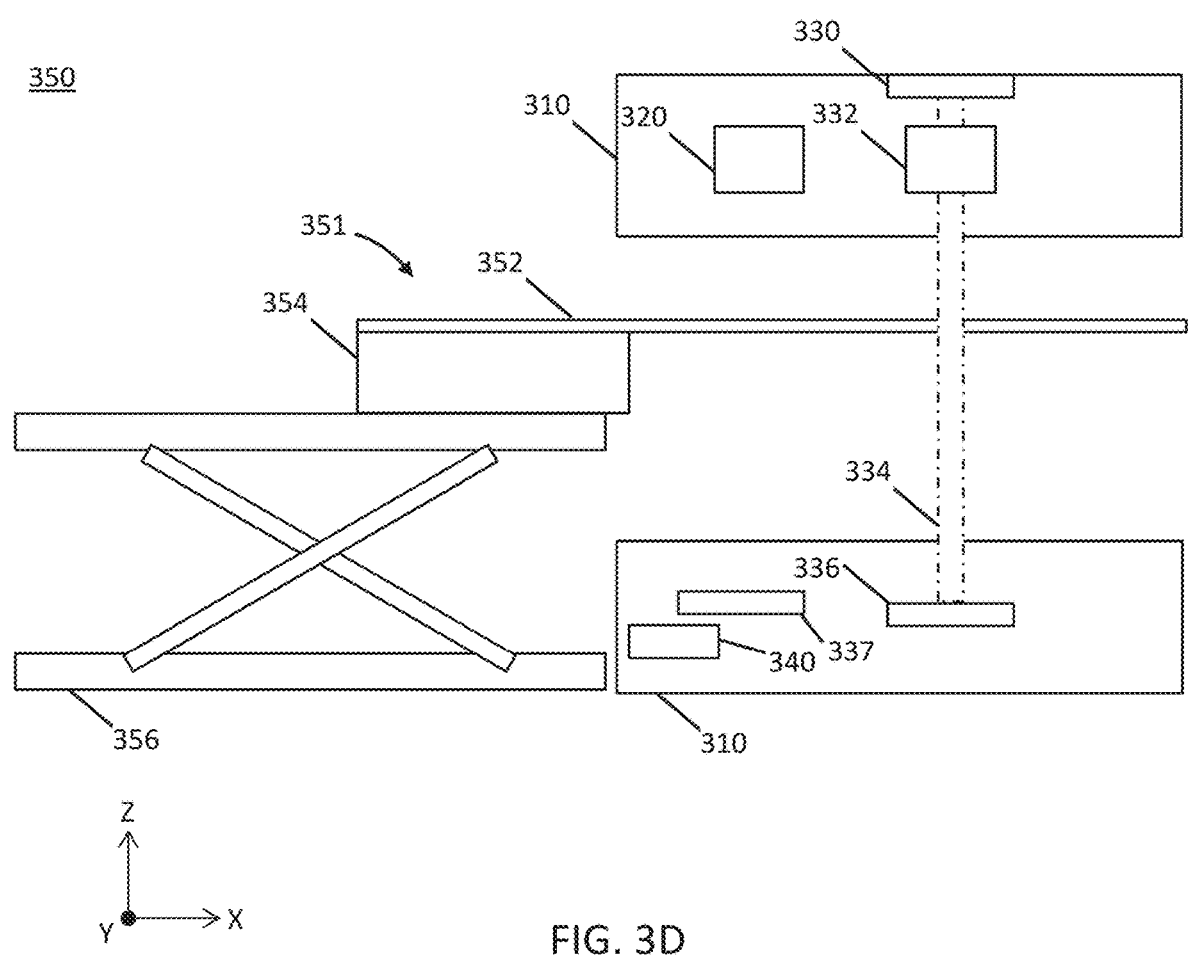

In one variation, FIGS. 3A-3B illustrate a patient platform (301) having a rigid portion and a radiotransparent portion that may move relative to each other. FIGS. 3A-3B are cross-sectional side views of a telescoping patient platform system (300). The system (300) may comprise a patient platform (301) having an upper portion (302) coupled to a lower portion (304). The upper portion (302) may be configured to move axially along the X-axis relative to the lower portion (304). In some variations, the upper portion (302) may be radiotransparent and the lower portion (304) may be radiopaque. A base (306) may be coupled to the lower portion (304) of the patient platform (301). The lower portion (304) may be configured to move relative to the base (306). Accordingly, the patient platform (301) may telescope axially as it is extended into and out of a patient region of a gantry (310). In some variations, the upper portion (302) may comprise a set of rails coupled to a drive mechanism (e.g., single motor) configured to move the upper portion (302) relative to the lower portion (304). Similarly, the lower portion (304) may comprise a set of rails coupled to a drive mechanism configured to move the lower portion (304) relative to the base (306).

In some variations, the upper portion (302) and lower portion (304) may have different radiotransparency. For instance, the upper portion (302) may be radiotransparent and less rigid relative to the lower portion (304) that may be radiopaque and have more rigidity.

The system (300) may further comprise a gantry (310) having an imaging radiation source (320) and a treatment radiation source (330). For example, the imaging radiation source (320) may be a kV radiation source and the treatment radiation source (330) may be a MV radiation source. The treatment radiation source (330) may be coupled to a multi-leaf collimator (332) and may be located opposite a detector (336). The treatment radiation source (330) may be configured to emit a treatment beam (334) in a treatment beam plane perpendicular to a longitudinal axis of the patient platform (301). The imaging radiation source (320) may be configured to emit an imaging beam (322) in an imaging beam plane perpendicular to a longitudinal axis of the patient platform (301), where transmission of the imaging beam (322) through the patient may be detected by an imaging detector (337). Although FIG. 3A depicts both the imaging beam (322) and the treatment beam (334) as being emitted simultaneously, thereby treating one region of the patient while imaging another region of the patient, it should be understood that each of these beams may be activated sequentially or separately. That is, imaging of the patient using the imaging beam (322) need not take place while the patient is being treated with the treatment beam (334) (e.g., the imaging beam (332) and the treatment beam (334) are not activated at the same time).

With respect to an imaging procedure, the system (300) may be in an imaging configuration, an example of which is depicted in FIG. 3A. As shown there, a controller (340) may be configured to move the rigid lower portion (304) (that may be radiopaque) as close to the imaging beam (322) as possible without intersecting the imaging beam (322). A leading edge of the lower portion (304) may be separated by a first distance from a plane of the imaging beam (322). In some variations, the first distance may be about 2 centimeters. In this manner, the stiffer portion of the patient platform (301) may be moved as close as possible to the imaging beam (322) without interfering with the imaging beam (322). The upper portion (302) may be moved (telescoped) freely in an axial direction relative to the lower portion (304) to intersect the imaging beam (322) and image a desired region the patient (not shown).

As shown in FIG. 3A, a controller (340) of the system (300) may be configured to move the upper portion (302) and lower portion (304) such that the lower portion (304) is non-intersecting with the imaging plane of the imaging beam (322) and the upper portion (302) intersects the imaging plane of the imaging beam (322). In this manner, only the radiotransparent upper portion (302) intersects the imaging beam (322).

With respect to a radiotherapy procedure, the system (300) may be disposed in a treatment configuration, an example of which is depicted in FIG. 3B. As shown there, the controller (340) may be configured to move the rigid lower portion (304) (that may be radiopaque) as close to the treatment beam (334) as possible without intersecting the treatment beam (334). In this manner, the stiffer portion of the patient platform (301) may be moved as close as possible to the treatment beam (334) without interfering with the treatment beam (334). In some variations, the lower portion (304) may be positioned (e.g., by a drive mechanism) such that a leading edge of the lower portion (304) may be located at a predetermined second distance away from the treatment plane (FIG. 3B). For example, the second distance may be about 2 centimeters. The upper portion (302) may be moved (telescoped) freely in an axial direction relative to the lower portion (304) to intersect the treatment beam (334) and treat the patient (not shown). In the treatment configuration depicted in FIG. 3B, the imaging radiation source (320) may not be activated because the rigid lower portion (304) (that may be radiopaque) is located in the beam path of the imaging radiation source (320).

As shown in FIG. 3B, a controller (340) of the system (300) may be configured to move the upper portion (302) and lower portion (304) (e.g., by a drive mechanism) such that the lower portion (304) is non-intersecting with the treatment plane of the treatment beam (334) and the upper portion (302) intersects the treatment plane of the treatment beam (334). In this manner, only the radiotransparent upper portion (302) intersects the treatment beam (334).

FIGS. 3C-3D illustrate cross-sectional side views of another variation of a patient platform system (350) comprising a patient platform (351) having a rigid portion and a radiotransparent portion that maintain their positions relative to each other. The system (350) may comprise a patient platform (351) having an upper portion (352) fixed relative to a lower portion (354). For instance, a length of a cantilevered portion of the upper portion (352) is constant in FIGS. 3C-3D. In some variations, the upper portion (352) may be radiotransparent and the lower portion (354) may be radiopaque. A base (356) of the patient platform (351) may be coupled to the lower portion (354) and configured to control a height and/or pitch of the patient platform (351). The lower portion (354) may be movable with respect to the base (356) such that the patient platform (351) may move relative to the base (356). Accordingly, the patient platform (351) may telescope in an axial direction with respect to the base (356) as it is extended into and out of a gantry (310). The lower portion (354) may be made of any material that is sufficiently rigid such that regardless of the length of the lower portion (354) that may be cantilevered from the base (356) (e.g., FIG. 3D), the lower portion (354) does not sag with respect to the base (356). Additionally or alternatively, the lower portion (354) may be made of any material that is more rigid than the material of the upper portion (352).

Since the upper portion (352) may be fixed relative to the lower portion (354), it should be appreciated that a patient (not shown) laying on the patient platform (351) may cause constant sag to the patient platform (351) (assuming the patient does not move). Consequently, the sag of the patient platform (351) may comprise a set of known values across a length of the patient platform (351). That is, the sag of the patient platform at a particular region of interest of a patient may be determined prior to and/or at the start of a treatment session and remain the same throughout the session, regardless of how the platform (352) moves with respect to the base (356). Furthermore, by fixing the upper portion (352) to the lower portion (354), the patient platform (351) illustrated in FIGS. 3C-3D may be simpler to manufacture than the patient platform (301) illustrated in FIGS. 3A-3B.

With respect to an imaging procedure, the system (350) may be in an imaging configuration, an example of which is depicted in FIG. 3C. As shown there, a controller (340) may be configured to move the lower portion (354) (that may be radiopaque) as close to the imaging beam (322) as possible without intersecting the imaging beam (322). In this manner, the radiopaque portion of the patient platform (351) may be moved as close as possible to a path of the imaging beam (322) without interfering with the imaging beam (322). In some variations, the lower portion (354) may be positioned such that a leading edge of the lower portion (354) may be located at a predetermined first distance away from the imaging plane (FIG. 3C). For example, the first distance may be about 2 centimeters. The upper portion (352) may intersect the imaging beam (322) to image a desired region of the patient (not shown).

As shown in FIG. 3C, a controller (340) of the system (350) may be configured to move the upper portion (352) and lower portion (354) such that the lower portion (354) is non-intersecting with the imaging plane of the imaging beam (322) and the upper portion (352) intersects the imaging plane of the imaging beam (322). In this manner, only the radiotransparent upper portion (352) intersects the imaging beam (322).

With respect to a radiotherapy procedure, the system (350) may be disposed in a treatment configuration, an example of which is depicted in FIG. 3D. As shown there, the controller (340) may be configured to move the rigid lower portion (354) (that may be radiopaque) as close to the treatment beam (334) as possible without interfering with the treatment beam (334). In this manner, the lower portion (354) of the patient platform (351) may be moved as close as possible to the treatment beam (334) without receiving a radiation dose. In some variations, the lower portion (354) may be positioned such that a leading edge of the lower portion (354) may be located at a predetermined second distance away from the treatment plane (FIG. 3D). For example, the second distance may be about 2 centimeters. The upper portion (352) may intersect the treatment beam (334) to treat the patient (not shown). In the treatment configuration depicted in FIG. 3D, the imaging radiation source (320) may not be activated because the rigid lower portion (354) (that may be radiopaque) is located in the beam path of the imaging radiation source (320).

As shown in FIG. 3D, a controller (340) of the system (350) may be configured to move the patient platform (351) such that the lower portion (354) is non-intersecting with the treatment plane of the treatment beam (334) and the upper portion (352) intersects the treatment plane of the treatment beam (334). In this manner, only the radiotransparent upper portion (352) intersects the treatment beam (334).

In some non-limiting, exemplary variations, the upper portion (302, 352) may comprise radiotransparent carbon fiber and the lower portion (304, 354) may comprise radiopaque aluminum or other stiff, low-Z materials. In these variations, the aluminum portion of the patient platform (301, 351) may be configured to sag less than the carbon fiber portion (302, 352). In some variations, the lower portion (304, 354) may be thicker than the upper portion (302, 352). In some variations, the lower portion (304, 354) may have a height of about 0.02-0.50 meters and the upper portion (302, 352) may have a height less than the lower portion (302, 354). In some variations, the patient platform (300, 350) described may comprise a vertical drive system (e.g., scissor elements) as described in detail with respect to FIGS. 4A-4E.

Adjustable Patient Platform

Generally, the patient platform devices described here may provide a plurality of degrees of freedom to move a patient on a patient platform to a desired position and orientation with respect to a radiotherapy treatment beam.

As shown in FIGS. 4A-4C and 4F, a patient platform (401) may provide at least one of axial, lateral, and vertical translation, as well as pitch and/or yaw rotation.

Figure 4A:
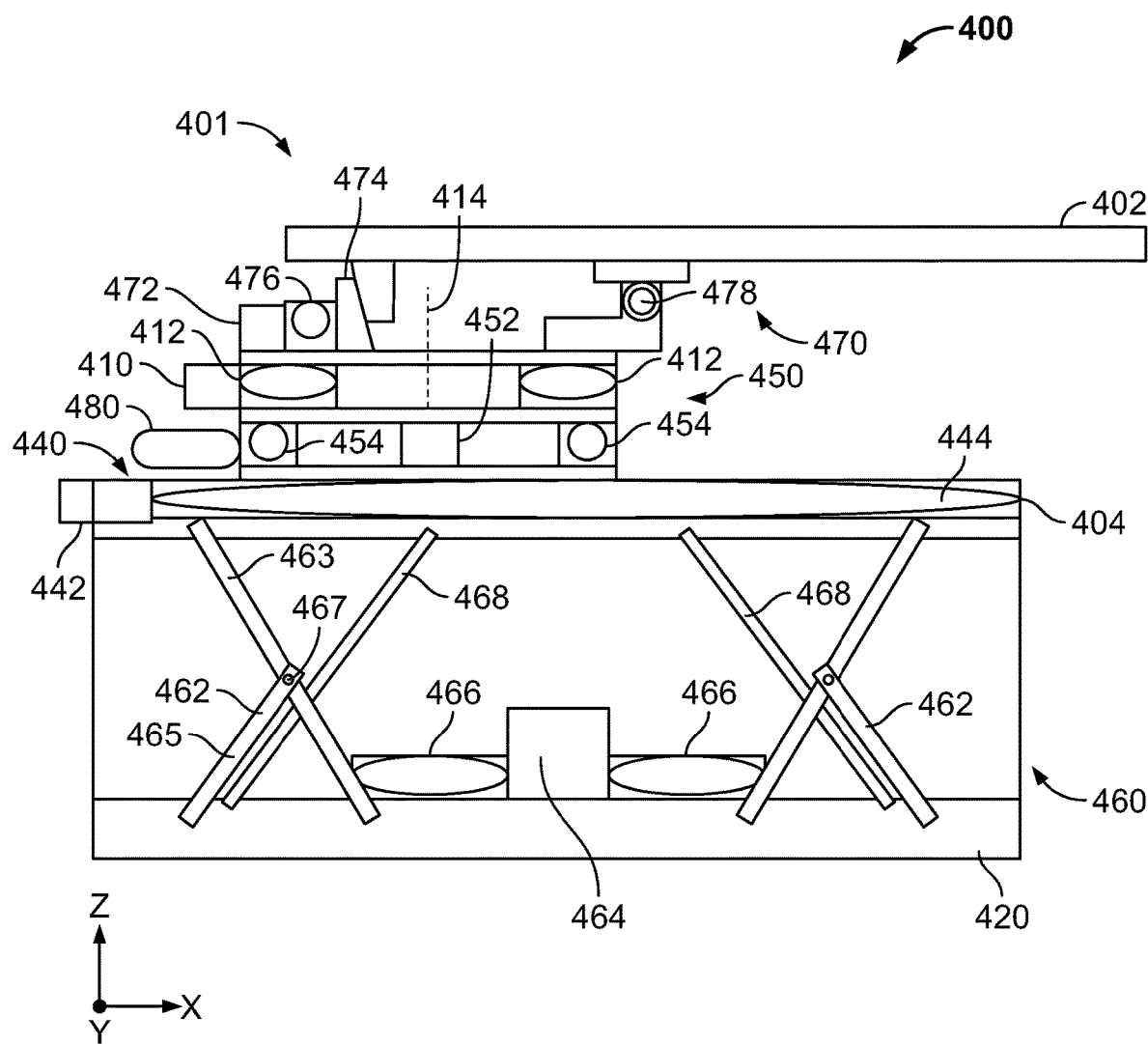
FIGS. 4A-4F are illustrative depictions of variations of a radiotherapy patient platform system.
Figure 4B:
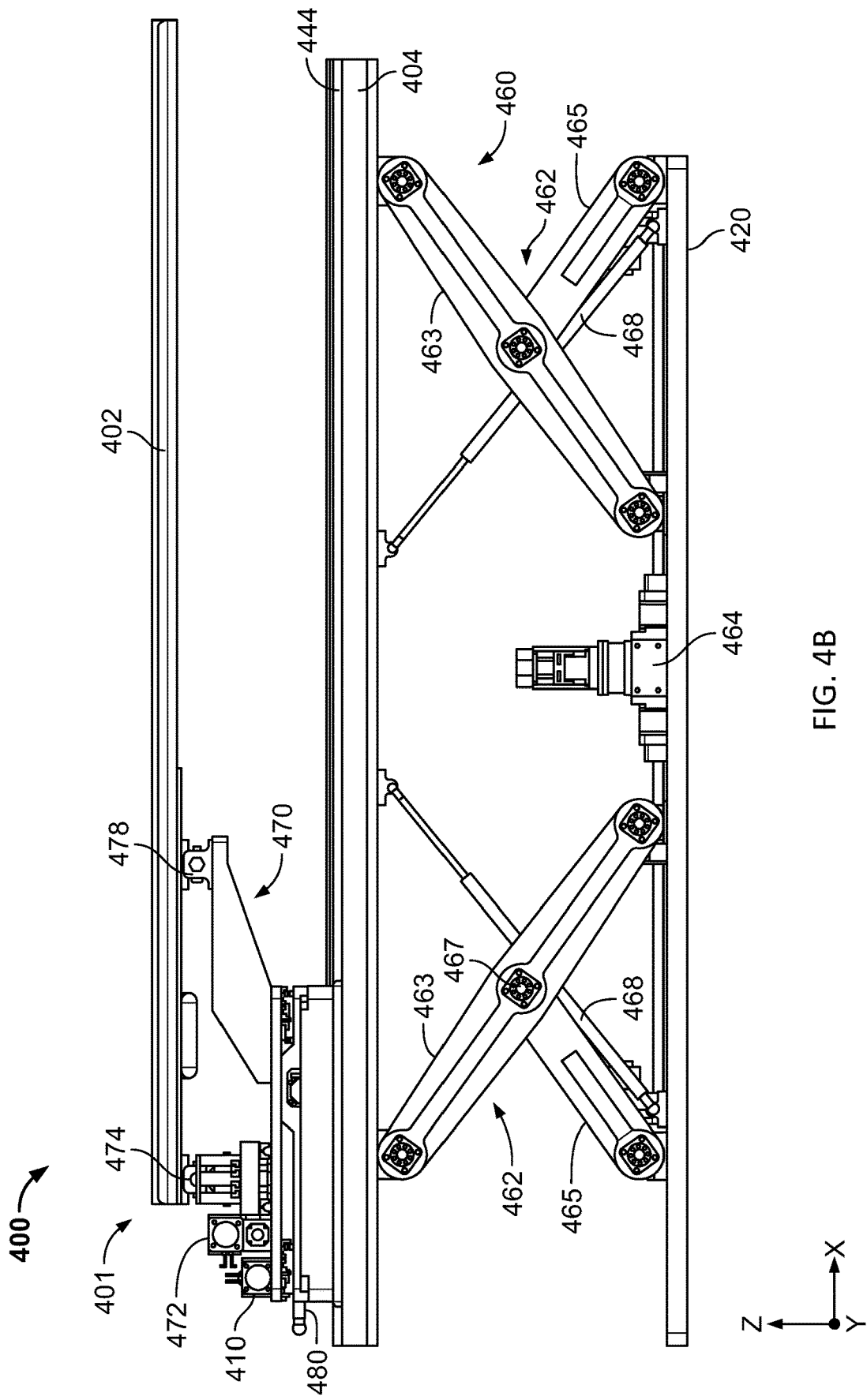
Figure 4C:
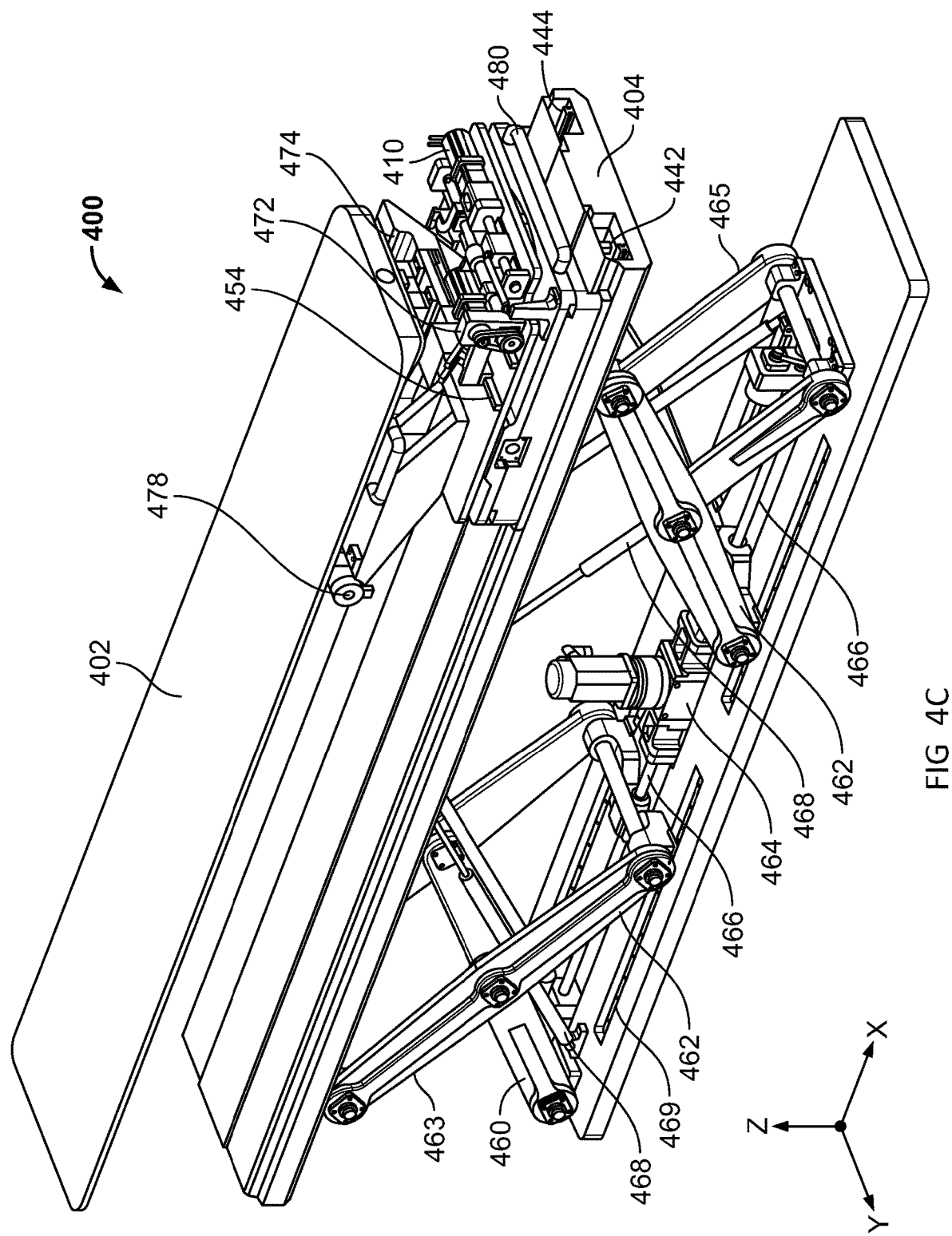
Figure 4D:
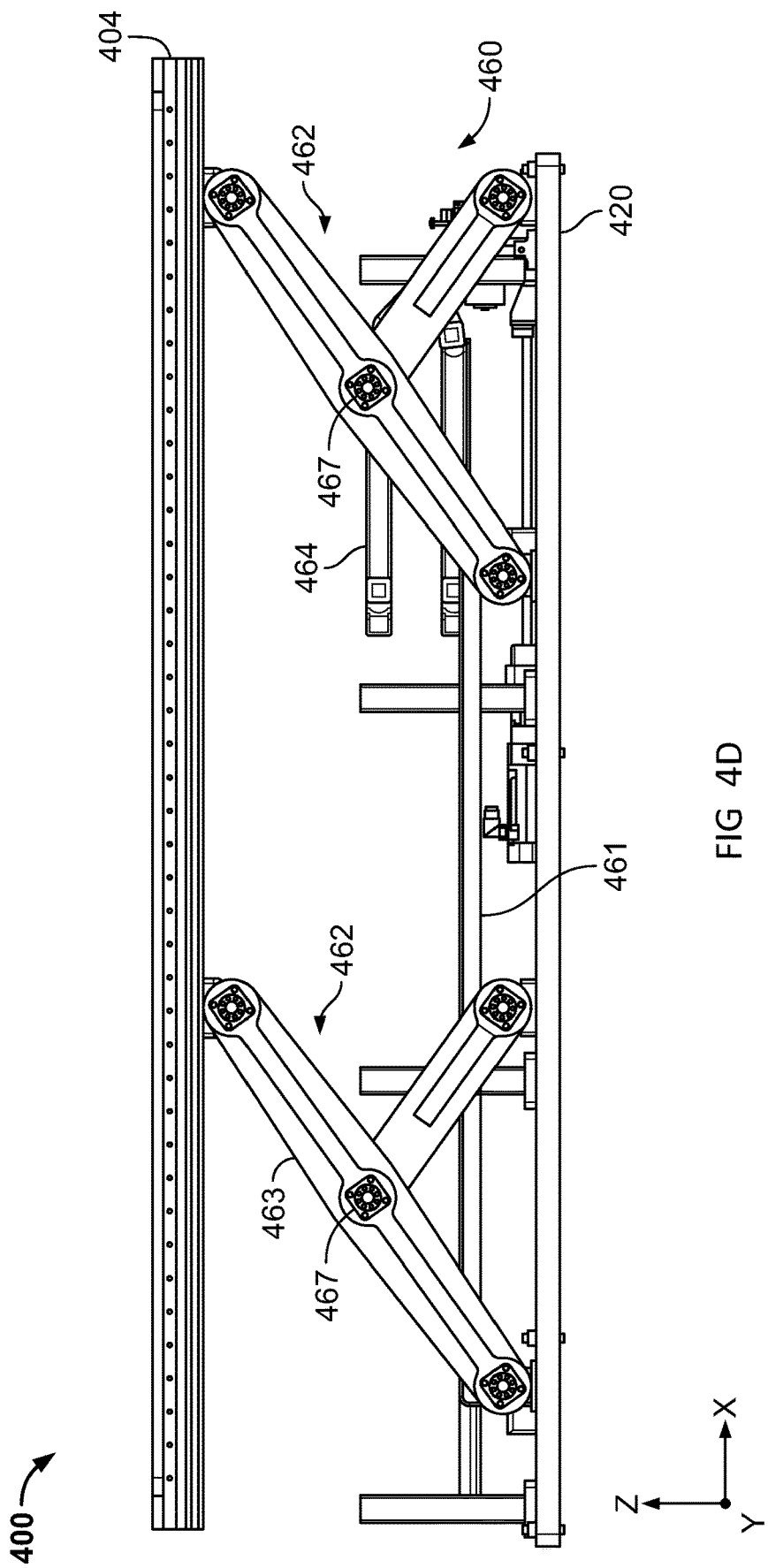
Figure 4E:
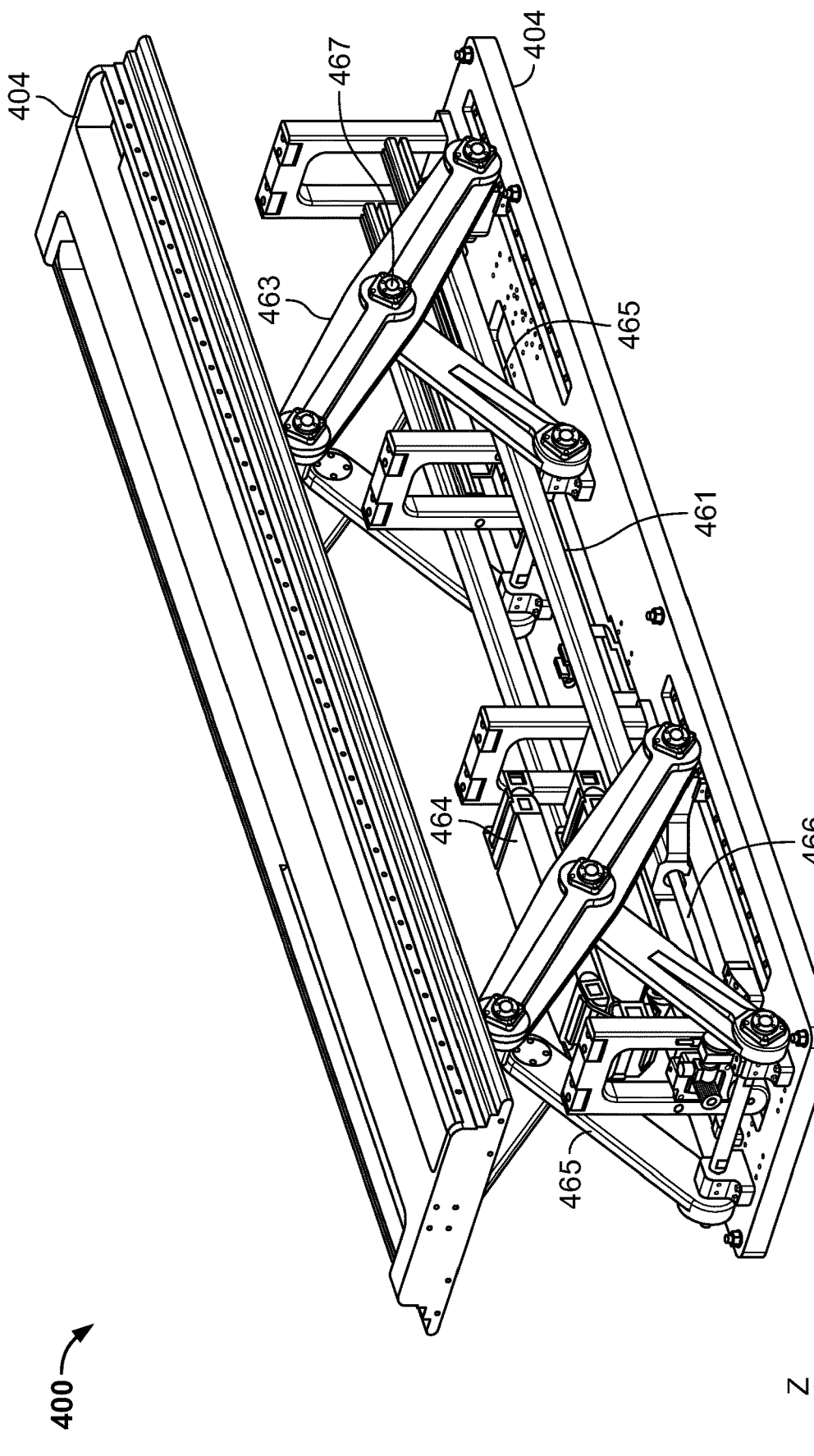
Figure 4F:
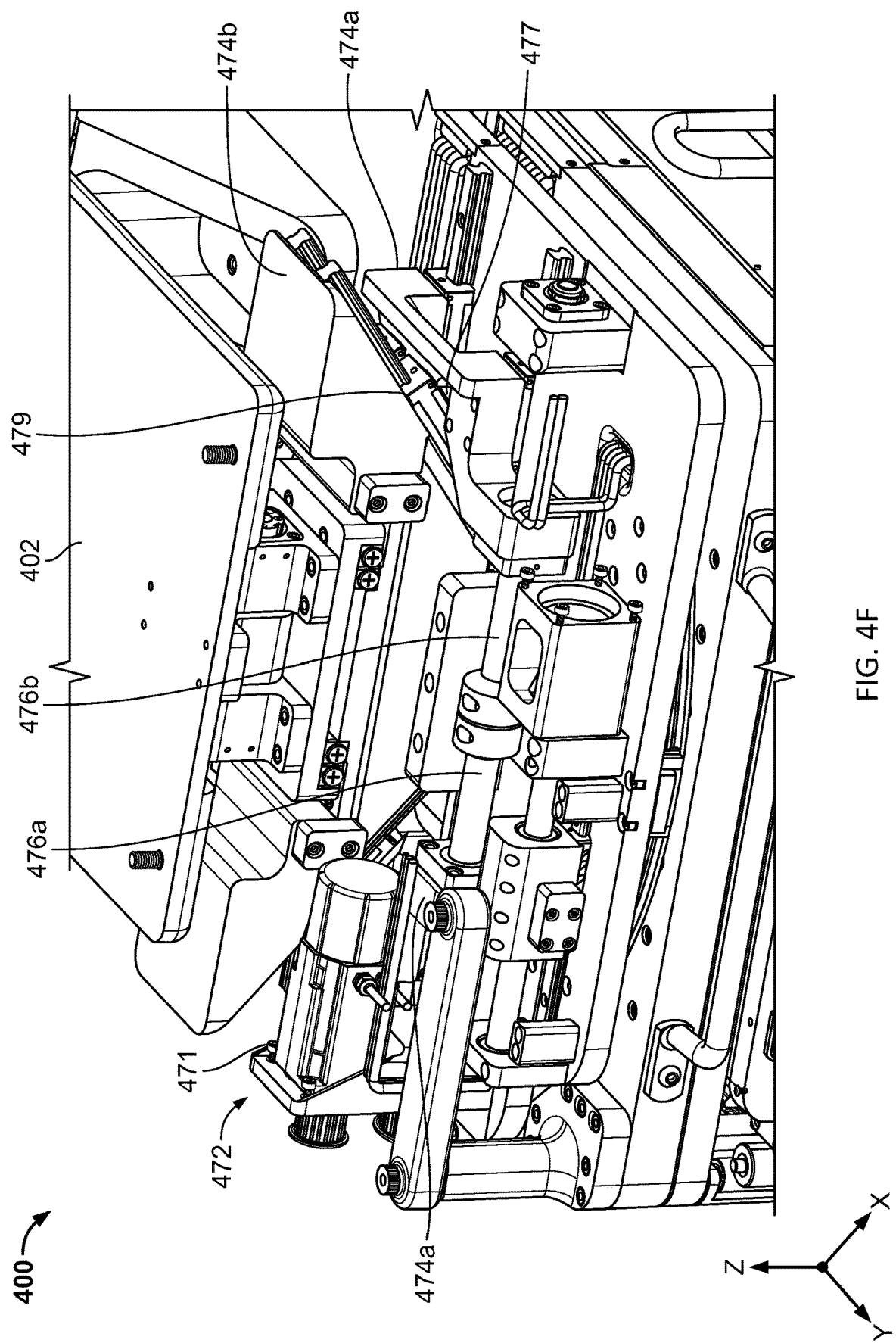

FIGS. 4A-4B and 4D are side views and FIGS. 4C, 4E, and 4F are perspective views of a system (400) comprising a radiotransparent patient platform (401) coupled to a base (420). The base (420) may be provided external to a patient region of a gantry (not shown for clarity) and may not be radiotransparent. The patient platform (401) may comprise an upper portion (402) and a lower portion (404). The upper portion (402) is not drawn to scale (e.g., the upper portion (402) is relatively short in FIG. 4A) for the sake of illustration. A pivot (412) may couple the upper portion (402) of the patient platform (401) to the lower portion (404) of the patient platform (401). In some variations, the pivot (412) may comprise a set of curved rails (e.g., two). It should be appreciated that the pivot (412) may allow the upper portion (402) of the patient platform (401) to rotate about the Z-axis (414) without interfering with either an imaging or treatment beam.

In some variations, one or more of an axial drive system (440), lateral drive system (450), vertical drive system (460), pitch drive system (470), and yaw drive system (410) may be coupled to the patient platform (401). For example, the axial drive system (440) may be coupled between the lower portion (404) and the lateral drive system (450), the lateral drive system (450) may be coupled between the axial drive system (440) and the yaw drive system (410), the yaw drive system (410) may be coupled between the lateral drive system (450) and the pitch drive system (470), and the pitch drive system (470) may be coupled between the yaw drive system (410) and the upper portion (402). This configuration allows the axial drive system (440), lateral drive system (450), pitch drive system (470), and yaw drive system (410) to move axially relative to the vertical drive system (460) such that movement of the vertical drive system (460) may be independent of the other drive systems.

In some variations, the system (400) may comprise a controller (not shown) comprising a processor and memory configured to control one or more of the lateral drive system (450), vertical drive system (460), pitch drive system (470), and yaw drive (410). In some variations, the axial drive system (440), lateral drive system (450), and pitch drive system (470) may each comprise a pair of linear rails driven by a single motor (e.g., leadscrew drive, linear motor). The axial drive system (440) may comprise an axial drive element (442) coupled to the lower portion (404) of the patient platform (401). A pair of axial rails (444) may be coupled to the axial drive element (442). The axial drive system (440) may be configured to move the upper portion (402) in an axial direction (along the X-axis) relative to the lower portion (404) by moving the upper portion (402) along the axial rails (444). In some variations, the axial drive element (442) may comprise a rotary motor coupled to a leadscrew and/or drive belt that are in turn coupled to the axial rails (444). For example, the axial drive element (442) may generate a motor continuous peak torque of up to about 0.5 Nm. In other variations, the axial drive element (442) may comprise a linear motor coupled to the axial rails (444). In some variations, the axial rails (444) may be spaced apart from each other between about 35 cm and 55 cm. A cross-sectional width of each rail (444) may be between about 15 mm and about 30 mm. In some variations, the axial drive system (440) may be configured to axially translate the upper portion (402) relative to the lower portion (404) in a range of up to about 200 cm.

Figure 13A:
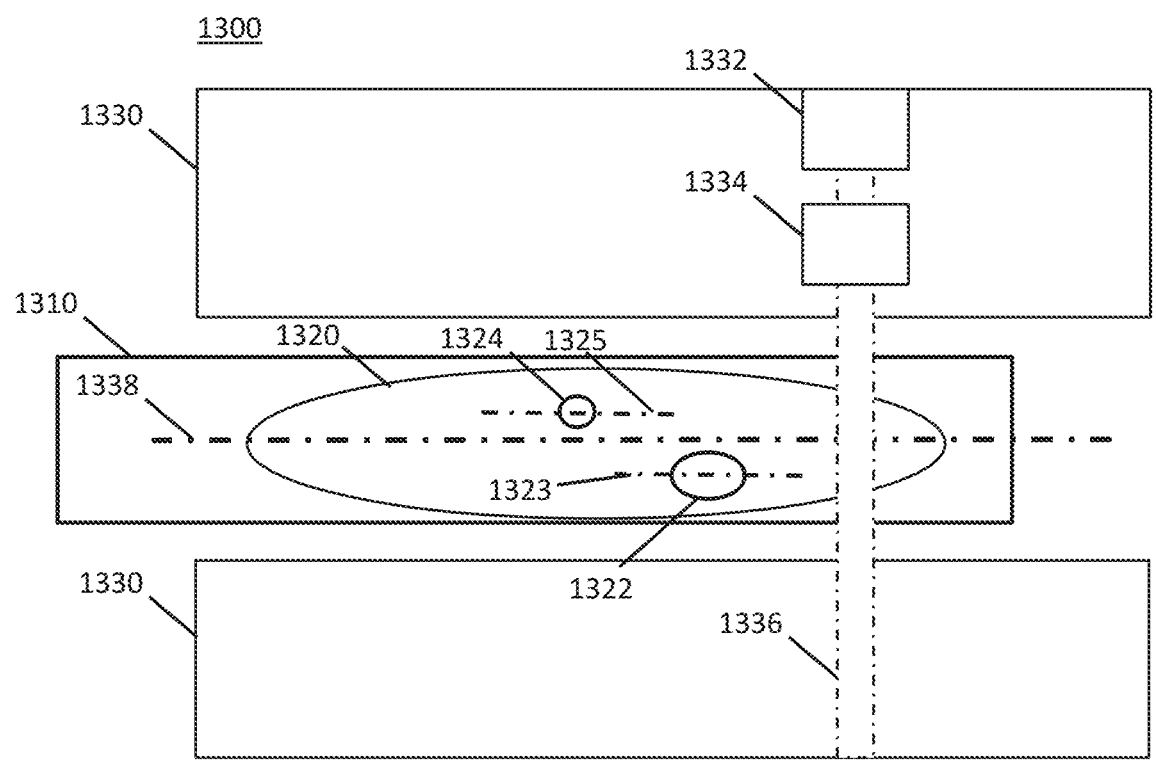
FIGS. 13A-13E are illustrative plan views of variations of a radiotherapy patient platform.
Figure 13B:
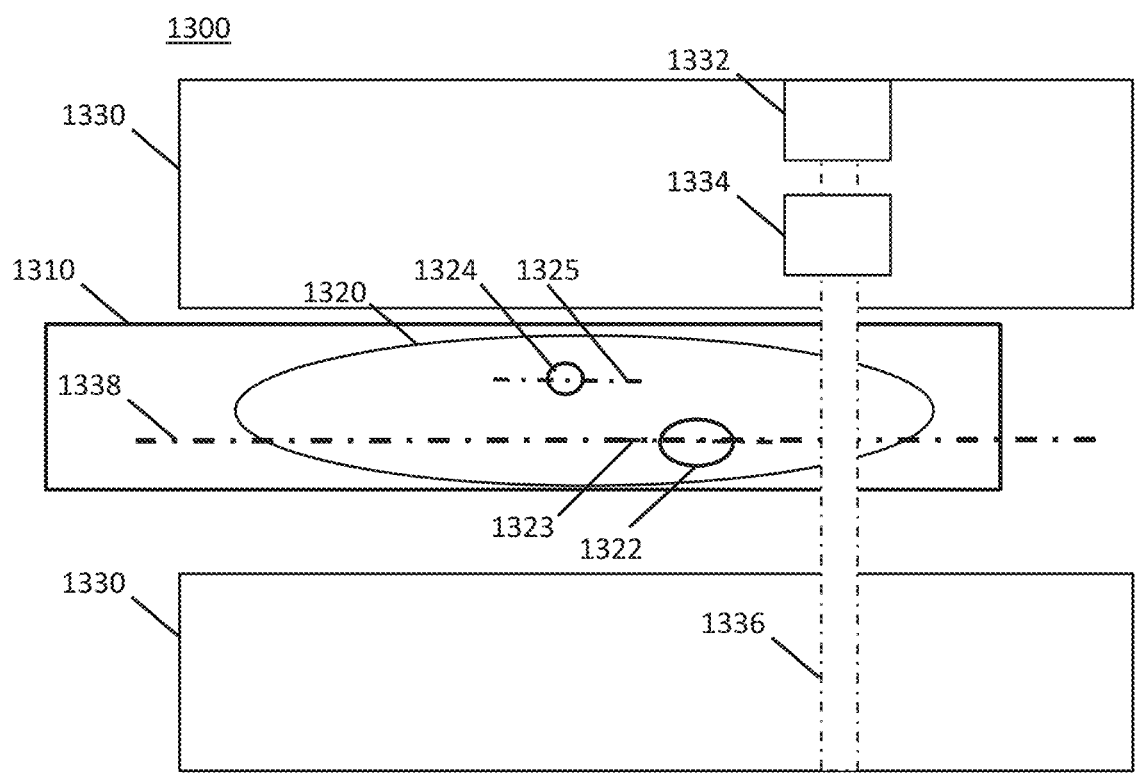
Figure 13B:
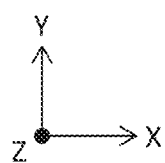
Figure 13C:
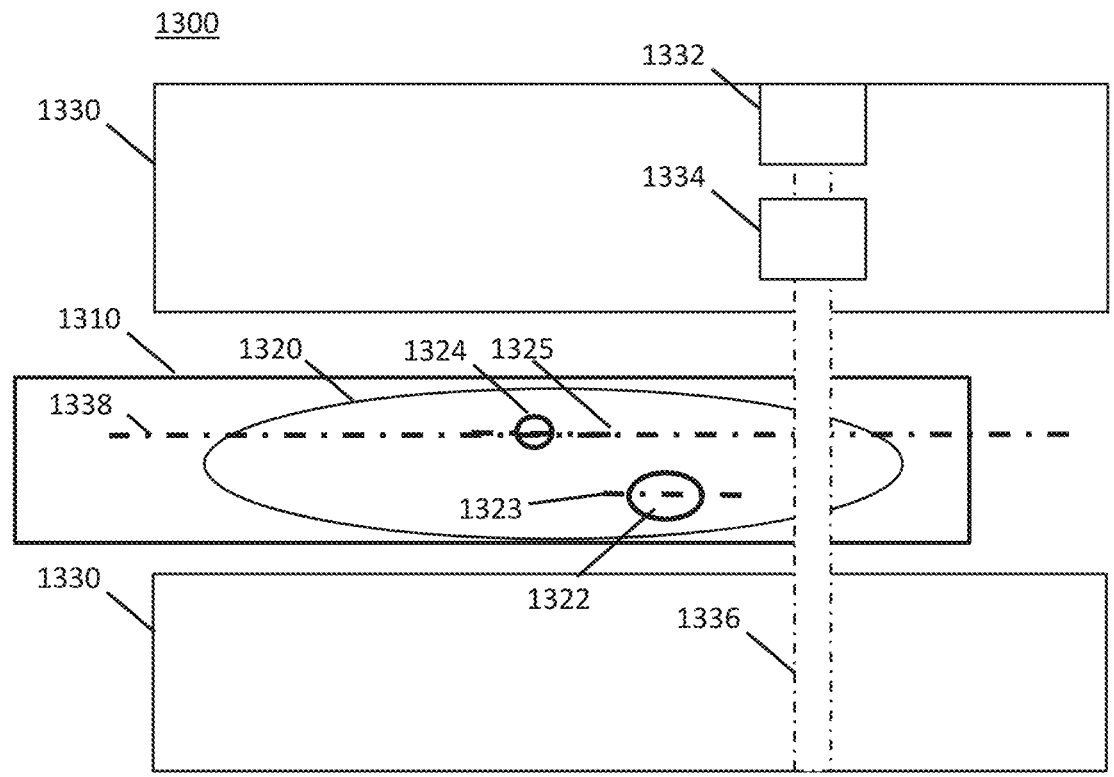

The lateral drive system (450) may comprise a lateral drive element (452) coupled to the patient platform (401). A pair of lateral rails (454) may be coupled to the lateral drive element (452). The lateral drive system (450) may be configured to move the upper portion (402) in a lateral direction (along the Y-axis) relative to the lower portion (404) by moving the patient platform (401) along the lateral rails (454). For example, FIGS. 13A-13C illustrate a patient platform (1310) moving in a lateral direction (along the Y-axis) within a gantry (1330). The lateral rails (454) may be disposed perpendicular to the axial rails (444). The lateral drive element (452) may generate a motor continuous peak torque of up to about 0.5 Nm. In some variations, the lateral rails (454) may be spaced apart from each other between about 45 cm and about 75 cm. A cross-sectional width of each rail (454) may be between about 15 mm and about 30 mm. In some variations, the lateral drive system (450) may have a lateral range of motion of up to about 200 cm.

The pitch drive system (470) coupled to the patient platform (401) may be configured to raise and/or lower an end of an upper portion (402) so as to pitch the upper portion (402) about a pitch pivot (478). A pitch drive element (472) may be coupled to one or more wedges (474) to vertically translate an end of the upper portion (402). In some variations, the pitch drive system (470) may comprise a pitch drive element (472) coupled to the patient platform (401). In some variations, the pitch drive system (470) may comprise a pair of wedges (474) coupled to the pitch drive element (472) via a pitch linear screw (476). The pitch drive system (470) may be configured to pitch the patient platform (401) about a pitch pivot (478) (about the Y-axis). For example, the pitch drive element (472) and screw (476) may drive one of the two wedges (474) laterally (along the Y-axis) such that the second of the two wedges (474) is pushed upward (along the Z-axis). Pushing the second wedge upward may tilt the upper portion (402) of the patient platform (401) such that a first end of the upper portion (402) of the patient platform (401) (to which the wedges (474) are coupled) is higher than a second end of the upper portion (402) of the patient platform (474). Rotation about the pitch pivot (478) enables the pitching, or tilting, of the upper portion (402) of the patient platform (474) relative to a horizontal plane (e.g., the X-Y plane and lower portion (404) plane).

FIG. 4F is a perspective view of a variation of a pitch drive system (470) as depicted in FIG. 4C. In particular, the pitch drive element (472) may comprise a motor (471) comprising a toothed belt coupled to the pitch linear screw (476). For example, the motor (472) may be coupled to a first linear screw (476a) and a second linear screw (476b). The first and second linear screws (476a, 476b) may be coupled to respective portions of a first wedge (474a) (e.g., lower wedge). Each portion of the first wedge (474a) may be coupled to a pair of laterally-oriented linear rails. The first wedge (474a) may move symmetrically laterally via the screw (476) such that the two portions of the first wedge (474a) simultaneously move towards or away from each other.

The wedge (474) may further comprise a second wedge (474b) (e.g., upper wedge) slidably coupled to the first wedge (474a) via a set of linear rails. For example, the first wedge (474a) may comprise a first angled surface (477) disposed facing a second angled surface (479) of a corresponding second wedge (474b). The second angled surface (479) may comprise a set of linear rails on which the first wedge (474a) slides. Lateral motion of the first wedge (474a) may be thus translated to vertical motion of the second wedge (474b) and upper portion (402) such that the upper portion (402) may pitch. In some variations, the pitch drive system (470) may pitch up a proximal end of the upper portion (402) by up to about 5 degrees and pitch down the upper portion (402) by up to about 3 degrees. In some variations, a change in pitch of the upper portion (402) may be used to counteract sag of the cantilevered end of the upper portion (402).

In some variations, each portion of the first wedge (474a) may comprise a width of between about 200 mm and about 250 mm, a length of between about 60 mm and about 120 mm, and a height of between about 25 mm and about 75 mm. For example, each portion of the first wedge (474a) may comprise a width of about 220 mm, a length of about 90 mm, and a height of about 50 mm. In some variations, a first angled surface (477) may comprise an angle of between about 30 degrees and about 50 degrees relative to the horizontal plane (i.e., X-Y plane). For example, the first angled surface (477) may comprise an angle of about 38 degrees.

In some variations, each portion of the second wedge (474b) may comprise a width of between about 40 cm and about 60 cm, a length of between about 50 mm and about 150 mm, and a height of between about 10 cm and about 30 cm. For example, each portion of the second wedge (474b) may comprise a width of about 50 cm, a length of about 10 cm, and a height of about 20 cm. In some variations, a second angled surface (479) may comprise an angle of between about 130 degrees and about 150 degrees relative to the horizontal plane (i.e., X-Y plane). For example, the second angled surface (479) may comprise an angle of about 142 degrees.

As shown in FIGS. 4A-4C, the vertical drive system (460) in some variations may comprise a pair of scissor elements (462) and corresponding cylinders (468) (e.g., hydraulic, pneumatic) coupled to the patient platform (401). The vertical drive system (460) may be configured to move the patient platform (401) in a vertical direction (along the Z-axis) relative to the base (420). Vertical movement of the patient platform (401) may be independent of other translational and/or rotational movement provided by the axial drive system (440), lateral drive system (450), pitch drive system (470), and yaw drive system (410). A vertical drive element (464) may be coupled to the scissor elements (462) through one or more linear screws (466) and configured to raise and/or lower the patient platform (401). One or more cylinders (468) may be configured to generate an upward force to assist the vertical drive element (464) and move the patient platform (401). In some of these variations, one or more of the cylinders (468) may be pivotally coupled to the base (420) and the lower portion (404) of the patient platform (401). The scissor element (462) may comprise a first arm (463) and a second arm (465) coupled to each other about a pivot point (467). The pivot point (467) may couple an intermediate portion of the first arm (463) to an end portion of the second arm (465). The other end of the second arm (465) may pivotally couple to the base (420). An end of the first arm (463) may pivotally couple to the lower portion (404). The other end of the first arm (463) may pivotally couple to a track (469) of the base (420) such that the first arm (463) may slide axially along the track (469) (along the X-axis). A track (469) may be provided for each of the first arms (463). As shown in FIGS. 4C and 4E, some variations of the vertical drive system (460) may comprise four pairs of first and second arms (463, 465) with two pairs disposed at each of the ends of the base (420) and lower portion (404). The scissor elements (462) shown in FIGS. 4A-4C may comprise a mirror configuration. In some variations, the vertical drive system (460) may be located at a fixed position outside of a gantry while the other drive systems may translate axially relative to the gantry.

FIGS. 4A and 4C illustrate a vertical drive element (464) comprising two linear screws (466) configured to drive the pair of scissor elements (462) disposed at each end of the patient platform (400). As the vertical drive element (464) drives one or more of the linear screws (466) axially (along the X-axis) away from the vertical drive element (464), the lower portions of the first arms (463) may be brought closer to their respective second arms (465) such that the height of the scissor element (462) and lower portion (404) is increased. Conversely, the vertical drive element (464) may decrease a height of the lower portion (404). The patient platform (400) may be pitched (e.g., tilted) when the linear screws (466) are driven unequally. In some variations, the first arms (463) may comprise a length of between about 60 cm and about 100 cm, and the second arms (465) may comprise a length of between about 30 cm and about 60 cm. In some variations, the track (469) may comprise a length of between about 50 cm and about 90 cm. In some variations, the vertical drive system (460) may comprise a vertical range of motion of up to about 60 cm.

In some variations, as shown in FIGS. 4D and 4E, the vertical drive system (460) may comprise a pair of scissor elements (462) in a parallel configuration. That is, each of the first arms (463) in the parallel configuration face the same direction and are parallel to each other. Likewise, each of the second arms (465) face the same direction and are parallel to each other. This configuration of scissor elements may reduce a size and/or simplify the vertical drive element (464). A vertical drive element (464) may be directly coupled to one pair of scissor elements (460) via a linear screw (466) at one end of the patient platform. The pairs of scissor elements (462) at each end of the patient platform (400) may be coupled via a linkage (461). For example, the linkage (461) may couple the first arms (463) at each end of the patient platform (400) to each other. This allows the vertical drive element (464) to drive each of the scissor elements (462) simultaneously (e.g., together) using one linear screw (466) rather than providing a linear screw for the scissor elements at each end of the patient platform (400). As the vertical drive element (464) drives (e.g., rotates) the linear screw (466) axially (along the X-axis) away from the vertical drive element (464), the lower portions of the first arms (463) may be brought farther away from their respective second arms (465) such that the height of the scissor element (462) and lower portion (404) is decreased. In some variations, the vertical drive element (464) may comprise a pneumatic element, an electromechanical element, or hydraulic element. In some variations, the cylinder (468) may further comprise one or more cylinders as described with respect to FIGS. 4A-4C.

The yaw drive system (410) may be coupled to the upper portion (402) of the patient platform (401). The yaw drive system (410) may comprise a yaw drive element and be configured to yaw (rotate) the upper portion (402) of the patient platform (401) relative to the lower portion (404) of the patient platform (401) about a pivot axis (414) of pivot (412) by moving the patient platform (401) along the curved rails (412). In some variations, the curved rail may provide a stiff base and comprise a length of about 1.0 cm and about 10.0 cm. In some variations, the curved rails (412) may comprise a radius of between about 25 cm and about 35 cm, and be spaced apart between about 50 cm and about 70 cm. In some variations, the yaw drive system (410) may provide a range of motion of up to about 25 degrees.

The lower portion (404) of the patient platform (401) depicted in FIG. 4A does not yaw. In some variations, the patient platform (401) may comprise a handle (480) for an operator to manually adjust a position of the patient platform (e.g., adjust an axial position and/or lateral position). It should be noted that the system (400) described above may be used in conjunction with any of the methods corresponding to FIGS. 12 and 13A-13E described and illustrated below. In some variations, the system (400) as described herein may be used to move the patient platform as described in detail herein, such as with respect to the methods described in FIGS. 13A-13E.

In some variations, one or more portions of the patient platform (401) may comprise carbon fiber due to its radiotransparency and ability to provide rigid support to a patient. In some variations, the patient platform (401) may have a length of about 1.5 m and about 3.0 m, a width of about 0.50 m and about 2.0 m, and a thickness of about 0.05 m and about 0.50 m, and may preferably have a length of about 2 m, a width of about 0.50 m, and thickness of about 0.10 m. In some variations, the patient platform (401) may have a weight capacity of about 210 kilograms and have an extension length from an end of the base (112) of about 2 m. In some variations, the patient platform (401) may comprise one or more of the elongate elements and/or bores as described in detail herein with respect to FIGS. 1A-1F. In some variations, the patient platform (401) may comprise a conformable substrate as described in detail herein with respect to FIGS. 2A-2C.

Phantom

Generally disclosed herein are patient platforms comprising a phantom for use in calibrating one or more components of a radiotherapy system. For example, a radiotherapy system may comprise a rotatable gantry, one or more radiation detectors mounted on the gantry, a radiation source (e.g., linac) mounted on the gantry, and a beam-shaping assembly disposed in the radiation beam path of the radiation source. The beam-shaping assembly may comprise one or more sets of jaws and/or collimators. Additionally or alternatively, some radiotherapy systems may comprise an imaging system, such as a CT system, that may be used to acquire CT images. The radiation detector may receive a beam emitted through the phantom from the radiation source. The phantom may comprise a plurality of types of radiation detectors and may be used to characterize, verify, and/or calibrate the expected or desired function of the radiation source, multi-leaf collimator, radiation detector, as well as to verify performance of dose delivery and dose calculation algorithms. The data generated by one or more of these dosimeters may be used for quality assurance procedures. For example, a daily quality assurance procedure may quickly generate dose data using two beams emitted through two water-filled steps of different depths for calibration of a radiation detector. Another quality assurance procedure (e.g., weekly, monthly, quarterly) may use a plurality of beams emitted through a plurality of radiation detectors (e.g., water-filled steps, ionization chambers, radiographic film). Generating a larger set of dose data from a plurality of radiation detector types may increase the accuracy of the dose data and subsequent verification and/or calibration by allowing cross-calibration of dose data generated by different types of radiation detectors (e.g., ionization chambers, radiographic sheets, etc.). In some variations, the phantom may be mounted to an underside of a patient platform at a predetermined location that allows for convenient storage outside of a patient treatment region of a patient platform. In particular, the location of the phantom underneath and away from the patient treatment region allows a patient to be disposed on a patient support surface of the patient platform and receive radiotherapy treatment without interference from the phantom. In other words, a portion of the space underneath the patient platform may be efficiently used to mount the phantom without altering a radiotherapy procedure using the patient platform.

Figure 16A:
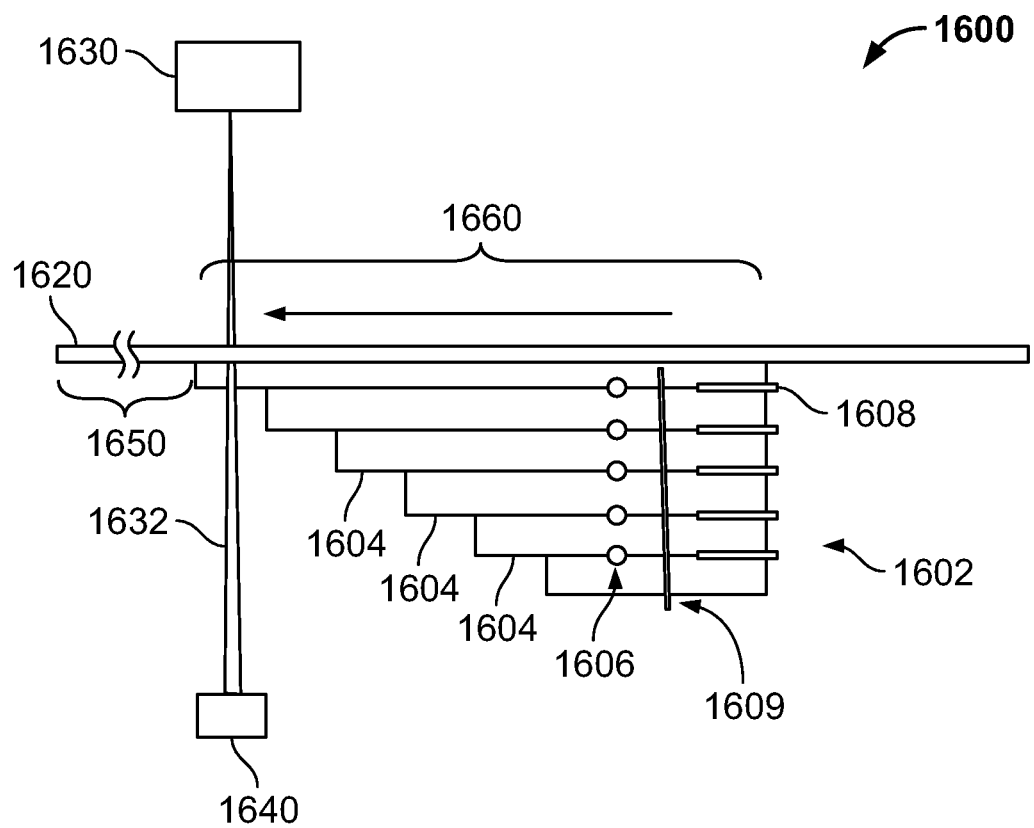
FIGS. 16A and 16B are illustrative cross-sectional side views of a variation of a phantom for a radiotherapy system.
Figure 16B:
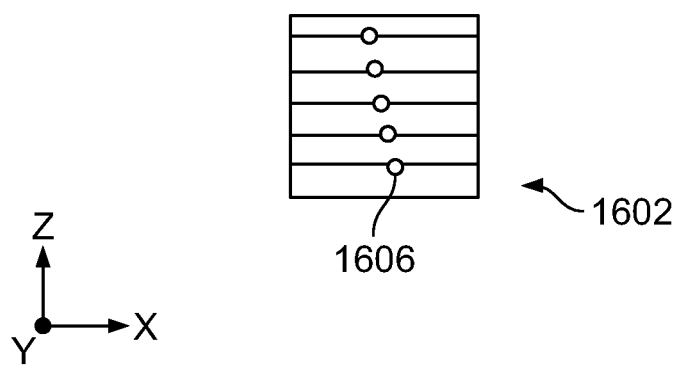

FIGS. 16A-16B depict cross-sectional side views of some variations of a phantom (1602). For example, FIG. 16A depicts a radiotherapy system (1600) comprising a patient platform (1620) and a phantom (1602) coupled (e.g., mounted) to an underside of the patient platform. The patient platform (1620) may have a patient support surface configured to hold a patient thereon (e.g., side facing the radiation source (1630) in FIG. 16A) with the underside surface disposed opposite the patient support surface (e.g., side facing the radiation detector (1640) in FIG. 16A). The patient platform (1620) is not drawn to scale (e.g., the patient region (1650) is relatively short in FIG. 16A) for the sake of illustration. A radiation source (1630) and a radiation detector (1640) may be disposed on a gantry (not shown for the sake of clarity) and positioned relative to the patient platform (1620) to generate a beam path that intersects the patient platform (1620) and phantom (1602). The phantom (1602) may be disposed within a phantom region (1660) of the patient platform (1620) that is outside a patient region (1650). That is, the patient region (1650) and not the phantom region (1660) may be positioned to intersect a beam plane of the radiation source (1630) during a treatment session. The patient platform (1620) may be advanced such that the beam plane intersects the phantom region (1660) only during a quality assurance procedure. The phantom (1602) may comprise a housing having an internal volume configured for liquid such as water. For example, the housing may define an internal fluid-tight volume. The housing may comprise a material such as acrylic (e.g., polymethylmethacrylate (PMMA)) that may be dosimetrically similar to water.

As shown in FIG. 16A, the housing of the phantom (1602) may comprise a plurality of steps (1604) arranged along a longitudinal axis (e.g., X-axis) of the phantom (1602). Each step may have a corresponding predetermined depth. The system (1600) may be configured to deliver a predetermined radiation dose to one or more of the steps such that delivered dose measurements may be compared to reference dose data (e.g., expected dose measurements) for each of the steps. Differences between the measured dose and expected dose may be used for calibration of one or more components of the system (1600). The phantom (1602) may comprise two or more steps such that the detector (1630) may generate dose data corresponding to at least two step depths of the phantom when respective beams (1632) pass through each step. The dose data at different step depths may be used for absolute and/or relative dosimetry calculations. In some variations, dose data generated by the detector (1640) using the steps (1604) may be calibrated against one or more of dose data generated using the ionization chambers (1606), dose data generated using radiographic films, and/or dose data generated by other dosimeters.

In some variations, dose data may be used to calculate a tissue phantom ratio (TPR) where a first point dose of radiation is measured at a first depth (e.g., reference depth of about 5 cm) and at least a second point dose is measured at a second depth (e.g., about 10 cm). The TPR may be used to characterize the beam quality of a radiation source and point dose measurements at a plurality of depths may be used to improve an accuracy of the TPR value.

In some variations, the phantom (1602) may comprise 2, 3, 4, 5, 6, 7, or more steps. For example, the phantom (1602) may comprise five or six steps of the same material (e.g., water). In some variations, the steps may have different materials. For example, each step may comprise different densities and/or attenuation characteristics. Each step may comprise a depth (i.e., along the Z-axis) of at least about 1 cm and about 4 cm or more when filled with water. The phantom (1602) may comprise a width (i.e., along the Y-axis) of at least about 2 cm. Each step (1604) may have a length of between about 2 cm and about 5 cm. For example, a phantom (1602) comprising six steps may have a depth of between about 25 cm and about 40 cm. Each step (1604) of the phantom (1602) may comprise a plateau in parallel with a longitudinal axis (i.e., X-axis) of the phantom (1602). In other variations, the steps (1604) of the phantom (1602) may be spaced apart along the lateral axis (i.e., Y-axis) of the patient platform (1620). Although the steps (1604) depicted in FIG. 16A correspond to a monotonic function and resemble a set of stairs, the steps (and their corresponding depths) may be ordered and spaced along the longitudinal axis of the phantom in any desired configuration.

The phantom (1602) may further comprise a plurality of radiation detectors (e.g., ionization chambers and dosimeter slots). In some variations, each of the radiation detectors (1606, 1608) may be disposed at the predetermined depth of its corresponding step (1604). In some variations, the phantom (1602) may comprise one or more radiation detectors including a gas-filled radiation detector such as an ionization chamber (1606). The ionization chamber (1606) may comprise an air chamber having an anode-cathode electrode pair. The electrode pair may be coupled to an electrometer and power supply (not shown in FIG. 16A). A voltage potential applied between the electrode pair may generate an electric field in the chamber (1606). When the gas in the chamber is ionized by a radiation beam (1632) emitted from the radiation source (1630), the resultant ionization current generated in the ionization chamber (1606) may be measured by the electrometer. The ionization current may be proportional to a radiation dose received by the ionization chamber and used for absolute and/or relative dosimetry. Accordingly, absolute dose of the beam (1632) may be calculated and used to calibrate the system (1600) (e.g., radiation source (1630)).

As shown in FIG. 16A, each of the ionization chambers (1606) and dosimeter slots (1608) may be substantially in a plane of its corresponding step (1604). That is, each of the ionization chambers (1606) may be disposed at the predetermined depth of its corresponding step (1604) along a longitudinal axis of the phantom (1602). This allows dose data generated using the ionization chambers (1606) to be calibrated against one or more of dose data generated using the steps and radiation detector (1640), dose data generated using radiographic films, and/or dose data generated using other dosimeters. For example, dose data generated from an electrometer coupled to the ionization chambers (1606) may be used to calculate absolute dose at a predetermined depth of the phantom (1602). In some variations, the ionization chamber (1606) may comprise a parallel-plate chamber, cylindrical chamber, well-type chamber, free-air chamber, vented chamber, sealed chamber, combinations thereof, and/or the like.

As shown in FIG. 16B, ionization chambers (1606) in some variations may be arranged along a longitudinal axis (i.e., X-axis) of the phantom (1602) and along a vertical axis (i.e., Z-axis). In this manner, beams (1632) emitted parallel to the Z-axis may intersect a single ionization chamber without interference from another ionization chamber, thus reducing cross-talk and/or cavity effects due to attenuation changes from gas within another ionization chamber. In some variations, the plurality of ionization chambers (1606) may be within 5 mm of each other along the longitudinal axis (i.e., X-axis).

As shown in FIG. 16A, each of the dosimeter slots (1608) may be disposed at the predetermined depth of its corresponding step (e.g., substantially in a plane of its corresponding step (1604)). The dosimeter slots (1608) may be substantially parallel to the longitudinal axis (i.e., X-axis) and arranged along the vertical axis (i.e., Z-axis). In some variations, one or more dosimeter slots may be used to measure beam scatter of the radiation source (1630). For example, a vertical dosimeter slot (1609) may be disposed parallel or nearly parallel to the vertical axis. For example, the vertical dosimeter slot (1609) may be angled between about 2 degrees and about 10 degrees relative to the vertical axis (i.e., Z-axis). The slots (1608, 1609) may comprise one or more shapes including rectangular, square, trapezoidal, oval or elliptical, arc-shaped (e.g., hemi-arc, hemi-spherical, hemi-cylindrical), combinations thereof, and the like. The slots (1608, 1609) may define an opening having a height sufficient to hold a radiographic sheet at a predetermined depth of the phantom (1602). In some variations, one or more radiographic sheets (e.g., radiographic film) may be disposed between one or more of the dosimeter slots (1608, 1609). The radiographic sheets may be used to acquire radiation dose measurements. Data from the radiographic sheets may have a high spatial resolution and may be digitized for analysis. For example, the radiographic sheets may be used to calculate the amount of dose applied to the phantom (1602) and/or used to generate a dose map. The dose map may be compared to the predicted dose to identify any dose deviations. In some variations, a calibration curve may be generated using dose data from the radiographic sheets. Accordingly, the operation of one or more of the linac, gantry, and the multi-leaf collimator may be validated and/or characterized based on the radiation dose data and/or dose map acquired using the radiographic sheets and/or radiation detectors.

Figure 17:
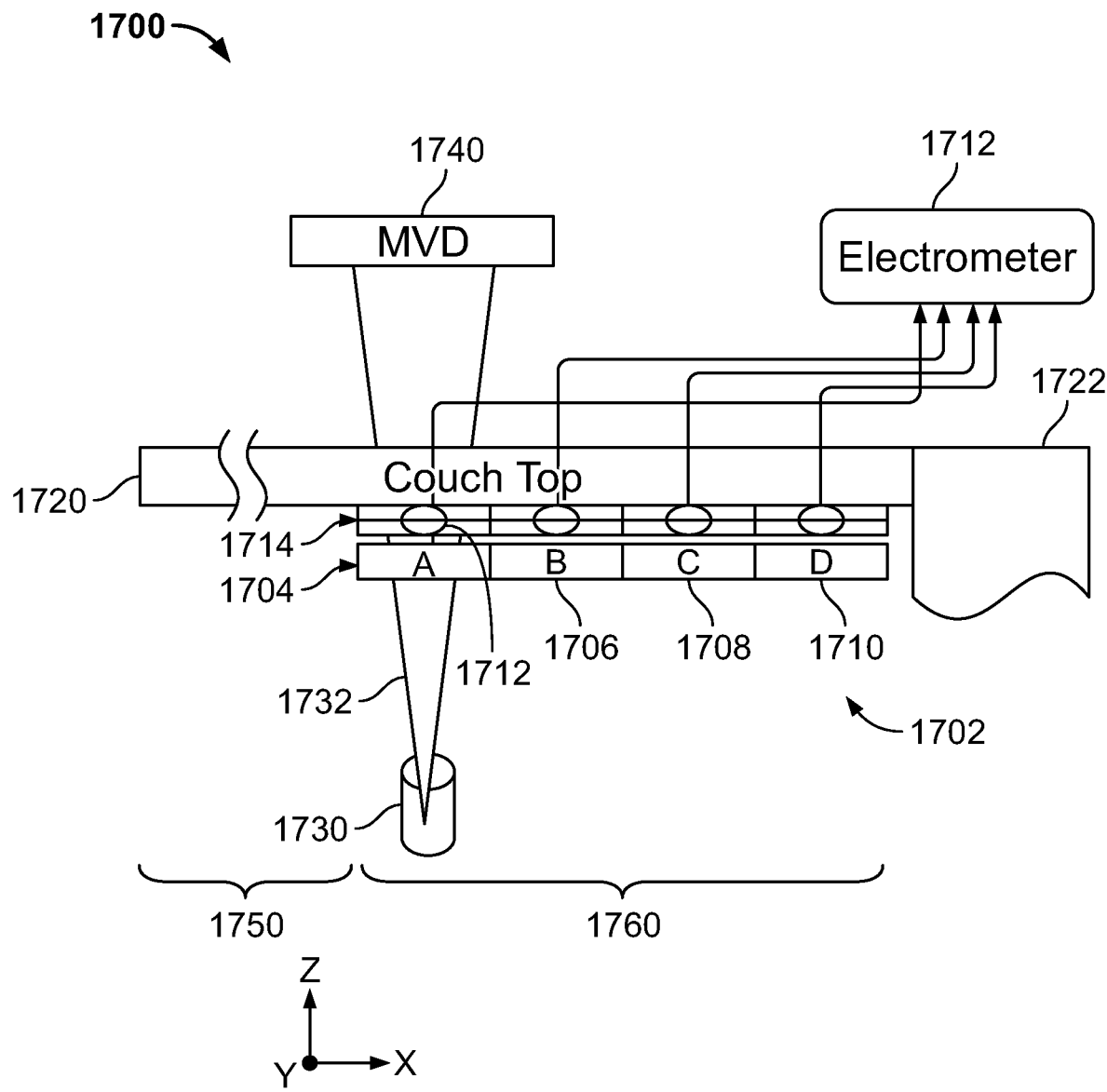
FIG. 17 is an illustrative cross-sectional side view of a variation of a phantom for a radiotherapy system.

FIG. 17 depicts a cross-sectional side view of another variation of a patient platform (1720) comprising a phantom (1702) for a radiotherapy system (1700). For example, FIG. 17 depicts a radiotherapy system (1700) comprising a phantom (1702) coupled (e.g., mounted) to an underside of a patient platform (1720). The patient platform (1720) may have a patient support surface configured to hold a patient thereon (e.g., the surface of the platform that faces the radiation detector (1740) in FIG. 17) with the underside surface disposed opposite the patient support surface (e.g., the surface of the platform that faces the radiation source (1730) in FIG. 17). The patient platform (1720) may define a longitudinal axis parallel with the X-axis. The patient platform (1720) is not drawn to scale (e.g., the patient region (1750) is relatively short in FIG. 17) for the sake of illustration. A radiation source (1730) and a radiation detector (1740) may be disposed on a gantry (not shown for the sake of clarity) relative to the patient platform (1720) so as to generate a beam that intersects the patient platform (1720) and phantom (1702). The phantom (1702) may be disposed within a phantom region (1760) of the patient platform (1720) that is outside a patient region (1750). That is, the patient region (1750) and not the phantom region (1760) may be positioned to intersect a beam plane of the radiation source (1730) during a treatment session. The patient region has a longitudinal length that is greater than the longitudinal length of the phantom region (FIG. 17 is not drawn to scale; the phantom region has been enlarged). The patient platform (1720) may be advanced such that the beam plane intersects the phantom region (1760) only during a quality assurance procedure. In some variations, a patient platform may have a patient region that is distal to the phantom region, and the patient region and phantom region are non-overlapping.

The phantom (1702) may comprise a housing having a plurality of regions arranged along the longitudinal axis. For example, the phantom (1702) may comprise two or more regions having different attenuation characteristics used to generate dose data corresponding to at least two or more predetermined depths of a water-filled phantom when respective beams (1732) pass through each region. The dose data of the regions may be used for absolute and/or relative dosimetry calculations. In some variations, dose data generated by the detector (1740) may be calibrated against one or more of dose data generated using the ionization chambers (1712), dose data generated using radiographic films, and/or dose data generated using other dosimeters. In some variations, the density regions (1704, 1706, 1708, 1710) may be spaced along either a longitudinal (i.e., along the X-axis) or a lateral axis (i.e., along the Y-axis) of the patient platform (1720).

As shown in FIG. 17, the phantom (1702) may comprise a first region (1704), second region (1706), third region (1708), and fourth region (1710) having respective densities (A, B, C, D). In some variations, the phantom (1702) may comprise 2, 3, 4, 5, 6, 7, or more density regions. For example, the phantom (1702) may comprise four or five regions each having the same thickness, but comprising different density material. In one variation of a phantom comprising four regions of the same thickness, the first region (1704) may comprise a mass per area of about 1.5 g/cm$^2$, the second region (1706) may comprise a mass per area of about 5 g/cm$^2$, the third region (1708) may comprise a mass per area of about 10 g/cm$^2$, and the fourth region (1710) may comprise a mass per area of about 20 g/cm$^2$. In another variation of a phantom comprising three regions of the same thickness, the first region (1704) may comprise a mass per area of about 1.5 g/cm$^2$, the second region (1706) may comprise a mass per area of about 10 g/cm$^2$, and the third region (1708) may comprise a mass per area of about 20 g/cm$^2$. Alternatively, each region may have a density and thickness different from the other regions of the phantom (1702).

Each density region may comprise a thickness (i.e., along the Z-axis) of at least about 5 mm or more. The phantom (1702) may comprise a width (i.e., along the Y-axis) of at least about 2 cm. Each region of the phantom (1702) may have a length between about 2 cm and about 5 cm. The variable density regions of the phantom (1702) may comprise a material such as lead, copper, steel, acrylic, tungsten, uranium, combinations thereof, and the like. In one variation, the first region (1704) may comprise acrylic, the second region (1706) may comprise aluminum, the third region (1708) may comprise copper or steel, and the fourth region (1710) may comprise lead. In some variations, the region with the highest-density material may be located at a greater distance away from the other regions, so that scattered radiation from the highest-density region does not interfere with the dose data of the other regions.

In some variations, the phantom (1702) may further comprise a plurality of radiation detectors (1712, 1714) arranged along the longitudinal axis. For example, as depicted in FIG. 17, each density region (1704, 1706, 1708, 1710) having a respective ionization chamber (1712) and dosimeter slot (1714). The ionization chamber (1712) and dosimeter slot (1714) may be similar to those described herein with respect to FIGS. 16A-16B. In some of these variations, a dosimeter slot (1714) may be arranged to intersect its corresponding ionization chamber (1712). In some of these variations, an ionization chamber plug may be inserted into the ionization chamber (1712) when a radiographic sheet is loaded into the dosimeter slot (1714) and the ion chamber (1710). In other variations, the dosimeter slot (1714) and ionization chamber (1712) of a density region (1704, 1706, 1708, 1710) may be spaced apart along the longitudinal and/or lateral axis. In some variations, the radiation detectors (1712, 1714) may be disposed in a region of the phantom (1702) comprising a material such as acrylic (e.g., polymethylmethacrylate (PMMA)) that may be dosimetrically similar to water. The radiation detectors (1712, 1714) may be disposed above, below, and/or between the density regions (1704, 1706, 1708, 1710). In some variations, each density region (1704, 1706, 1708, 1710) may comprise a predetermined depth (e.g., about 5 cm) and provide different attenuation for a beam (1732) emitted from the radiation source (1730), thereby generating dose data corresponding to different depths.

The phantoms described herein may have a variety of shapes, as may be desired, and may be cylinder-shaped, disk-shaped, oblong-shaped, etc. In some variations, the phantom may be disposed on a patient support surface of the patient platform. In some variations, the ionization chamber (1712) may comprise a parallel-plate chamber, cylindrical chamber, well-type chamber, free-air chamber, vented chamber, sealed chamber, combinations thereof, and/or the like. The slots (1714) may comprise one or more shapes including rectangular, square, trapezoidal, oval or elliptical, arc-shaped (e.g., hemi-arc, hemi-spherical, hemi-cylindrical), combinations thereof, and the like. The slots (1714) may define an opening having a height sufficient to hold a radiographic sheet at a predetermined depth of the phantom (1702). In some variations, one or more radiographic sheets (e.g., radiographic film) may be disposed between one or more of the dosimeter slots (1714).

In some variations, a patient platform may comprise a phantom that may be used to measure the ability of a radiation detector of a radiotherapy system (e.g., MV detector) to resolve high-contrast edges as well as contrast resolution. For example, a phantom may comprise a set of patterns having variable separation and/or contrast gradients that may allow an operator and/or the radiotherapy system to determine the upper limit of spatial frequency and contrast resolution of the detector. In one variation, a phantom may comprise a first region having high-contrast stripes with varied spatial frequencies and a second region with shapes having varied intensity or contrast levels relative to a background intensity. That is, the first region may comprise a pattern with a constant intensity or contrast level, but with variable spatial frequencies to measure the ability of the detector to resolve edges (e.g., a series of stripes where the distance between them varies and/or the stripe thickness varies). The second region may comprise a pattern with a constant spatial frequency (e.g., ovals of the same size), but with variable intensity or contrast levels relative to a background intensity to measure the ability of the detector to resolve differences in intensity or contrast. In this manner, a spatial frequency and contrast resolution of one or more detectors (e.g., MV and/or kV) may be determined. The measured resolution may be compared to the expected (e.g., calibrated) detector resolutions. As discussed in more detail herein, a fault signal may be generated when the measured resolution differs from a reference resolution by a predetermined criteria. In some variations, the phantom may be mounted to an underside of the patient platform in a similar manner as described herein with respect to FIGS. 16A-16B and 17.

Figure 18:
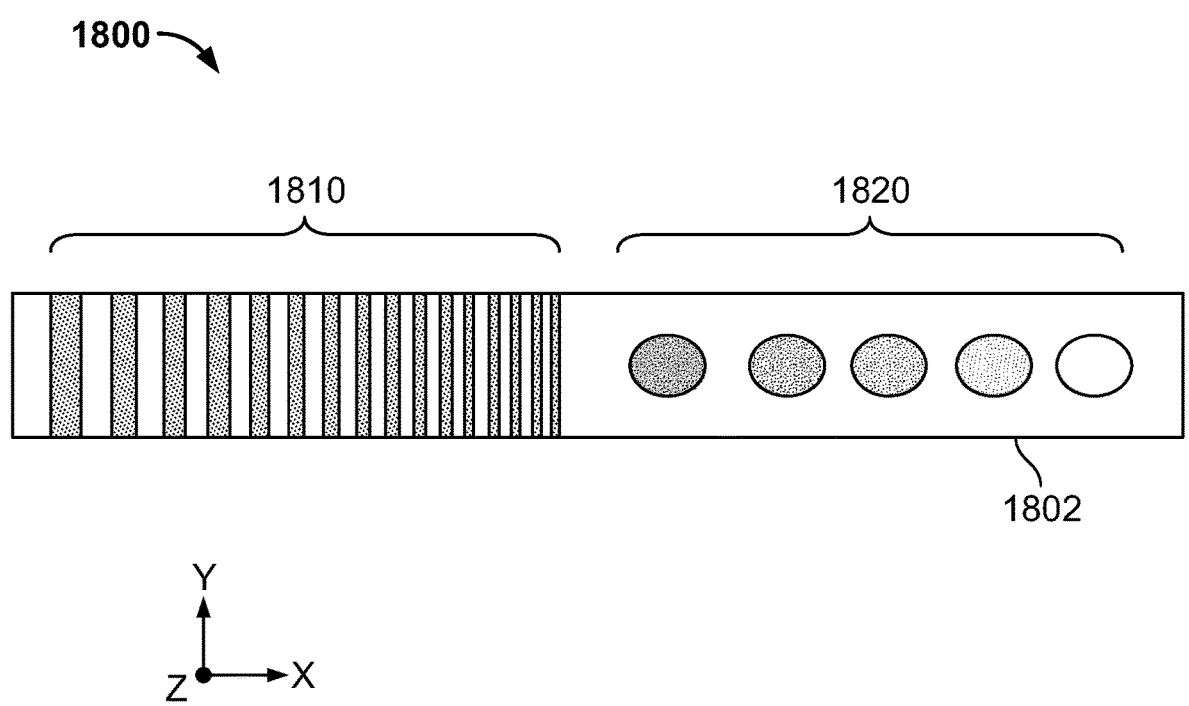
FIG. 18 is an illustrative plan view of a variation of a phantom for a radiotherapy system.

The phantom (1800) may include patterns that are within and beyond (e.g., above and below) the upper resolution capabilities of the radiation detector to be verified and/or calibrated. FIG. 18 depicts a plan view of a variation of a phantom (1800) having a housing (1802) comprising a first repeated pattern (1810) having a spatial frequency range and a second repeated pattern (1820) having a contrast range. In particular, the spatial frequency range may be configured to be within and greater than an upper spatial frequency limit of a radiation detector and the contrast range may be configured to be within and greater than an upper contrast limit of the radiation detector. The first repeated pattern (1810) and the second repeated pattern (1820) may be spaced along a longitudinal axis (i.e., X-axis) of the phantom (1800). The housing (1802) may comprise a material such as acrylic (e.g., polymethylmethacrylate (PMMA)) or other plastic that may be dosimetrically similar to water.

The first repeated pattern (1810) and the second repeated pattern (1820) may each comprise a set of contrasting shapes spaced apart at different intervals. When imaged by a radiation detector, the set of bars and ellipsoids may generate detector data (e.g., image data). In some variations, the first repeated pattern (1810) may comprise a set of rectangular bars having variable separation along a longitudinal axis of the phantom (1800). In some variations, the second repeated pattern (1820) may comprise a first shape having a first thickness (e.g., dark ellipsoid) and a second shape having a second thickness (e.g., lighter ellipsoid) different from the first thickness. Additionally or alternatively, the first shape (e.g., dark ellipsoid) may have a first density and a second shape (e.g., light ellipsoid) may have a second density different from the first density. The first and second shapes may comprise a material such as lead, copper, steel, acrylic, tungsten, uranium, combinations thereof, and the like.

In some variations, the repeated patterns may comprise one or more shapes including rectangular, square, trapezoidal, oval or elliptical, arc-shaped (e.g., hemi-arc, hemispherical, hemi-cylindrical), combinations thereof, and the like. The housing (1802) may have a variety of shapes, as may be desired, and may be cylinder-shaped, disk-shaped, oblong-shaped, etc. In some variations, the phantom (1800) may be disposed on a patient support surface of the patient platform.

In some variations, the phantom (1800) may comprise 1, 2, 3, 4, 5, or more repeated patterns. For example, the phantom (1800) may comprise four repeated patterns to allow spatial frequency resolution and contrast resolution to be determined for MV CT and kV CT detectors. In some variations, the phantom (1800) may comprise a width (i.e., along the Y-axis) of between about 2 cm and about 5 cm. For example, the phantom (1800) may comprise a width of between about 3 cm and about 4 cm. In some variations, the phantom (1800) may comprise a length (i.e., along the X-axis) of between about 10 cm and about 25 cm. For example, the phantom (1800) may comprise a length of between about 15 cm and about 20 cm. In some variations, the phantom (1800) may comprise a height (i.e., along the Z-axis) of at least about 0.2 cm. For example, the housing (1802) of the phantom (1800) may comprise a height of between about 0.5 cm and about 2 cm.

In some variations, a width of the phantom (i.e., along the Y-axis) may be aligned parallel to a length of the patient platform. In this manner, a single beam emitted from a radiation source (not shown) may be used to image both the first and second repeated patterns (1810, 1820) of the phantom (1800).

In some variations, the phantoms as described herein (e.g., phantoms (1602, 1702, 1800)) may be used for energy measurement, calibration, and/or verification procedures using one or more radiation detectors and types. Any of the phantoms and associated systems described herein may be used in the methods described herein. The phantoms as described herein may be disposed on top of or below a patient platform. In some variations, the phantom may slide out laterally using a mount disposed underneath the patient platform. The mount may allow an operator to prepare the phantom for a calibration procedure and may be configured to slidably position the phantom relative to the patient platform. For example, the mount may comprise a set of hand-retractable and/or motor-driven rails. In some variations, the mount may comprise an electrical and/or mechanical interlock configured to prevent operation of the patient platform and/or radiation source when the phantom is retracted relative to the patient platform. For example, a set of ionization chambers may be connected to an electrometer, a set of radiographic sheets may be inserted into corresponding dosimeter slots, and the phantom may be filled with water. In some variations, one or more ionization chambers may be loaded from a side of the phantom. Radiographic sheets disposed in respective slots may form a stack that allows depth dose measurements to be acquired. In other variations, the phantom may be fixed relative to the patient platform.

After configuring (e.g., loading) the phantom, the patient platform may be moved to a predetermined position relative to a radiation source and detector. The radiation source and detector may be positioned at a predetermined gantry angle relative to the patient platform and phantom. For example, FIG. 16A illustrates the radiation source (1630) and radiation detector (1640), and the patient platform located at a position such that a beam (1632) emitted by the radiation source (1630) irradiates a first step (1604) of the phantom (1602). Dose data acquired by the detector (1640) based on the beam (1632) may be stored in a memory of a controller along with data including patient platform position, gantry position, step depth, and corresponding reference data. After acquiring dose data at a first phantom position using one or more radiation detectors, the patient platform (1620) may be moved longitudinally to generate dose data at other phantom depths and/or using other radiation detectors.

In some variations, dose data (e.g., dose-to-water values) may be acquired by radiographic sheets disposed in the slots of the phantom and compared to a set of reference dose data for calibration. For example, calibrated dose intensity values may correspond to a dose received by a patient and used in offline or online dose reconstruction. In variations of the phantom comprising a set of variable density regions, detector data may be used to generate an beam width intensity profile. A peak value of the intensity profile may be set as the dose value of a corresponding ion chamber. TPR values may be calculated and compared to reference TPR values. Reference TPR values may be determined during machine acceptance testing and/or beam commissioning. The tissue phantom ratio does not depend on absolute calibration of a radiation detector since variations in a calibration factor and/or radiation detector gain cancel out. Additionally or alternatively, the dose data may be used to characterize the stability of a radiotherapy beam. For example, beam stability may be determined during a daily quality assurance procedure.

A fault signal may be generated when the measured dose data deviates from the reference dose data based on a predetermined criteria. For example, a fault signal may be generated by a processor when a set of dose data measured by the detector, ionization chambers, and/or radiographic sheets exceeds a threshold parameter. A radiotherapy system may respond in one or more ways in response to the generation of a fault signal. For example, the system may deactivate one or more of the radiation source and radiation detector, output the fault signal to an operator, inhibit a radiation therapy treatment procedure, and calibrate the system using the calibration data. In some variations, the system may verify the fault signal and then recalibrate the system as necessary. One or more radiation detectors may be calibrated by a processor using the dose data.

In variations of a phantom comprising one or more repeated patterns, dose data generated by a radiation detector may be used to generate an image of each repeated pattern using a single beam. An operator and/or processor may identify within the first repeated pattern (1810) and second repeated pattern (1820) the smallest identifiable difference between the shapes to thereby determine the high and low contrast resolution of the radiation detector.

In some variations, one or more visual, audio, and tactile sensory output systems coupled to the system may be used to output a fault signal and/or detector resolution to a user such as an operator. For example, a display coupled to the system may display the fault signal, dose data calculations, and resolution to an operator while an audio device may output an audible set of fault beeps and/or a verbal message. Additionally or alternatively, the fault signal and/or detector resolution may be stored in memory and/or transmitted over a network to be output and/or displayed to one or more of a remote operator, system vendor, regulatory agency, and/or stored in a database.

Handheld Controller

Figure 5:
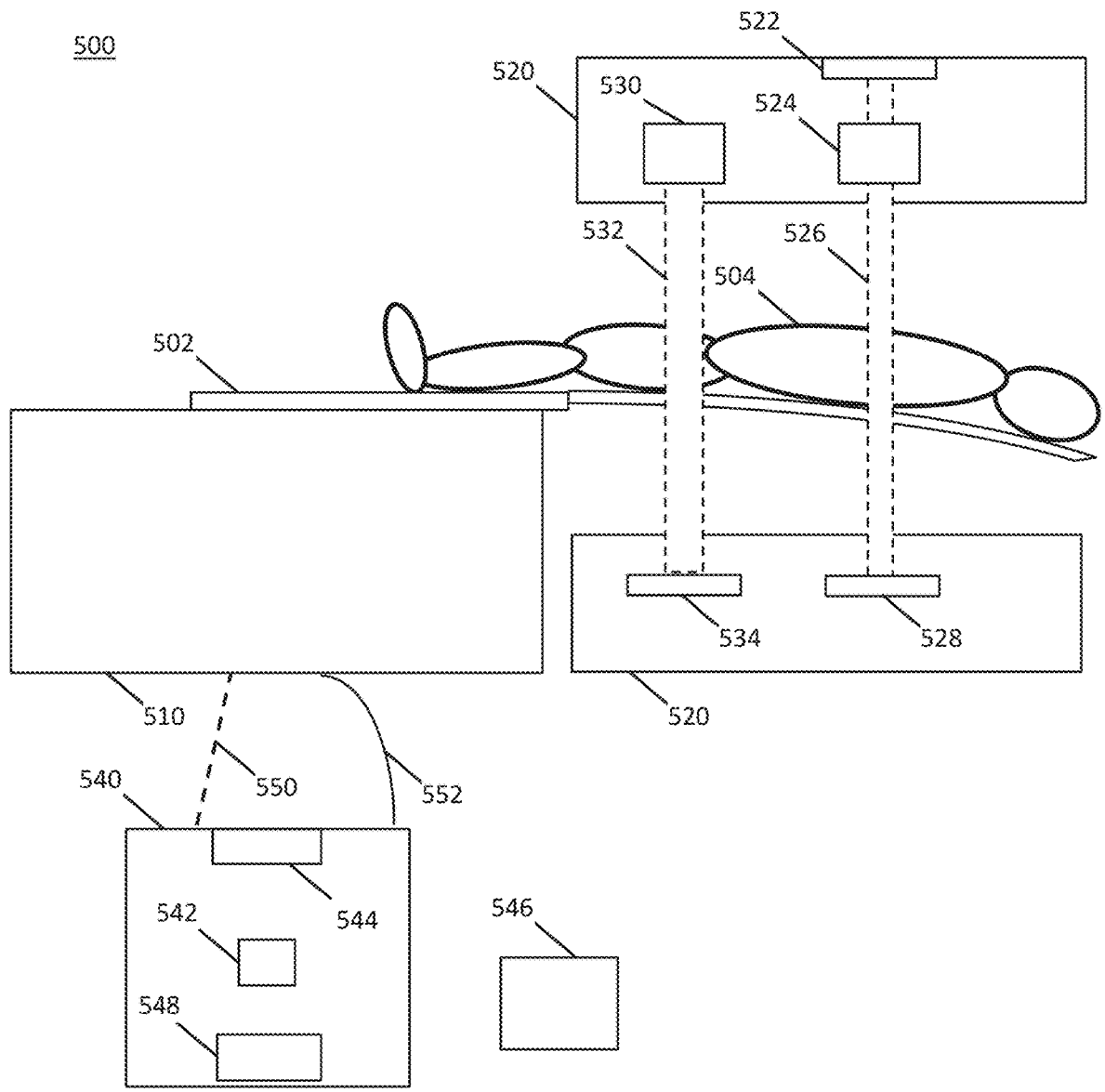
FIG. 5 is an illustrative cross-sectional side view of a variation of a handheld controller for a radiotherapy system.

Generally, the patient platform systems described here may comprise a handheld, portable controller to control movement of a patient platform. FIG. 5 is a cross-sectional side view of a patient platform system (500). The system (500) may comprise a patient platform (502) coupled to a base (510). A patient (504) may be provided onto the patient platform (502). The system (500) may comprise a gantry (520) having a first radiation source (522) and a second radiation source (530). The first radiation source (522) may be coupled to a multi-leaf collimator (524) and may be provided opposite a first detector (528). The first radiation source (522) may be configured to emit a first beam (526). The second radiation source (530) may be provided opposite a second detector (534) and may be configured to emit a second beam (532). For example, the first radiation source (522) may be a radiation therapy source and the second radiation source (530) may be an imaging source.

A handheld controller (540) may be coupled to the system (500) and comprise a first switch (542) and a docking port (544). The first switch (542) may be configured to generate a movement signal of the patient platform (502). In some variations, the first switch (542) may comprise at least one of a button, an analog stick, a trackball, a touch screen, a directional pad, a jog dial, a motion detector, an image sensor, and a microphone.

In other variations, the controller (540) may further comprise a proximity sensor (548) configured to detect a proximity of the controller (540) to the patient platform (502) or other predetermined location. In some of these variations, the patient platform (502) may be configured to move using the movement signal and the detected proximity. For instance, control of the patient platform system (500) by the controller (540) may be limited to the room where the system (500) is located and/or specific areas within the room.

The docking port (544) may be dockable with one or more of the gantry (520), and patient platform (502), and user console. The controller (540) may be configured to generate different sets of output signals using a docking state of the controller (540). For instance, the controller (540) may output a gantry movement signal only when undocked from the system (500), and radiotherapy treatment may be executed only when the docking port (544) of the controller (540) is docked to the system (500).

In some other variations, the controller (540) may comprise a wireless transmitter outputting the movement signal (550). In other variations, the controller (540) may be wired to the system (500) to transmit the movement signal (550). In some of these variations, the movement signal (550) may control at least four degrees of freedom of motion, and may include yaw and/or pitch rotation.

Additionally or alternatively, the controller (540) may comprise a tether (552) for physically coupling the controller (540) to the system (500). It should be appreciated that the controller (540) may comprise a plurality of switches. Furthermore, some portions of the controller (540) may be handheld and/or portable while other portions may be stationary. For example, the controller (540) may comprise a second switch (546) such as a step switch or foot pedal in a housing separate from the first switch (542). The second switch (546) may in some variations be a safety switch that must be engaged before a movement signal of the first switch (542) may be outputted by the controller (540). In other variations, the controller (540) may comprise a housing having the first switch (542) on a first side of the housing and the second switch (546) on a second side of the housing opposite the first side. For instance, the controller (540) may be configured for activation with one hand by a thumb on the first switch (542) and a finger on the second switch (546). It should be appreciated that the shape of the controller (540) is not particularly limited. For example, the controller (540) may be pendant-shaped.

Head Fixation Device

Generally, the head fixation devices described here may fix or temporarily hold a patient's head in a desired position during radiotherapy treatment. FIGS. 6A-6B are side views of a patient platform system (600) comprising a head fixation device (610) and a patient platform (602). The head fixation device (610) may comprise a hinge (614) coupled to a base (612), a head rest (616) coupled to the hinge (614), and a drive system (618) coupled to the head rest (616). The head rest (616) may be configured to hold a patient's head in a plurality of angled positions. In some variations, the head rest (616) may rotate about the hinge (614) such that the head rest (616) may pitch and yaw relative to the base (612).

In some variations, the hinge (614) may comprise a lock having a plurality of detents and pins forming a plurality of lockable positions. Accordingly, the head rest (616) may be locked relative to the base (612). In some variations, a patient may manually adjust the position of their head by neck flexion.

In other variations, a patient and/or operator may control a drive system to reposition and lock the head rest (616) in a desired position. The head rest (616) and the drive system (618) may each comprise a radiotransparent material. In some variations, the drive system (618) may comprise a pneumatic element. In other variations, the drive system (618) may comprise an electromechanical or hydraulic element. In still other variations, the drive system (618) may be coupled to an actuator (620) and controller (not shown). For instance, the actuator (620) may be coupled to a first end (603) of the patient platform (602). As shown in FIGS. 6A-6B, extension of the drive system (618) in a direction substantially perpendicular to the base (612) may angle the head to a desired position. The patient and/or operator may control the drive system (618) using the handheld controller to control the rate of movement and position of the head rest (616) until a desired position is reached. Additionally or alternatively, a patient torso and/or a patient shoulder may be coupled to the base (612). The base (612) may be removably attached or fixed to the patient platform (602).

Controller

In some variations, the systems described herein may comprise a controller configured to perform one or more steps of a radiotherapy procedure. The controller may be coupled to one or more of the patient platform and gantry. In some variations, the controller may be disposed in one or more of a patient platform, user console, and the like. For example, a controller may be configured to determine sag of a patient platform, control movement and positioning of the patient platform, and perform one or more steps of a radiotherapy procedure. The controller may comprise one or more processors and one or more machine-readable memories in communication with the one or more processors. The processor may incorporate data received from memory and patient input to control the system. The memory may further store instructions to cause the processor to execute modules, processes and/or functions associated with the system. The controller may be configured to control one or more components of the system, such as a drive system, conformable substrate, imaging system, treatment system, and the like.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on a user console, servers or server computing devices such as routing/connectivity components, multiprocessor systems, microprocessor-based systems, distributed computing networks, personal computing devices, network appliances, portable (e.g., hand-held), and the like.

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types including metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, combinations thereof, or the like.

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, combinations thereof, or the like. As used herein, database refers to a data storage resource. The memory may store instructions to cause the processor to execute modules, processes, and/or functions associated with the system, such as sag determination and/or compensation, patient platform movement, and the like. In some variations, storage may be network-based and accessible for one or more authorized users. Network-based storage may be referred to as remote data storage or cloud data storage. Sensor signal and attachment data stored in cloud data storage (e.g., database) may be accessible to respective users via a network, such as the Internet. In some variations, the database may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and methods described herein may be performed by software (executed on hardware), hardware, or a combination thereof. Hardware modules may include, for example, a general-purpose processor (or microprocessor or microcontroller), a field programmable gate array (FPGA), an application specific integrated circuit (ASIC), or the like. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, near-field communication (NFC), radio-frequency identification (RFID), Wireless Fidelity (Wi-Fi) (e.g., IEEE 802.11a, IEEE 802.11b, IEEE 802.11g, IEEE 802.11n), Voice over Internet Protocol (VoIP), Wi-MAX, a protocol for email (e.g., Internet Message Access Protocol (IMAP), Post Office Protocol (POP)), instant messaging (e.g., eXtensible Messaging and Presence Protocol (XMPP), Session Initiation Protocol for Instant Messaging, Presence Leveraging Extensions (SIMPLE), Instant Messaging and Presence Service (IMPS)), Short Message Service (SMS), or any other suitable communication protocol. Some wireless network deployments combine networks from multiple cellular networks or use a mix of cellular, Wi-Fi, and satellite communication.

In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

II. Methods

Methods of Performing Radiotherapy

Figure 7:
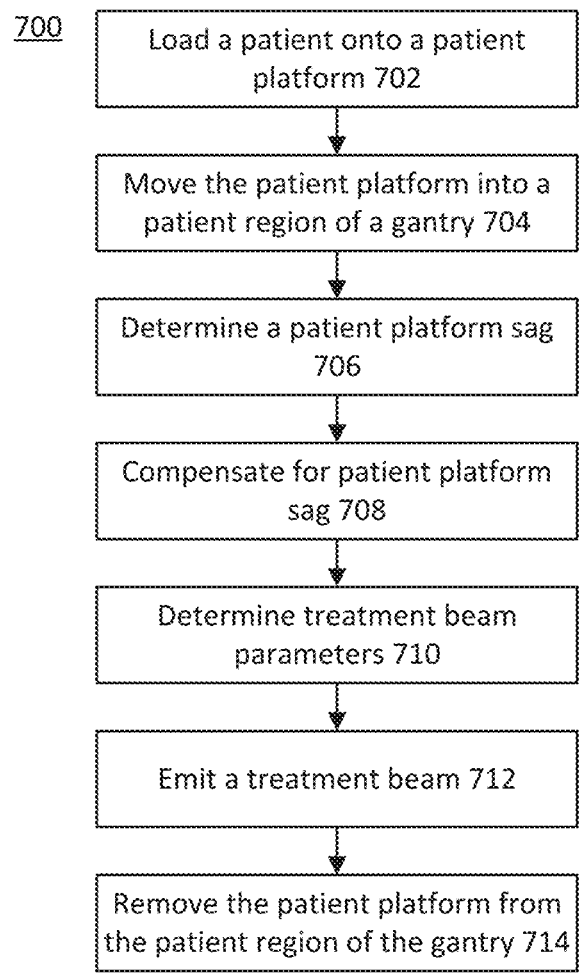
FIG. 7 is a flowchart representation of one variation of a radiotherapy process.

Generally described here are methods for performing radiotherapy. Any of the systems and devices described herein may be used in the radiotherapy procedures described below. FIG. 7 is a flowchart that generally describes a radiotherapy process (700) including sag determination and compensation. The process (700) may include loading a patient onto a patient platform (702). In some variations, patient loading may comprise securing one or more portions of the patient relatively comfortably so that they remain substantially in place relative to the patient platform. As discussed further in FIG. 10, a conformable substrate of the patient platform may be controlled to couple a patient to the patient platform to increase patient compliance with radiotherapy treatment. In some variations, the height of the conformable substrate may be independently controlled to contour the patient platform to the patient's shape (e.g., FIGS. 2A-2C). Patient platform settings for each patient may be stored in memory and reapplied for efficiency and repeatability across one or more patient platforms and/or radiotherapy systems and across treatment sessions.

Additionally or alternatively, a patient platform may be contoured to a patient's body shape through heating and cooling of a thermoelectric layer. In yet other variations, as discussed with respect to FIGS. 6A-6B and further in FIG. 14, a patient head may be coupled by a head fixation device to a patient platform in a fixed position. During adjustment of the head fixation device, the patient may control the pivoting of the head through neck flexion to improve patient comfort and compliance.

Once a patient is loaded onto the patient platform, the patient platform may be moved into a patient region of a gantry (704). In some variations, as discussed with respect to FIGS. 3A-3D and further in FIGS. 11A-11B, the patient platform may comprise a plurality of portions that may move or telescope in an axial direction relative to each other. An upper portion of the patient platform may be formed of a radiotransparent material while a lower portion may be formed of a stiffer material that is radiopaque and that exhibits less sag than the radiotransparent material. The patient platform may be moved into the patient region such that the radiopaque portion does not cross the plane of an imaging beam and/or treatment beam when either or both of these beams are activated. Accordingly, the length of the radiotransparent upper portion cantilevered from a base may be reduced to reduce an amount of sag of the patient platform. In some variations, the upper portion may have a length of 0.25-2.0 meters.

In other variations, as discussed further in FIGS. 12 and 13A-13E, the patient platform may be moved to align one or more regions of interest of a patient (e.g., lesion, tumor) to an isocenter of a gantry to ensure that a radiation dose is delivered to the region of interest. In particular, as used herein in reference to imaging and radiation oncology, the isocenter is the point in space through which a plurality of beamlets intersect, the plurality of beamlets being emitted from a plurality of gantry locations by a rotating radiation source. The patient platform may translate (axially and/or laterally) and rotate (pitch and/or yaw) to position a region of interest on an isocenter to provide a desired radiation dose.

In yet other variations, as discussed in further detail below, patient platform sag may be determined (706), compensated for (708) and used to determine or revise treatment beam parameters (710) such as power, duration, location, etc. (e.g., treatment plan). In some variations, as discussed with respect to FIGS. 1A-1F, an imaging beam may be emitted towards a sagging patient platform and used to determine a difference between an unweighted position and weighted position of the patient platform. For example, the patient platform may be imaged prior to loading a patient to determine a position of the unweighted patient platform. A change in location of the patient platform may be determined and then used to determine a change in location of the patient and one or more regions of interest. In some instances, the change in location of the patient platform may be used to compensate for the patient platform sag (708). For example, the treatment plan may be modified, adjusted, and/or updated to compensate for the determined sag. Alternatively or additionally, a height and/or position of the patient platform may be adjusted (e.g., raised or lowered) to compensate for the sag of the patient platform in the treatment beam plane.

Once the patient platform is in a desired position and the treatment plan parameters have been updated or adjusted to compensate for sag (if needed), a treatment beam may be emitted (712) according to the treatment plan. After execution of the treatment plan, the patient platform may be removed from the patient region of the gantry (714).

Determine Sag of a Patient Platform

Figure 8:
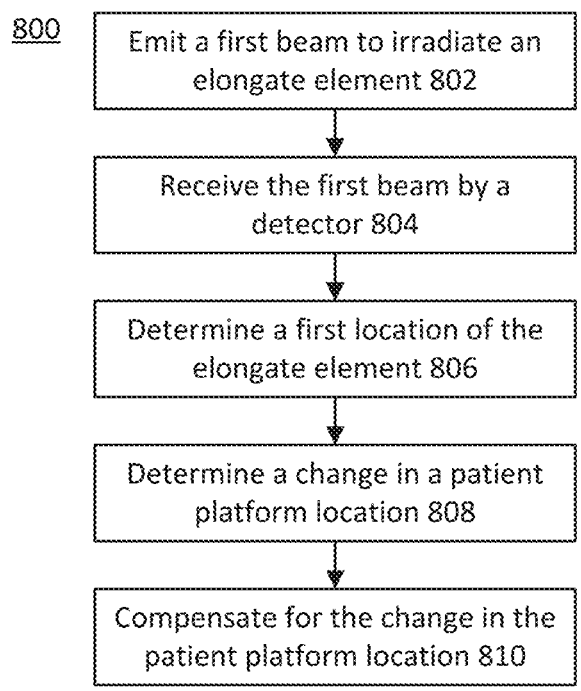
FIG. 8 is a flowchart representation of one variation of a patient platform sag determination process.

FIG. 8 is a flowchart of one variation of a patient platform sag determination process (800). This method may be used with, for example, the systems depicted in FIGS. 1A-1F, where the patient platform is coupled to an elongate element and/or optical marker. The process may include emitting a first beam by a radiation source through a collimator to irradiate an elongate element coupled to the patient platform (802). The first beam may be directed toward the elongate element without intersecting the patient in order to limit exposure to the patient. The first beam may be received by a detector (804) that is located opposite the radiation source and collimator. Alternatively, an optical sensor may receive light reflected from an optical marker. A controller using the received detector data may then determine a first location of the elongate element within the imaging beam plane (806) corresponding to the unweighted patient platform. In some variations, the patient platform sag determination may be performed prior to the patient receiving radiotherapy treatment. However, patient platform sag determination may be determined during radiotherapy treatment as necessary for recalibration.

Figure 9:
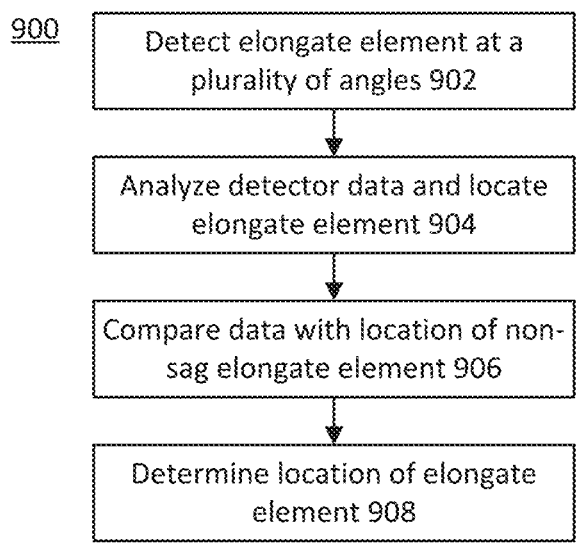
FIG. 9 is a flowchart representation of one variation of an elongate element location determination process.

FIG. 9 is a flowchart of one variation of a process (900) that describes in more detail the step of determining a location of the elongate element and/or optical marker (806) using a Winston-Lutz based method. The elongate element and/or optical marker may be detected at a plurality of angles to generate detector data that indicates the location of the elongate element and/or optical marker (902). For instance, the elongate element may be imaged at a set of cardinal angles (e.g., 0°, 180°, 270°) and/or other angles. The image data may be analyzed by a processor to locate the elongate element and/or optical marker (904). The image data may then be compared to reference data corresponding to the elongate element and/or optical marker of an unweighted platform (906).

Such reference data may be acquired, for example, before the patient is loaded onto the platform, and/or may be reference data acquired and stored during calibration and/or setup procedures. The differences between the data may then be used to determine the location of the elongate element and/or optical marker (908) and the degree to which it has changed from the reference location of the elongate element and/or optical marker (i.e., sag). Turning back to FIG. 8, a relationship between the location of the elongate element and/or optical marker and the patient platform may be known or previously determined. Accordingly, a change in a patient platform location (808) between an unweighted and weighted state may be determined. Accordingly, a change in the location of one or more regions of interest of a patient may be determined based on the sag of the patient platform. Additionally or alternatively, the position of the patient platform and/or treatment plan may be modified to compensate for the sag of the patient platform (810).

Load Patient onto Patient Platform

Figure 10:
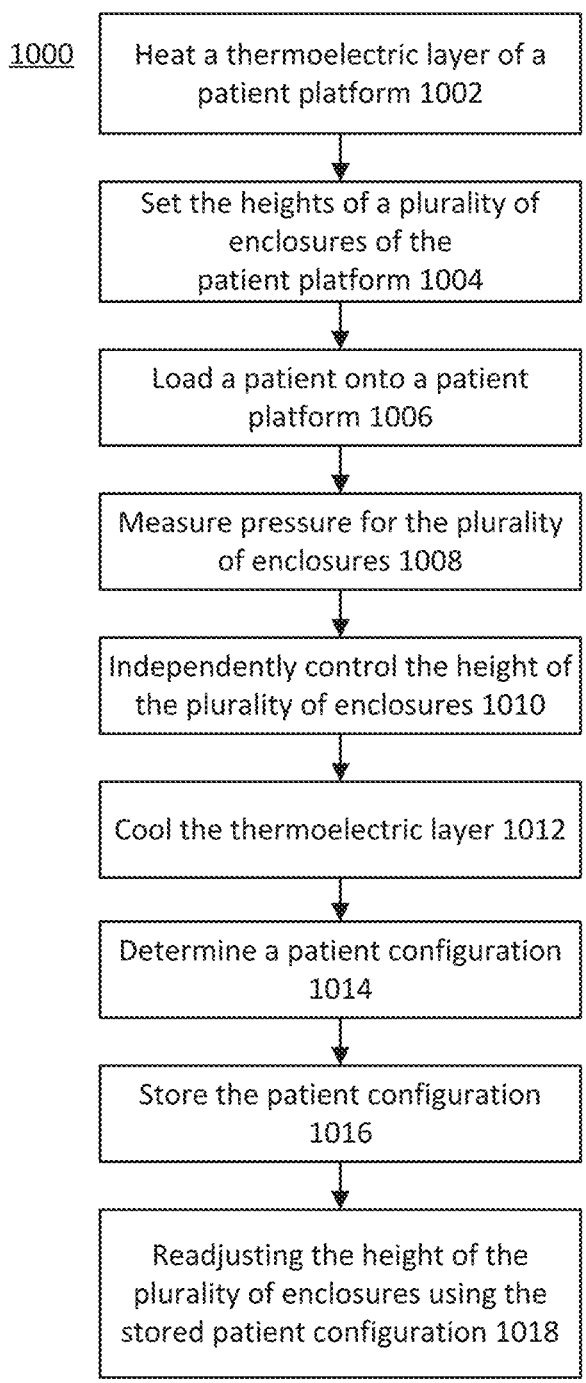
FIG. 10 is a flowchart representation of one variation of a patient platform loading process.

FIG. 10 is a flowchart of one variation of a patient platform loading process (1000). This method may be used with the system depicted in FIG. 2C. The method (1000) may include heating a thermoelectric layer of a patient platform (1002). The thermoelectric layer may be heated to form a compliant configuration for a patient to lay on. The thermoelectric layer of the patient platform may then be modified through patient body weight to form an ergonomic surface. In other variations, the patient platform may comprise a conformable substrate having a plurality of enclosures. In some variations, the loading process (1000) may begin with the heights of the plurality of enclosures being set to a predetermined height (1004) based on a previous fitting for the patient or based on predetermined data for the patient's height and weight. A patient may then be loaded onto a patient platform (1006). In some instances, the patient lays down on the patient platform in a predetermined direction outside a patient region of a gantry. It should be appreciated that the determination and setting of a patient configuration of the patient platform may occur outside the gantry (e.g., in a patient set-up or waiting area) to reduce the time the patient spends within the gantry, thereby allowing more efficient use of a radiotherapy system.

Once the patient is loaded onto of the patient platform, a pressure of the plurality of enclosures may be measured (1008) using a pressure sensor coupled to the patient platform. The pressure may comprise a plurality of enclosure pressures. The height of each of the plurality of enclosures may be independently controlled using the plurality of enclosure pressures such that the patient platform contours to a shape of the patient (1010). Additionally or alternatively, the thermoelectric layer may be cooled to transition from the compliant configuration to a rigid configuration (1012). In some instances, the heating of the thermoelectric layer may be stopped. In other instances, the thermoelectric layer may be actively cooled to form the rigid configuration. It should be appreciated that the heating and cooling steps (1002, 1012) may not be performed where the patient platform does not have a thermoelectric layer.

In some variations, a patient configuration may be determined (1014) corresponding to the height of each of the plurality of enclosures. The patient configuration may comprise at least one of the pressure and/or height of the plurality of enclosures. The patient configuration may be stored in memory (1016) and/or transferred to one or more other patient platforms and/or radiotherapy systems. Subsequently, the height of the plurality of enclosures may be readjusted using the stored patient configuration (1018). Thus, patient registration time may be reduced to increase efficiency and improve imaging and/or treatment consistency.

Move Patient Platform

Figure 11A:
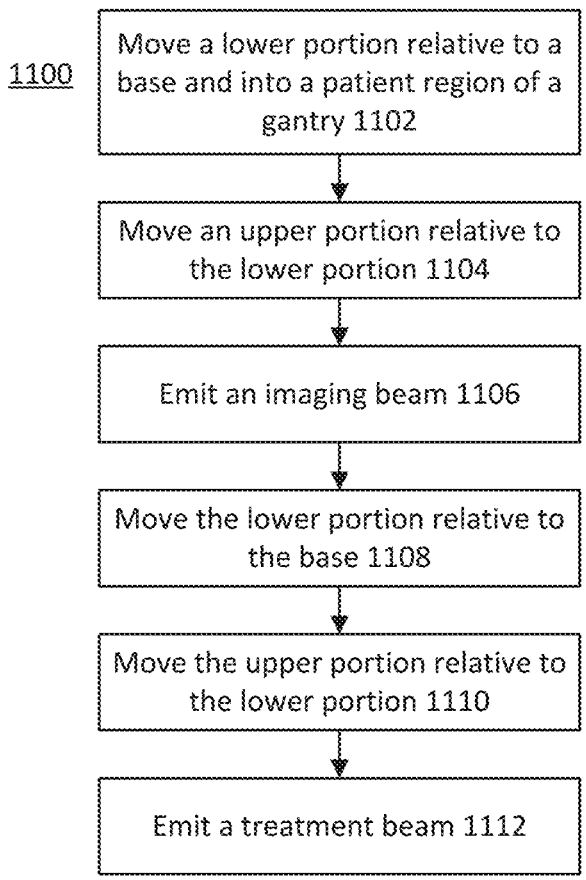
FIGS. 11A-11B are flowchart representations of variations of a patient platform loading process.
Figure 11B:
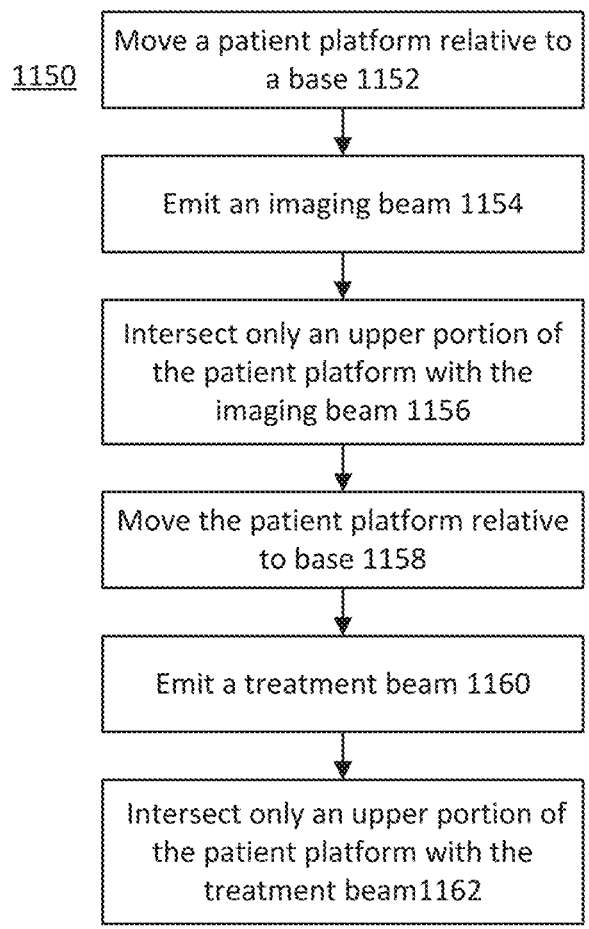

FIGS. 11A-11B are flowcharts of variations of processes (1100, 1150) for moving a patient platform into a gantry to reduce and/or determine sag. In some variations, the methods may be performed by a patient platform coupled to a base. In FIG. 11A, the patient platform may comprise an upper portion and a lower portion coupled to the upper portion where the upper portion and lower portion may move relative to each other. The lower portion may have higher rigidity than an upper portion. In some variations, the upper portion may comprise a radiotransparent first material and the lower portion may comprise a radiopaque second material. The lower portion may comprise any material that is sufficiently rigid to support the upper portion, regardless of its radiopacity and/or radiotransparency.

The process (1100) of FIG. 11A may include moving the lower portion of the patient platform relative to a patient region of a gantry (1102). The upper portion may move relative to the lower portion (1104). An imaging beam may be emitted (1106). In some variations, the imaging beam may be emitted by an imaging radiation source in an imaging plane perpendicular to a longitudinal axis of the patient platform. Movement of the lower portion and upper portion may be such that the lower portion is non-intersecting with the imaging plane and the upper portion intersects the imaging plane. In some of these variations, moving the upper portion into the imaging plane comprises positioning the lower portion such that a leading edge of the lower portion is located at a predetermined first distance away from the imaging plane. The platform may move longitudinally through (e.g., stepped through) the imaging beam across a distance that corresponds to the length of the radiotransparent upper portion that is cantilevered from the lower portion. The imaging beam may capture images of the portion of the patient that is located along the length of the upper portion that is cantilevered from the lower portion.

In other variations, the process (1100) may include moving the lower portion relative to the base (1108) and moving the upper portion relative to the lower portion (1110). A treatment beam may be emitted (1112) from a treatment radiation source coupled to a multi-leaf collimator in a treatment plane perpendicular to a longitudinal axis of the patient platform. The upper portion and the lower portion may be moved such that the lower portion is non-intersecting with the treatment plane and the upper portion intersects the treatment plane. In some of these variations, moving the upper portion into the treatment plane comprises positioning the lower portion such that the leading edge of the lower portion is located at a predetermined second distance away from the treatment plane.

FIG. 11B illustrates another variation of a process (1150) that may be performed by a patient platform coupled to a base. The patient platform may comprise an upper portion and a lower portion fixed to the upper portion. The lower portion of the patient platform may be coupled to the base such that the lower portion may move relative to the base. In some variations, the lower portion may have higher rigidity than the upper portion. The upper portion and the lower portion may comprise materials having different degrees of radiotransparency. For instance, the upper portion may comprise a radiotransparent first material and the lower portion may comprise a radiopaque second material.

The process (1150) of FIG. 11B may include moving the patient platform relative to a base (1152). An imaging beam may be emitted by an imaging radiation source in an imaging plane perpendicular to a longitudinal axis of the patient platform (1154). In some variations, the patient platform is moved such that only an upper portion of the patient platform intersects with the imaging beam (1156). For instance, movement of the lower portion and upper portion may be such that the lower portion is non-intersecting with the imaging plane and the upper portion intersects the imaging plane. In some of these variations, the lower portion may be moved such that a leading edge of the lower portion is located at a predetermined first distance away from the imaging plane. The upper portion may move relative to the lower portion and intersect the imaging plane.

In one variation, the process (1150) may include moving the patient platform relative to the base (1158). A treatment beam may be emitted (1160) by a treatment radiation source coupled to a multi-leaf collimator in a treatment plane perpendicular to a longitudinal axis of the patient platform. In some variations, the patient platform may be moved such that only an upper portion of the patient platform intersects with the treatment beam (1162). For instance, the patient platform may be moved such that the lower portion is non-intersecting with the treatment plane and the upper portion intersects the treatment plane. In some of these variations, the lower portion may be moved such that the leading edge of the lower portion is located at a predetermined second distance away from the treatment plane. The upper portion may move relative to the lower portion and intersect the treatment plane.

Move Region of Interest to Isocenter

Figure 12:
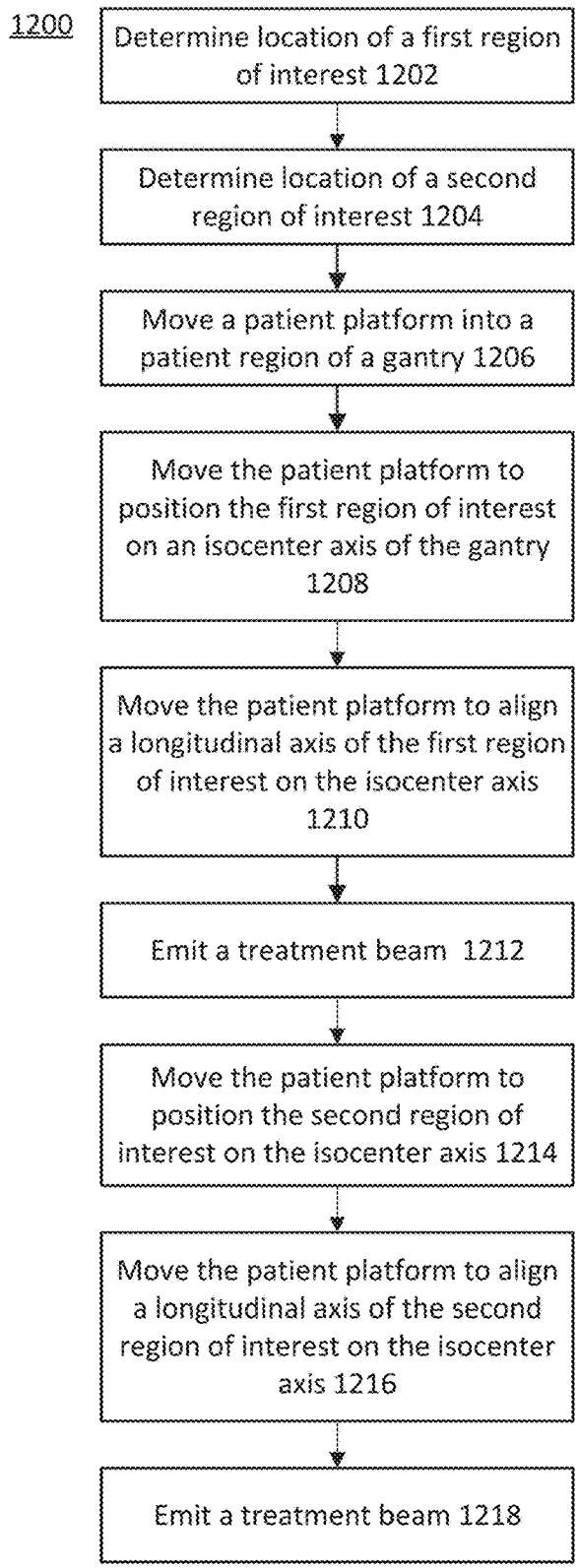
FIG. 12 is a flowchart representation of another variation of a patient platform moving process.

For a radiotherapy procedure, it may be desirable to position the center of a region of interest at the isocenter of a gantry. In the processes described below, one or more regions of interest may be moved to align to an isocenter such as through movement of a patient platform. FIG. 12 is a flowchart of one variation of a patient platform moving process (1200). In some variations, the process (1200) may include determining a location of a first region of interest (1202) of a patient on a patient platform. In some of these variations, a location of a second region of interest may be determined (1204). The patient platform may then be moved into a patient region of a gantry (1206), as illustrated in exemplary FIG. 13A. The gantry may define an isocenter point about which the gantry rotates and an isocenter axis comprising the isocenter point and extending in parallel with a longitudinal axis of the patient region. FIG. 13A illustrates a patient platform system (1300) comprising a patient platform (1310) moved into a patient region of a gantry (1330). The gantry (1330) may comprise a radiation source (1332) coupled to a multi-leaf collimator (1334). A treatment beam (1336) may be emitted by the radiation source (1332). A patient (1320) may be loaded on the patient platform (1310) and may comprise a first region of interest (1322) having a first longitudinal axis (1323) and a second region of interest (1324) having a second longitudinal axis (1325). As shown in FIG. 13A, an isocenter axis (1338) is substantially parallel to both first and second regions of interest (1322, 1324).

Turning back to FIG. 12, the patient platform may move laterally along the Y-axis to position the first region of interest on the isocenter axis (1208). In some variations, the patient platform may be moved in one or more of pitch and yaw rotation and a lateral direction. To further improve radiotherapy treatment, the patient platform may be moved to align a longitudinal axis of the first region of interest on the isocenter axis (1210). As shown in FIG. 13B, the patient platform (1310) may be moved laterally along the Y-axis to align the first longitudinal axis (1323) onto the isocenter axis (1338). A radiation beam may be emitted from a radiation source to the first region of interest on the isocenter axis (1212).

After treatment of the first region of interest, the patient platform may be moved to position the second region of interest on the isocenter axis (1214). In some variations, the patient platform may be moved to align a longitudinal axis of the second region of interest on the isocenter axis (1216). As shown in FIG. 13C, the patient platform (1310) may be moved laterally along the Y-axis to align the second longitudinal axis (1325) onto the isocenter axis (1338). A radiation beam may be emitted from the radiation source to the second region of interest on the isocenter axis (1218). Of course, the patient platform (1310) may be moved to treat any number of regions of interest of a patient (1320).

If a region of interest changes position at any point before, during, or after radiotherapy treatment due to patient movement on the patient platform (due to breathing, patient discomfort, and the like), the patient platform may be moved to compensate for the patient's change in position using a patient platform controller. For example, if a patient rolls in one direction on the patient platform, the position of the patient platform may be adjusted or rolled in the opposite direction to compensate for the patient's movement. In some variations, the methods described with respect to FIGS. 12 and 13A-13D may be performed using the system described with respect to FIGS. 4A-4E.

Figure 13D:
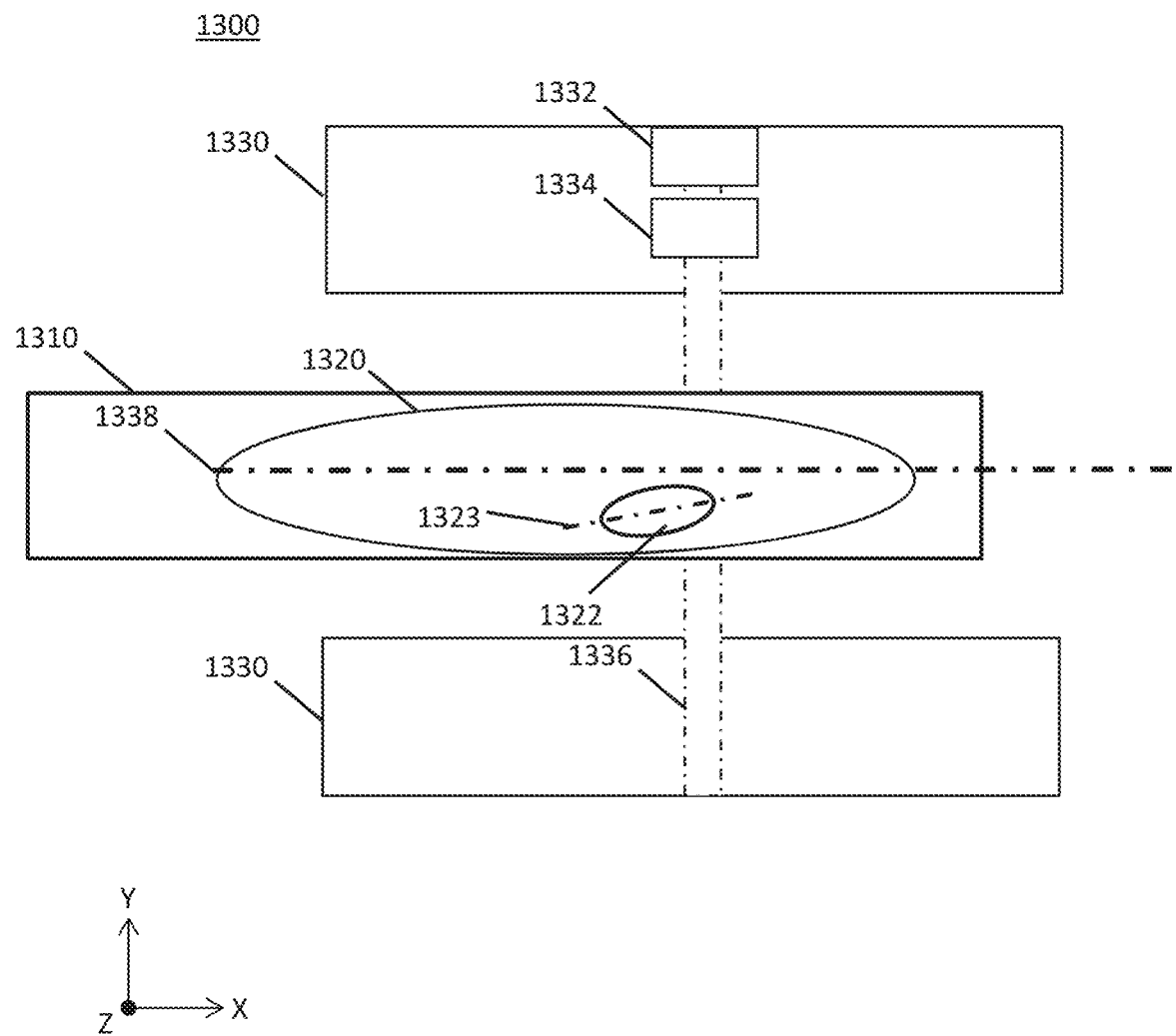
Figure 13E:
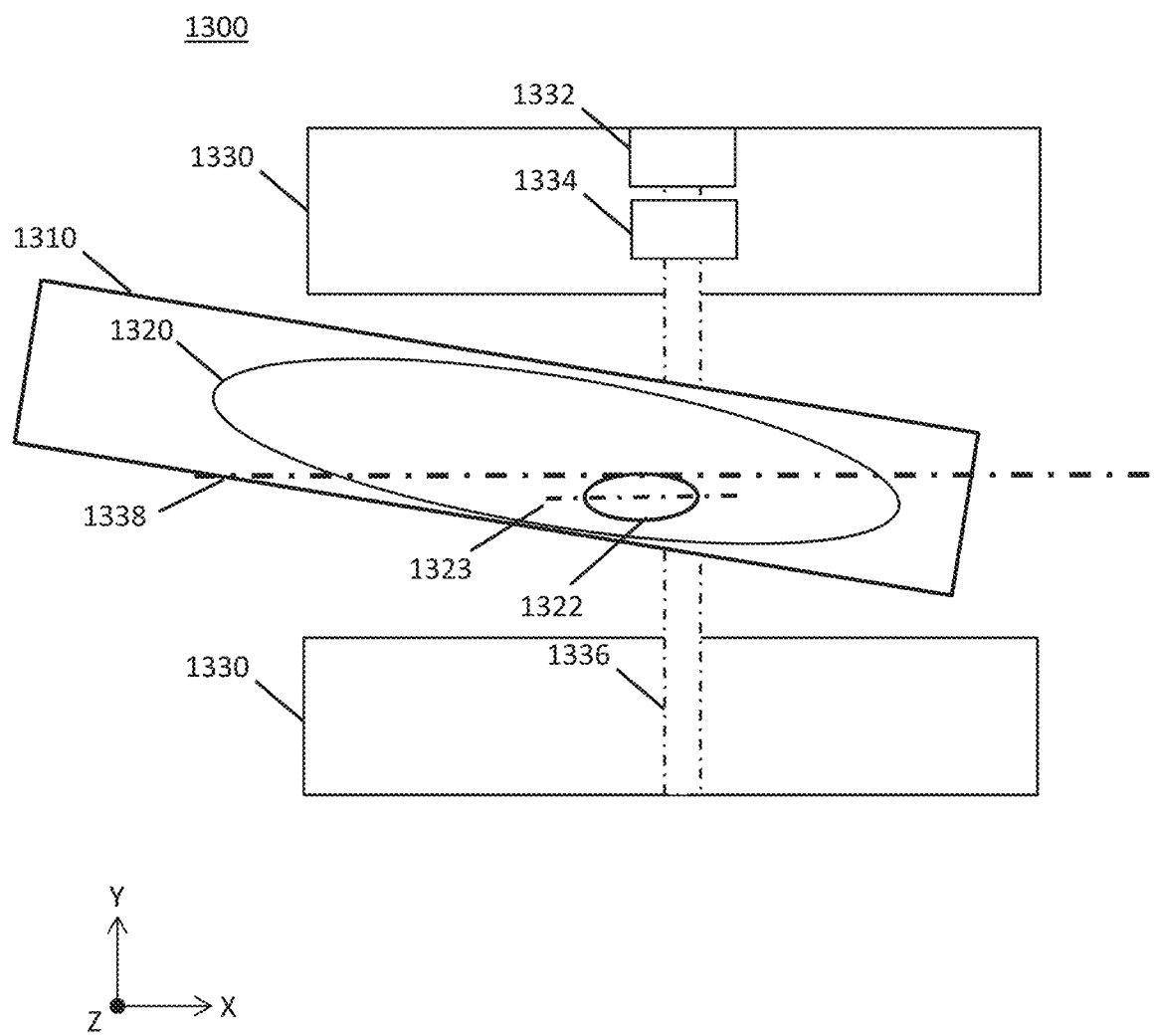

FIG. 13D illustrates another variation where a longitudinal axis (1323) of a region of interest (1322) of patient (1320) is non-parallel to an isocenter axis (1338). The patient platform (1310) may be yawed about the Z-axis to align the longitudinal axis (1323) to the isocenter axis (1338), as shown in FIG. 13E. In some non-limiting, exemplary variations, the patient platform (1310) may yaw about the Z-axis by up to about 15°. Although not illustrated, it should be appreciated that the pitch of the patient platform may be changed to align a longitudinal axis of a region of interest to an isocenter axis.

Position a Patient Head

Figure 14:
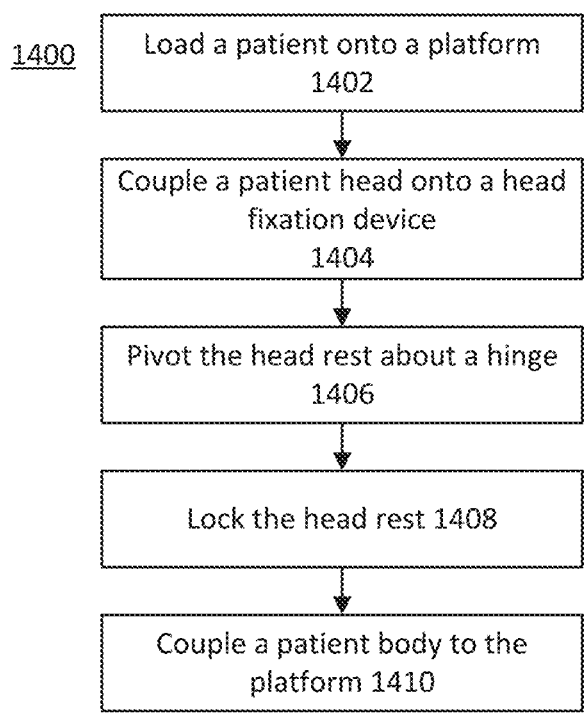
FIG. 14 is a flowchart representation of one variation of a patient head fixing process.

FIG. 14 is a flowchart of one variation of a patient head positioning process (1400). In some variations, the process (1400) may include loading a patient onto a patient platform (1402). A head fixation device may be provided on the patient platform such that a patient head may be coupled to a head rest of the head fixation device (1404). In some variations, a patient head may be held or fixed to the head rest. The head may then be pivoted about a hinge of the head fixation device (1406). The head rest may pitch and yaw relative to the patient platform. The pivoting may be provided by a head rest drive system coupled to the head rest and/or by patient neck flexion. For instance, a radiotransparent pneumatic element may be extended substantially vertically tilt the head rest and to position the patient head at a desired angle. Once the head is at a desired position, the head rest may be locked (1408). One or more portions of a patient body may optionally be coupled to the platform (1410). For instance, a patient torso and/or shoulder may be coupled to the head fixation device and/or patient platform.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

We claim:

1. A radiotherapy patient platform system comprising:
   a radiotransparent patient platform coupled to a base, wherein the patient platform comprises an upper portion coupled to a lower portion;
   an axial drive system coupled to the patient platform, wherein the axial drive system is configured to move the patient platform in an axial direction relative to the base;
   a lateral drive system coupled to the patient platform, wherein the lateral drive system is configured to move the patient platform in a lateral direction relative to the base;
   a vertical drive system coupled to the patient platform, wherein the vertical drive system is configured to move the patient platform in a vertical direction relative to the base, wherein the vertical drive system comprises a first and second scissor element coupled to the patient platform;
   a yaw pivot coupling the upper portion to the lower portion at first ends of the upper and lower portions;
   a yaw drive system coupled to the first end of the upper portion, wherein the yaw drive system is configured to yaw the upper portion relative to the lower portion about the yaw pivot; and
   a pitch drive system coupled to the platform, wherein the pitch drive system is configured to pitch the upper portion relative to the lower portion about a pitch pivot.

2. The system of claim 1 wherein the pitch drive system comprises a first wedge coupled to the yaw drive system and a second wedge coupled to the upper portion.

3. The system of claim 1 wherein the axial drive system is coupled between the lower portion and the lateral drive system, the lateral drive system is coupled between the axial drive system and the yaw drive system, the yaw drive system is coupled between the lateral drive system and the pitch drive system, and the pitch drive system is coupled between the yaw drive system and the upper portion.

4. The system of claim 1 wherein the axial drive system comprises an axial drive element coupled to the first end of the lower portion and an axial rail coupled to the axial drive element.

5. The system of claim 1 wherein the lateral drive system comprises a lateral drive element coupled to the patient platform and a lateral rail coupled to the lateral drive element.

6. The system of claim 1 wherein the vertical drive system comprises a vertical drive element comprising a first linear screw coupled to the first scissor element.

7. The system of claim 6 wherein the vertical drive element comprises a second linear screw coupled to the second scissor element.

8. The system of claim 1, further comprising a handheld controller comprising a switch, wherein the switch is configured to generate a movement signal to control movement of the radiotransparent patient platform.

9. The system of claim 8, wherein the switch comprises at least one of a button, an analog stick, a trackball, a touch screen, a directional pad, a jog dial, a motion detector, an image sensor, and a microphone.

10. The system of claim 8, wherein the handheld controller comprises a docking port configured to dock with a radiotherapy system.

11. The system of claim 10, wherein the radiotherapy system is configured to deliver radiotherapy treatment only when the handheld controller is docked to the radiotherapy system.

12. The system of claim 8, wherein the handheld controller comprises a safety switch.

13. The system of claim 8, wherein the handheld controller comprises a proximity sensor, and wherein the handheld controller is configured to generate different output signals based on the proximity of the handheld controller relative to the radiotransparent patient platform.

14. The system of claim 8, wherein the handheld controller comprises a wireless transmitter configured to transmit the movement signal to control one or more of the drive systems.

15. The system of claim 1, wherein the radiotransparent patient platform comprises a conformable substrate.

16. The system of claim 15, wherein the conformable substrate has a plurality of enclosures and a pressure sensor coupled to the conformable substrate, and wherein the system further comprises a controller configured to independently control a height of each of the plurality of enclosures using the pressure sensor.

17. The system of claim 16, further comprising a pressure channel coupling a pressure source to each of the plurality of enclosures.

18. The system of claim 17, wherein the pressure channel comprises a radiotransparent material substantially transparent to high energy photons.

19. The system of claim 16, wherein the plurality of enclosures comprise a fluid.

20. The system of claim 16, further comprising a thermoelectric layer and a heating element each coupled to the radiotransparent patient platform.

21. The system of claim 20, wherein the thermoelectric layer transitions the conformable substrate between a compliant configuration and a rigid configuration based on temperature.

22. The system of claim 20, further comprising a thermal insulating layer coupled to the thermoelectric layer.

23. The system of claim 1, further comprising a head fixation device comprising a hinge coupled to a head fixation base, a head rest coupled to the hinge, and a head rest drive system coupled to the head rest, wherein the head rest drive system is configured to extend substantially perpendicularly to the head fixation base, wherein the head rest and the head rest drive system each comprise a radiotransparent material substantially transparent to high energy photons.

24. The system of claim 23, wherein the head rest drive system comprises a pneumatic element.

25. The system of claim 23, wherein the head rest drive system comprises an electromechanical element.

26. The system of claim 23, further comprising an actuator coupled to the head rest drive system, wherein the actuator is coupled to a first end of the radiotransparent patient platform.

27. The system of claim 23, wherein the hinge comprises a lock, wherein the lock comprises a plurality of detents and a pin.

\* \* \* \* \*